US010058411B2

(12) United States Patent
Fifer et al.

(10) Patent No.: US 10,058,411 B2
(45) Date of Patent: Aug. 28, 2018

(54) METHOD OF ISOLATING THE CEREBRAL CIRCULATION DURING A CARDIAC PROCEDURE

(71) Applicant: Claret Medical, Inc., Santa Rosa, CA (US)

(72) Inventors: Daniel W. Fifer, Windsor, CA (US); Randall T. Lashinski, Windsor, CA (US); Antony J. Fields, San Francisco, CA (US); Michael Lee, Santa Rosa, CA (US)

(73) Assignee: Claret Madical, Inc., Santa Rosa, CA (US)

( * ) Notice: Subject to any disclaimer, the term of this patent is extended or adjusted under 35 U.S.C. 154(b) by 444 days.

(21) Appl. No.: 14/703,805

(22) Filed: May 4, 2015

(65) Prior Publication Data

US 2015/0335416 A1 Nov. 26, 2015

Related U.S. Application Data

(63) Continuation of application No. 13/338,916, filed on Dec. 28, 2011, now Pat. No. 9,055,997.

(Continued)

(51) Int. Cl.
*A61M 29/00* (2006.01)
*A61F 2/01* (2006.01)
(Continued)

(52) U.S. Cl.
CPC ........ *A61F 2/013* (2013.01); *A61B 17/22031* (2013.01); *A61F 2/01* (2013.01); *A61F 2/2427* (2013.01); *A61F 2002/011* (2013.01); *A61F 2002/015* (2013.01); *A61F 2002/016* (2013.01); *A61F 2002/018* (2013.01);
(Continued)

(58) Field of Classification Search
CPC .......... A61F 2002/015; A61F 2002/016; A61F 2002/018; A61F 2230/0008; A61F 2230/0067; A61F 2230/0093; A61F 2250/0029; A61F 2/013
See application file for complete search history.

(56) References Cited

U.S. PATENT DOCUMENTS 3,472,230 A   10/1969   Fogarty
4,619,246 A   10/1986   Molgaard-Nielsen et al.
(Continued)

FOREIGN PATENT DOCUMENTS

DE   10049812         4/2002
EP   1400257 A2       3/2004
(Continued)

OTHER PUBLICATIONS

Final Office Action for U.S. Appl. No. 13/338,914 dated Jul. 22, 2015, in 14 pages.
(Continued)

*Primary Examiner* — Gregory Anderson
(74) *Attorney, Agent, or Firm* — Knobbe Martens Olson & Bear LLP

(57) ABSTRACT

Single filter and multi-filter endolumenal methods and systems for filtering fluids within the body. In some embodiments a blood filtering system captures and removes particulates dislodged or generated during a surgical procedure and circulating in a patient's vasculature. In some embodiments a filter system protects the cerebral vasculature during a cardiac valve repair or replacement procedure.

20 Claims, 66 Drawing Sheets

Related U.S. Application Data

(60) Provisional application No. 61/428,653, filed on Dec. 30, 2010, provisional application No. 61/493,447, filed on Jun. 4, 2011, provisional application No. 61/550,889, filed on Oct. 24, 2011, provisional application No. 61/556,142, filed on Nov. 4, 2011.

(51) Int. Cl.
  *A61B 17/22* (2006.01)
  *A61F 2/24* (2006.01)

(52) U.S. Cl.
  CPC . *A61F 2210/0014* (2013.01); *A61F 2230/005* (2013.01); *A61F 2230/0006* (2013.01); *A61F 2230/008* (2013.01); *A61F 2230/0008* (2013.01); *A61F 2230/0067* (2013.01); *A61F 2230/0093* (2013.01); *A61F 2250/0029* (2013.01)

(56) References Cited

U.S. PATENT DOCUMENTS

| | | |
|---|---|---|
| 4,630,609 A | 12/1986 | Chin |
| 4,650,466 A | 3/1987 | Luther |
| 4,706,671 A | 11/1987 | Weinrib |
| 4,723,549 A | 2/1988 | Wholey |
| 4,873,978 A | 10/1989 | Ginsburg |
| 5,108,419 A | 4/1992 | Reger |
| 5,192,286 A | 3/1993 | Phan |
| 5,200,248 A | 4/1993 | Thompson et al. |
| 5,329,923 A | 7/1994 | Lundquist |
| 5,348,545 A | 9/1994 | Shani et al. |
| 5,381,782 A | 1/1995 | DeLaRama et al. |
| 5,395,327 A | 3/1995 | Lundquist et al. |
| 5,613,980 A | 3/1997 | Chauhan |
| 5,624,430 A | 4/1997 | Eton et al. |
| 5,662,671 A | 9/1997 | Barbut et al. |
| 5,680,873 A | 10/1997 | Berg et al. |
| 5,707,389 A | 1/1998 | Louw et al. |
| 5,766,151 A | 6/1998 | Valley et al. |
| 5,779,716 A | 7/1998 | Cano et al. |
| 5,814,064 A | 9/1998 | Daniel |
| 5,827,324 A | 10/1998 | Cassell |
| 5,833,650 A | 11/1998 | Imran |
| 5,848,964 A | 12/1998 | Samuels |
| 5,897,529 A | 4/1999 | Ponzi |
| 5,897,819 A | 4/1999 | Miyata et al. |
| 5,910,154 A | 6/1999 | Tsugita et al. |
| 5,910,364 A | 6/1999 | Miyata et al. |
| 5,911,734 A | 6/1999 | Tsugita et al. |
| 5,935,139 A | 8/1999 | Bates |
| 5,980,555 A | 11/1999 | Barbut et al. |
| 5,989,281 A | 11/1999 | Barbut et al. |
| 5,993,469 A | 11/1999 | McKenzie et al. |
| 6,001,118 A | 12/1999 | Daniel |
| 6,010,522 A | 1/2000 | Barbut et al. |
| 6,027,520 A | 2/2000 | Tsugita et al. |
| 6,042,598 A | 3/2000 | Tsugita et al. |
| 6,045,547 A | 4/2000 | Ren et al. |
| 6,051,014 A | 4/2000 | Jang |
| 6,080,140 A | 6/2000 | Swaminathan et al. |
| 6,083,239 A | 7/2000 | Addis |
| 6,096,053 A | 8/2000 | Bates |
| 6,099,534 A | 8/2000 | Bates |
| 6,120,494 A | 9/2000 | Jonkman |
| 6,126,673 A | 10/2000 | Kim et al. |
| 6,129,739 A | 10/2000 | Khosravi |
| 6,142,987 A | 11/2000 | Tsugita |
| 6,146,396 A | 11/2000 | Konya et al. |
| 6,152,946 A | 11/2000 | Broome et al. |
| 6,171,328 B1 | 1/2001 | Addis |
| 6,179,851 B1 | 1/2001 | Barbut et al. |
| 6,179,861 B1 | 1/2001 | Khosravi et al. |
| 6,203,561 B1 | 3/2001 | Ramee et al. |
| 6,214,026 B1 | 4/2001 | Lepak et al. |
| 6,235,045 B1 | 5/2001 | Barbut et al. |
| 6,245,087 B1 | 6/2001 | Addis |
| 6,245,088 B1 | 6/2001 | Lowery |
| 6,245,089 B1 | 6/2001 | Daniel |
| 6,264,663 B1 | 7/2001 | Cano |
| 6,270,513 B1 | 8/2001 | Tsugita et al. |
| 6,277,138 B1 | 8/2001 | Levinson et al. |
| 6,287,321 B1 | 9/2001 | Jang |
| 6,290,710 B1 | 9/2001 | Cryer et al. |
| 6,309,399 B1 | 10/2001 | Barbut et al. |
| 6,325,815 B1 | 12/2001 | Kusleika |
| 6,336,934 B1 | 1/2002 | Gilson et al. |
| 6,346,116 B1 | 2/2002 | Brooks et al. |
| 6,361,545 B1 | 3/2002 | Macoviak et al. |
| 6,364,900 B1 | 4/2002 | Heuser |
| 6,371,970 B1 | 4/2002 | Khosravi et al. |
| 6,371,971 B1 | 4/2002 | Tsugita et al. |
| 6,375,628 B1 | 4/2002 | Zadno-Azizi et al. |
| 6,383,174 B1 | 5/2002 | Eder |
| 6,383,205 B1 | 5/2002 | Samson et al. |
| 6,440,120 B1 | 8/2002 | Maahs |
| 6,454,799 B1 | 11/2002 | Schreck |
| 6,485,502 B2 | 11/2002 | Don Michael |
| 6,499,487 B1 | 12/2002 | McKenzie et al. |
| 6,517,559 B1 | 2/2003 | O'Connell |
| 6,530,939 B1 | 3/2003 | Hopkins et al. |
| 6,537,297 B2 | 3/2003 | Tsugita et al. |
| 6,544,279 B1 | 4/2003 | Hopkins et al. |
| 6,558,356 B2 | 5/2003 | Barbut |
| 6,589,263 B1 | 7/2003 | Hopkins et al. |
| 6,595,983 B2 | 7/2003 | Voda |
| 6,605,102 B1 | 8/2003 | Mazzocchi |
| 6,616,679 B1 | 9/2003 | Khosravi et al. |
| 6,620,148 B1 | 9/2003 | Tsugita |
| 6,620,182 B1 | 9/2003 | Khosravi et al. |
| 6,648,837 B2 | 11/2003 | Kato et al. |
| 6,663,652 B2 | 12/2003 | Daniel et al. |
| 6,676,682 B1 | 1/2004 | Tsugita et al. |
| 6,712,834 B2 | 3/2004 | Yassour et al. |
| 6,712,835 B2 | 3/2004 | Mazzocchi |
| 6,719,717 B1 | 4/2004 | Johnson et al. |
| 6,726,621 B2 | 4/2004 | Suon et al. |
| 6,726,651 B1 | 4/2004 | Robinson et al. |
| 6,726,701 B2 | 4/2004 | Gilson |
| 6,740,061 B1 | 5/2004 | Oslund |
| 6,817,999 B2 | 11/2004 | Berube et al. |
| 6,830,579 B2 | 12/2004 | Barbut |
| 6,843,798 B2 | 1/2005 | Kusleika et al. |
| 6,872,216 B2 | 3/2005 | Daniel |
| 6,881,194 B2 | 4/2005 | Miyata et al. |
| 6,887,258 B2 | 5/2005 | Denison et al. |
| 6,905,490 B2 | 6/2005 | Parodi |
| 6,907,298 B2 | 6/2005 | Smits et al. |
| 6,958,074 B2 | 10/2005 | Russell |
| 6,969,396 B2 | 11/2005 | Krolik et al. |
| 7,011,094 B2 | 3/2006 | Rapacki et al. |
| 7,048,752 B2 | 5/2006 | Mazzocchi |
| 7,094,249 B1 | 8/2006 | Broome |
| 7,115,134 B2 | 10/2006 | Chambers |
| 7,160,255 B2 | 1/2007 | Saadat |
| 7,169,161 B2 | 1/2007 | Bonnette et al. |
| 7,169,165 B2 | 1/2007 | Belef et al. |
| 7,182,757 B2 | 2/2007 | Miyata et al. |
| 7,214,237 B2 | 5/2007 | Don Michael |
| 7,278,974 B2 | 10/2007 | Kato et al. |
| 7,303,575 B2 | 12/2007 | Ogle |
| 7,306,618 B2 | 12/2007 | Demond et al. |
| 7,313,445 B2 | 12/2007 | McVenes et al. |
| 7,323,001 B2 | 1/2008 | Clubb et al. |
| 7,329,278 B2 | 2/2008 | Seguin et al. |
| 7,399,308 B2 | 7/2008 | Borillo et al. |
| 7,410,491 B2 | 8/2008 | Hopkins |
| 7,493,154 B2 | 2/2009 | Bonner et al. |
| 7,559,925 B2 | 7/2009 | Goldfarb et al. |
| 7,572,272 B2 | 8/2009 | Denison et al. |
| 7,621,904 B2 | 11/2009 | McFerran et al. |
| 7,722,634 B2 | 5/2010 | Panetta et al. |
| 7,766,961 B2 | 8/2010 | Patel et al. |
| 7,922,732 B2 | 3/2011 | Mazzocchi et al. |

(56) References Cited

U.S. PATENT DOCUMENTS

| | | |
|---|---|---|
| 7,918,859 B2 | 4/2011 | Katoh et al. |
| 7,976,562 B2 | 7/2011 | Bressler et al. |
| 7,998,104 B2 | 8/2011 | Chang |
| 8,002,790 B2 | 8/2011 | Brady et al. |
| 8,021,351 B2 | 9/2011 | Boldenow et al. |
| 8,052,713 B2 | 11/2011 | Khosravi et al. |
| 8,092,483 B2 | 1/2012 | Galdonik et al. |
| 8,372,108 B2 | 2/2013 | Lashinski |
| 8,382,788 B2 | 2/2013 | Galdonik |
| 8,460,335 B2 | 6/2013 | Carpenter |
| 8,518,073 B2 | 8/2013 | Lashinski |
| 8,753,370 B2 | 6/2014 | Lashinski |
| 8,876,796 B2 | 11/2014 | Fifer et al. |
| 8,974,489 B2 | 3/2015 | Lashinski |
| 9,017,364 B2 | 4/2015 | Fifer et al. |
| 9,055,997 B2 | 6/2015 | Fifer et al. |
| 9,259,306 B2 | 2/2016 | Fifer et al. |
| 9,326,843 B2 | 5/2016 | Lee et al. |
| 9,345,565 B2 | 5/2016 | Fifer et al. |
| 9,480,548 B2 | 11/2016 | Carpenter |
| 9,492,264 B2 | 11/2016 | Fifer et al. |
| 9,566,144 B2 | 2/2017 | Purcell et al. |
| 9,636,205 B2 | 5/2017 | Lee et al. |
| 9,943,395 B2 | 4/2018 | Fifer et al. |
| 2001/0041858 A1 | 11/2001 | Ray et al. |
| 2002/0022858 A1 | 2/2002 | Demond et al. |
| 2002/0026145 A1 | 2/2002 | Bagaoisan et al. |
| 2002/0055767 A1 | 5/2002 | Forde et al. |
| 2002/0068015 A1 | 6/2002 | Polaschegg et al. |
| 2002/0077596 A1 | 6/2002 | McKenzie et al. |
| 2002/0095170 A1 | 7/2002 | Krolik et al. |
| 2002/0095172 A1 | 7/2002 | Mazzocchi et al. |
| 2002/0123761 A1 | 9/2002 | Barbut et al. |
| 2002/0161394 A1 | 10/2002 | Macoviak et al. |
| 2002/0165571 A1 | 11/2002 | Herbert et al. |
| 2002/0165573 A1 | 11/2002 | Barbut |
| 2003/0100919 A1 | 5/2003 | Hopkins et al. |
| 2003/0130684 A1 | 7/2003 | Brady et al. |
| 2003/0144686 A1 | 7/2003 | Martinez et al. |
| 2003/0171770 A1 | 9/2003 | Kusleika et al. |
| 2003/0199960 A1 | 10/2003 | Paskar |
| 2004/0002730 A1 | 1/2004 | Denison et al. |
| 2004/0006370 A1 | 1/2004 | Tsugita |
| 2004/0044350 A1 | 3/2004 | Martin et al. |
| 2004/0044360 A1 | 3/2004 | Lowe |
| 2004/0064092 A1 | 4/2004 | Tsugita et al. |
| 2004/0093015 A1 | 5/2004 | Ogle |
| 2004/0167565 A1 | 8/2004 | Beulke et al. |
| 2004/0193206 A1 | 9/2004 | Gerberding |
| 2004/0215167 A1 | 10/2004 | Belson |
| 2004/0215230 A1 | 10/2004 | Frazier |
| 2004/0220611 A1 | 11/2004 | Ogle |
| 2004/0225321 A1 | 11/2004 | Krolik et al. |
| 2004/0230220 A1 | 11/2004 | Osborne |
| 2004/0243175 A1 | 12/2004 | Don Michael |
| 2004/0254601 A1 | 12/2004 | Eskuri |
| 2004/0254602 A1 | 12/2004 | Lehe et al. |
| 2005/0010285 A1 | 1/2005 | Lambrecht et al. |
| 2005/0065397 A1 | 3/2005 | Saadat et al. |
| 2005/0080356 A1 | 4/2005 | Dapolito et al. |
| 2005/0085847 A1 | 4/2005 | Galdonik et al. |
| 2005/0101987 A1 | 5/2005 | Salahieh |
| 2005/0131449 A1 | 6/2005 | Salahieh et al. |
| 2005/0137696 A1 | 6/2005 | Salahieh |
| 2005/0177132 A1 | 8/2005 | Lentz et al. |
| 2005/0209631 A1 | 9/2005 | Galdonik et al. |
| 2005/0277976 A1 | 12/2005 | Galdonik et al. |
| 2006/0015136 A1 | 1/2006 | Besselink |
| 2006/0015138 A1 | 1/2006 | Gertner |
| 2006/0030877 A1 | 2/2006 | Martinez et al. |
| 2006/0041188 A1 | 2/2006 | Dirusso et al. |
| 2006/0047301 A1 | 3/2006 | Ogle |
| 2006/0089618 A1 | 4/2006 | McFerran et al. |
| 2006/0089666 A1 | 4/2006 | Linder et al. |
| 2006/0100658 A1 | 5/2006 | Obana et al. |
| 2006/0100662 A1 | 5/2006 | Daniel et al. |
| 2006/0129180 A1 | 6/2006 | Tsugita et al. |
| 2006/0135961 A1 | 6/2006 | Rosenman et al. |
| 2006/0136043 A1 | 6/2006 | Cully et al. |
| 2006/0149350 A1 | 7/2006 | Patel et al. |
| 2006/0161241 A1 | 7/2006 | Barbut et al. |
| 2006/0200047 A1 | 9/2006 | Galdonik et al. |
| 2006/0200191 A1 | 9/2006 | Zadno-Azizi |
| 2006/0259066 A1 | 11/2006 | Euteneuer |
| 2007/0005131 A1 | 1/2007 | Taylor |
| 2007/0043259 A1 | 2/2007 | Jaffe et al. |
| 2007/0060944 A1 | 3/2007 | Boldenow et al. |
| 2007/0088244 A1 | 4/2007 | Miller et al. |
| 2007/0088383 A1 | 4/2007 | Pal et al. |
| 2007/0173878 A1 | 7/2007 | Heuser |
| 2007/0191880 A1 | 8/2007 | Cartier et al. |
| 2007/0208302 A1 | 9/2007 | Webster et al. |
| 2007/0244504 A1 | 10/2007 | Keegan et al. |
| 2008/0004687 A1 | 1/2008 | Barbut |
| 2008/0033467 A1 | 2/2008 | Miyamoto et al. |
| 2008/0058860 A1 | 3/2008 | Demond et al. |
| 2008/0065145 A1 | 3/2008 | Carpenter |
| 2008/0065147 A1 | 3/2008 | Mazzocchi et al. |
| 2008/0086110 A1 | 4/2008 | Galdonik et al. |
| 2008/0109088 A1 | 5/2008 | Galdonik et al. |
| 2008/0125848 A1 | 5/2008 | Kusleika et al. |
| 2008/0154153 A1 | 6/2008 | Heuser |
| 2008/0172066 A9 | 7/2008 | Galdonik et al. |
| 2008/0188884 A1 | 8/2008 | Gilson et al. |
| 2008/0234722 A1 | 9/2008 | Bonnette et al. |
| 2008/0262442 A1 | 10/2008 | Carlin et al. |
| 2008/0300462 A1 | 12/2008 | Intoccia et al. |
| 2009/0024072 A1 | 1/2009 | Criado et al. |
| 2009/0024153 A1 | 1/2009 | Don Michael |
| 2009/0069840 A1 | 3/2009 | Hallisey |
| 2009/0198269 A1 | 8/2009 | Hannes et al. |
| 2009/0203962 A1 | 8/2009 | Miller et al. |
| 2009/0254172 A1 | 10/2009 | Grewe et al. |
| 2009/0287187 A1 | 11/2009 | Legaspi et al. |
| 2009/0326575 A1 | 12/2009 | Galdonik |
| 2010/0004633 A1 | 1/2010 | Rothe et al. |
| 2010/0010476 A1 | 1/2010 | Galdonik et al. |
| 2010/0063537 A1 | 3/2010 | Ren et al. |
| 2010/0106182 A1 | 4/2010 | Patel et al. |
| 2010/0179583 A1 | 7/2010 | Carpenter et al. |
| 2010/0179584 A1 | 7/2010 | Carpenter et al. |
| 2010/0179585 A1 | 7/2010 | Carpenter et al. |
| 2010/0179647 A1 | 7/2010 | Carpenter et al. |
| 2010/0185216 A1 | 7/2010 | Garrison et al. |
| 2010/0211095 A1 | 8/2010 | Carpenter |
| 2010/0228280 A1 | 9/2010 | Groothuis et al. |
| 2010/0312268 A1 | 12/2010 | Belson |
| 2010/0324589 A1 | 12/2010 | Carpenter et al. |
| 2011/0066221 A1 | 3/2011 | White et al. |
| 2011/0282379 A1 | 11/2011 | Lee et al. |
| 2012/0046739 A1 | 2/2012 | von Oepen et al. |
| 2012/0095500 A1 | 4/2012 | Heuser |
| 2012/0172915 A1 | 7/2012 | Fifer et al. |
| 2012/0172916 A1 | 7/2012 | Fifer et al. |
| 2012/0172917 A1 | 7/2012 | Fifer et al. |
| 2012/0172919 A1 | 7/2012 | Fifer et al. |
| 2012/0172920 A1 | 7/2012 | Fifer et al. |
| 2012/0203265 A1 | 8/2012 | Heuser |
| 2013/0123835 A1 | 5/2013 | Anderson et al. |
| 2013/0131714 A1 | 5/2013 | Wang et al. |
| 2013/0231694 A1 | 9/2013 | Lashinski |
| 2014/0052170 A1 | 2/2014 | Heuser et al. |
| 2014/0094843 A1 | 4/2014 | Heuser |
| 2014/0100597 A1 | 4/2014 | Wang et al. |
| 2014/0243877 A9 | 8/2014 | Lee et al. |
| 2014/0282379 A1 | 9/2014 | Lee et al. |
| 2015/0039016 A1 | 2/2015 | Naor et al. |
| 2015/0209131 A1 | 7/2015 | Fifer et al. |
| 2015/0230910 A1 | 8/2015 | Lashinski et al. |
| 2016/0058541 A1 | 3/2016 | Schotzko et al. |
| 2016/0262864 A1 | 9/2016 | Von Mangoldt et al. |
| 2016/0310255 A1 | 10/2016 | Purcell et al. |
| 2017/0042658 A1 | 2/2017 | Lee et al. |

(56) References Cited

U.S. PATENT DOCUMENTS

| | | | |
|---|---|---|---|
| 2017/0112609 | A1 | 4/2017 | Purcell et al. |
| 2017/0181834 | A1 | 6/2017 | Fifer et al. |
| 2017/0202657 | A1 | 7/2017 | Lee et al. |

FOREIGN PATENT DOCUMENTS

| | | |
|---|---|---|
| EP | 1253871 | 2/2007 |
| EP | 2303384 | 4/2011 |
| EP | 2391303 | 12/2011 |
| EP | 2480165 | 8/2012 |
| EP | 2658476 | 11/2013 |
| EP | 2387427 | 8/2014 |
| JP | 2003-505216 | 2/2003 |
| JP | 2003-526451 | 9/2003 |
| JP | 2003-290231 | 10/2003 |
| JP | 3535098 B2 | 6/2004 |
| JP | 2006-500187 | 1/2006 |
| JP | 2008-511401 | 4/2008 |
| JP | 2008-515463 | 5/2008 |
| JP | 2011-525405 A | 9/2011 |
| WO | WO 99/23976 | 5/1999 |
| WO | WO 01/67989 | 9/2001 |
| WO | WO 2004/026175 | 4/2004 |
| WO | WO 2005/118050 | 12/2005 |
| WO | WO 2006/026371 | 3/2006 |
| WO | WO 2008/033845 | 3/2008 |
| WO | WO 2008/100790 | 8/2008 |
| WO | WO 2008/113857 | 9/2008 |
| WO | WO 2009/032834 | 3/2009 |
| WO | WO 2010/0008451 | 1/2010 |
| WO | WO 2010/081025 | 7/2010 |
| WO | WO 2010/083527 A2 | 7/2010 |
| WO | WO 2010/088520 A2 | 8/2010 |
| WO | WO 2011/034718 A2 | 3/2011 |
| WO | WO 2011/017103 A2 | 10/2011 |
| WO | WO 2012/092377 A1 | 7/2012 |

OTHER PUBLICATIONS

Final Office Action for U.S. Appl. No. 13/338,957 dated Jul. 21, 2015, in 7 pages.
Final Office Action for U.S. Appl. No. 13/338,916 dated Jul. 5, 2013, in 13 pages.
Final Office Action for U.S. Appl. No. 13/338,957 dated Jul. 3, 2013, in 12 pages.
Final Office Action for U.S. Appl. No. 13/338,957 dated Apr. 23, 2014 in 13 pages.
Final Office Action for U.S. Appl. No. 13/338,966 dated Jun. 18, 2013, in 10 pages.
Final Office Action for U.S. Appl. No. 13/338,982 dated Jun. 26, 2013, in 11 pages.
Final Office Action for U.S. Appl. No. 13/338,995 dated Sep. 27, 2013, in 13 pages.
Notice of Allowance for U.S. Appl. No. 13/338,916 dated Feb. 2, 2015, in 21 pages.
Notice of Allowance for U.S. Appl. No. 13/338,966 dated Jul. 9, 2014, in 21 pages.
Office Action for U.S. Appl. No. 13/338,914 dated Jan. 13, 2015, in 17 pages.
Office Action for U.S. Appl. No. 13/338,916 dated Mar. 1, 2013, in 11 pages.
Office Action for U.S. Appl. No. 13/338,957 dated Jan. 2, 2015, in 8 pages.
Office Action for U.S. Appl. No. 13/338,957 dated Mar. 15, 2013, in 12 pages.
Office Action for U.S. Appl. No. 13/338,966 dated Jun. 18, 2013, in 10 pages.
Office Action for U.S. Appl. No. 13/338,966 dated Mar. 14, 2013, in 9 pages.
Office Action for U.S. Appl. No. 13/338,982 dated Mar. 1, 2013, in 12 pages.
Office Action for U.S. Appl. No. 13/338,982 dated Oct. 24, 2014, in 7 pages.
Office Action for U.S. Appl. No. 13/338,995 dated Jun. 26, 2014, in 10 pages.
Office Action for U.S. Appl. No. 13/338,995 dated Mar. 1, 2013, in 11 pages.
Final Office Action for U.S. Appl. No. 13/338,982 dated Jun. 19, 2015, in 11 pages.
Notice of Allowance for U.S. Appl. No. 13/338,995 dated Dec. 19, 2014, in 13 pages.
Notice of Allowance for U.S. Appl. No. 13/338,916 dated Feb. 2, 2015, in 11 pages.
Notice of Allowance for U.S. Appl. No. 13/338,982 dated Oct. 9, 2015, in 8 pages.
Notice of Allowance for U.S. Appl. No. 13/338,914 dated Jul. 7, 2016, in 8 pages.
Notice of Allowance for U.S. Appl. No. 14/693,763 dated Dec. 21, 2016, in 24 pages.
Office Action for U.S. Appl. No. 13/338,914 dated Dec. 15, 2015, in 9 pages.
Office Action for U.S. Appl. No. 14/662,172 dated Aug. 28, 2017, in 16 pages.
Internet Archive Wayback Machine; Fiber Innovative Technology: Fit Capabilities; downloaded from http://web.archive.org/web/20010217040848/http://www.fitfibers.com/capabilities.htm (Archived Feb. 17, 2001; printed on Dec. 12, 2016).
Internet Archive Wayback Machine; Fiber Innovative Technology: 4DG Fibers; downloaded from http://web.archive.org/web/20011030070010/http://fitfibers.com/4DG_Fibers.htm (Archived Oct. 30, 2001; printed on Dec. 12, 2016).
Internet Archive Wayback Machine; Fiber Innovative Technology: Fit Products; downloaded from http://web.archive.org/web/20010408003529/http://www.fitfibers.com/product.htm (Archived Apr. 8, 2001; printed on Dec. 12, 2016).

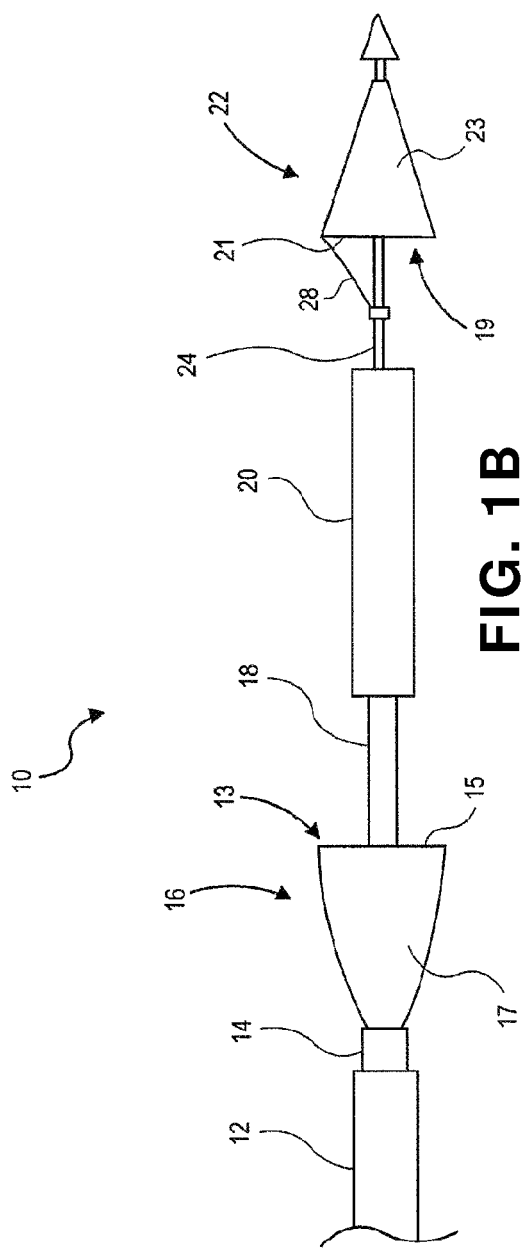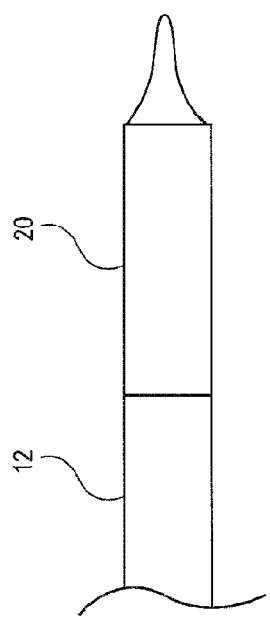
FIG. 1B
FIG. 1C

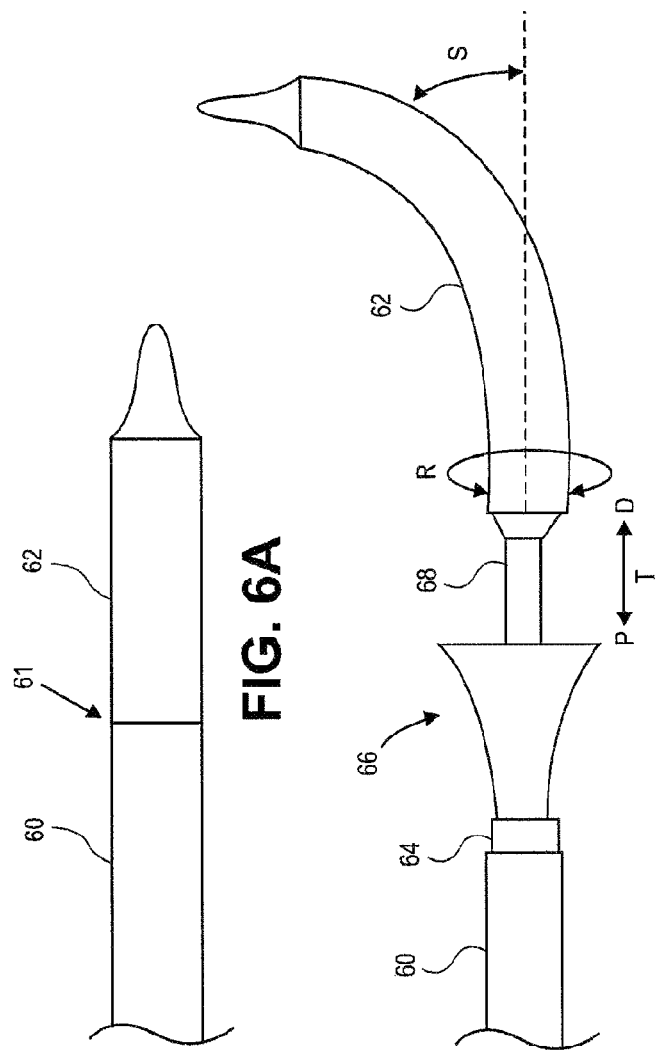

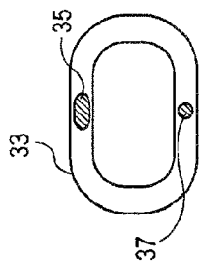 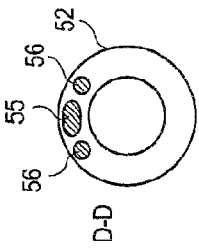
FIG. 7B / FIG. 7C
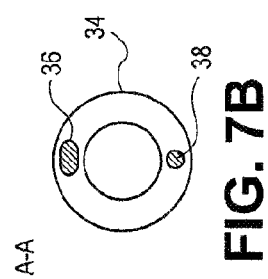  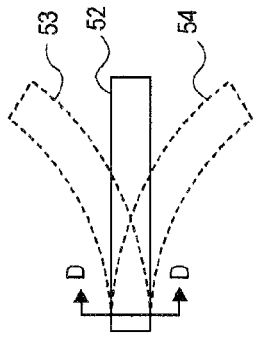
FIG. 8B / FIG. 8C / FIG. 10B
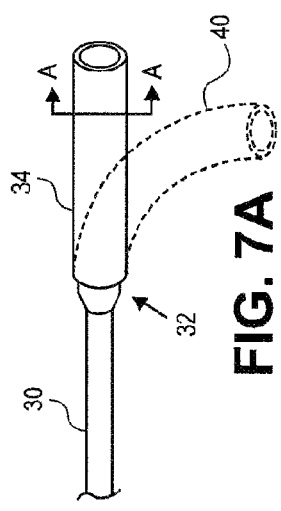 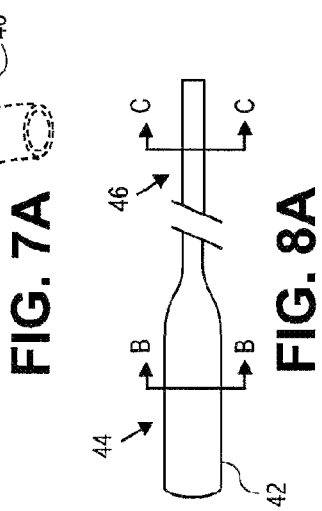 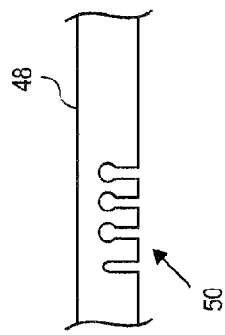
FIG. 7A / FIG. 8A / FIG. 10A
FIG. 9A

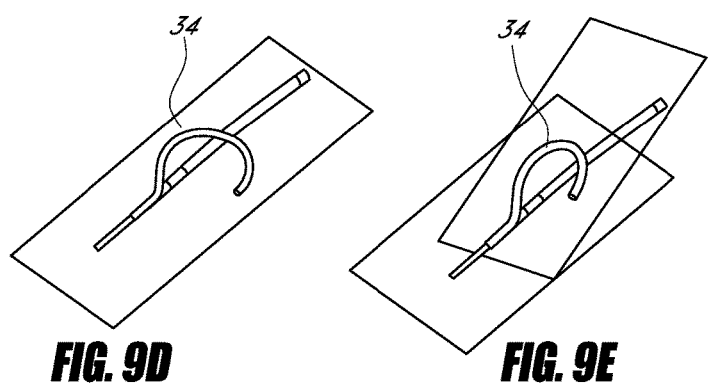

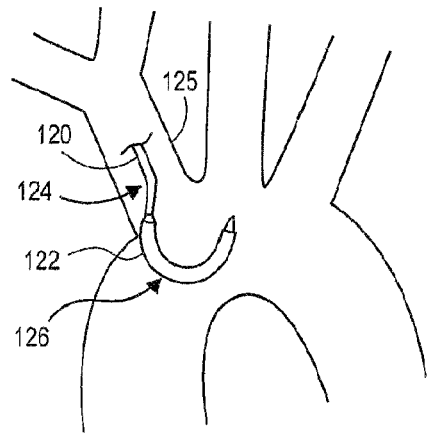
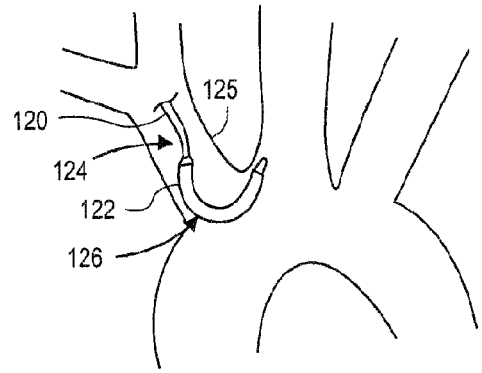
FIG. 13A     FIG. 13B
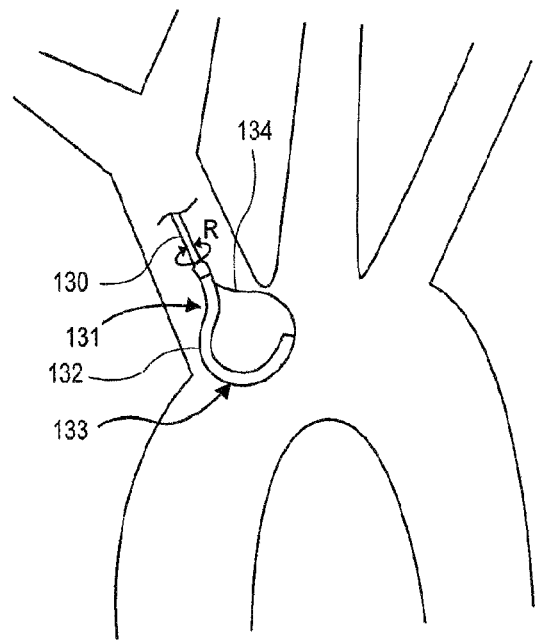
FIG. 14

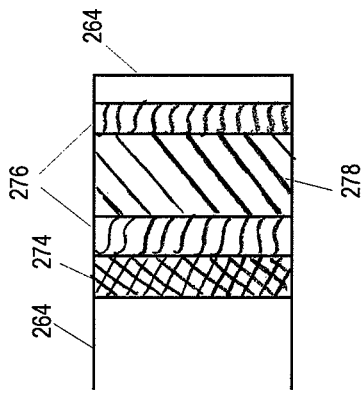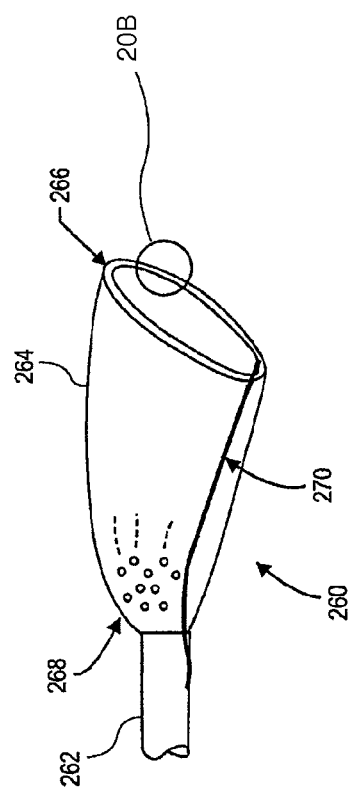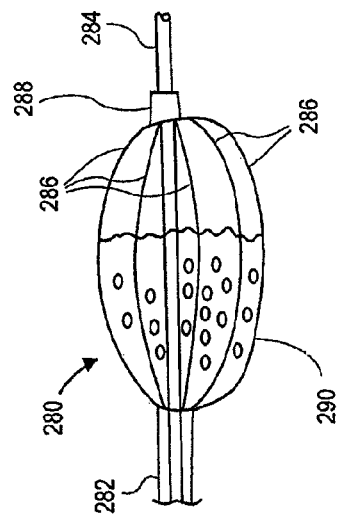

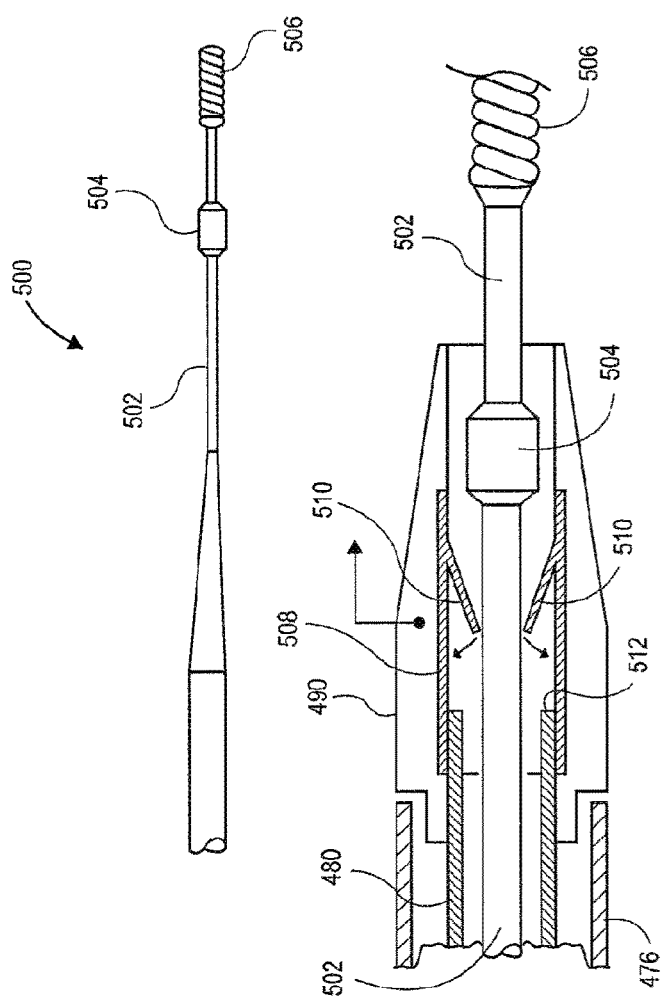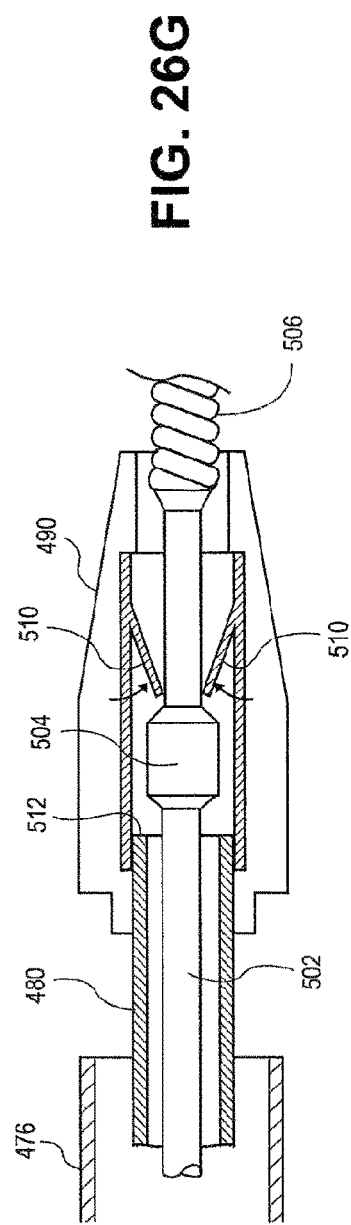

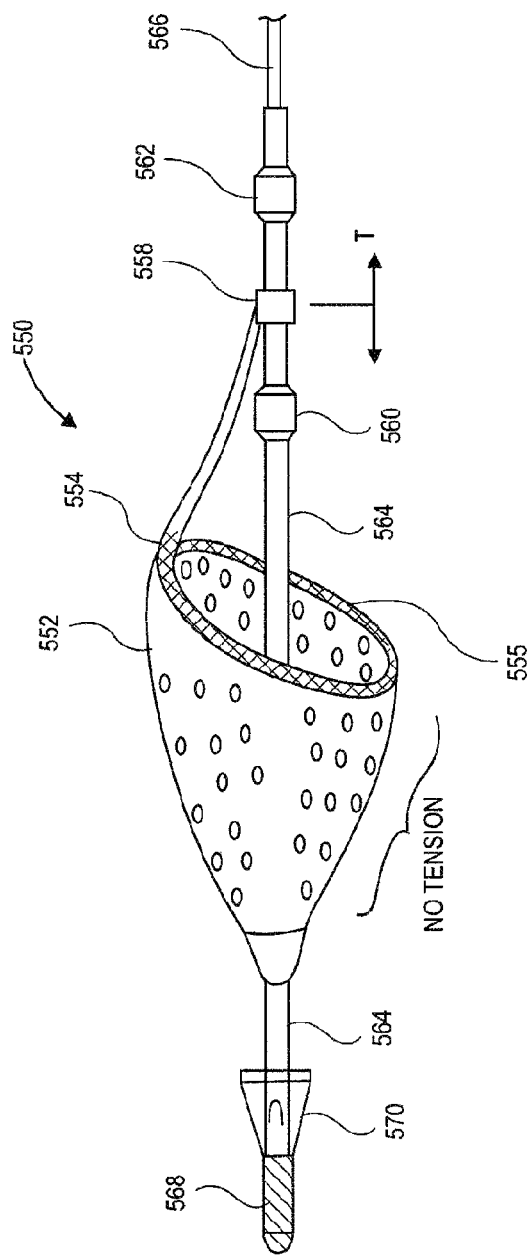

FIG. 29A
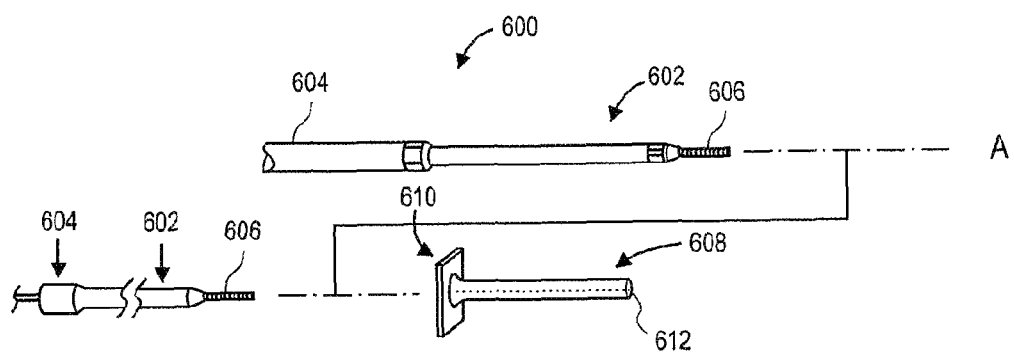
FIG. 29B
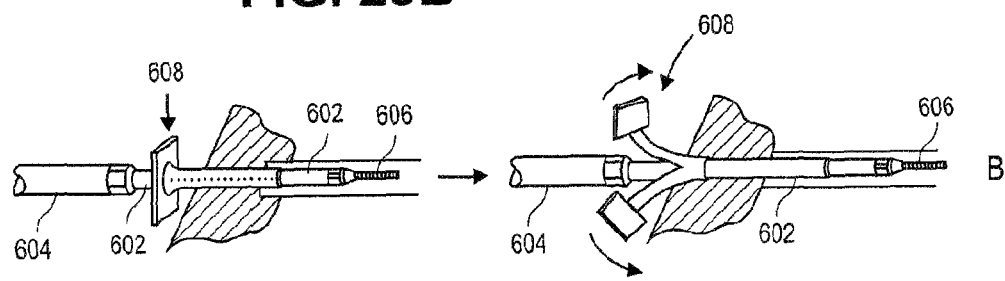
FIG. 29C  FIG. 29D
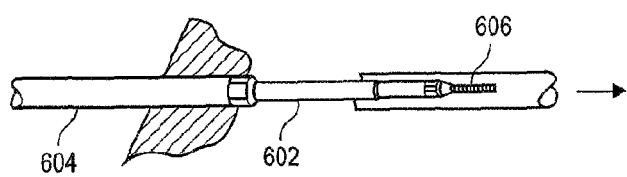
FIG. 29E

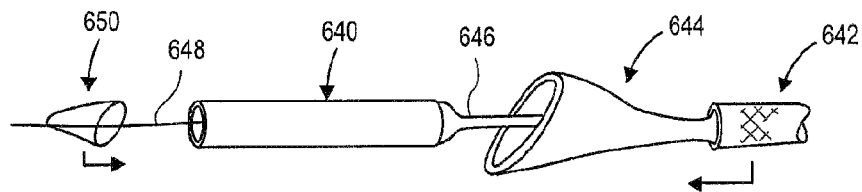
FIG. 30A
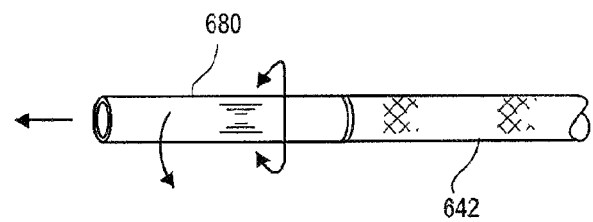
FIG. 30B
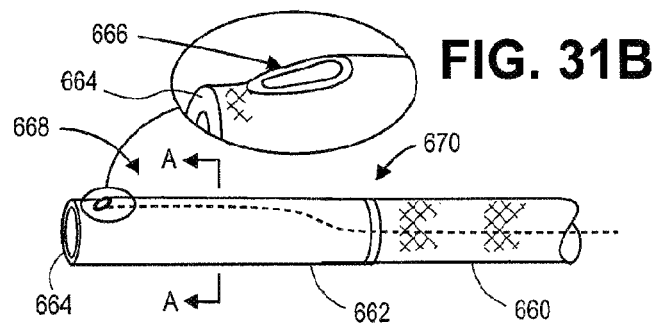
FIG. 31B
FIG. 31A
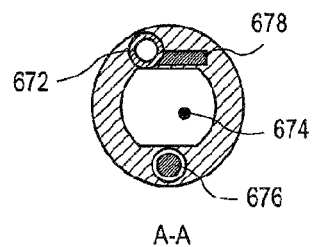
A-A
FIG. 31C

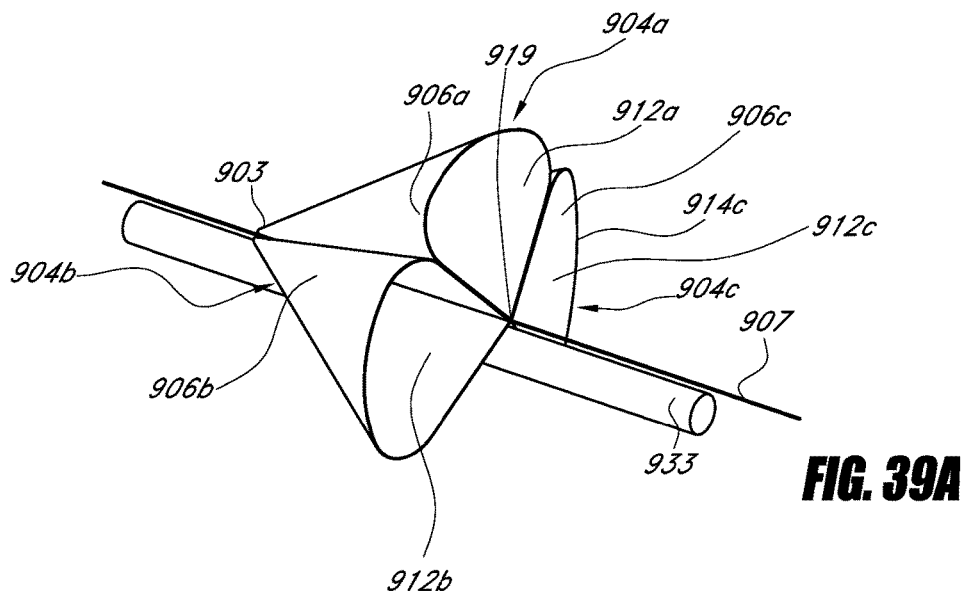
FIG. 39A
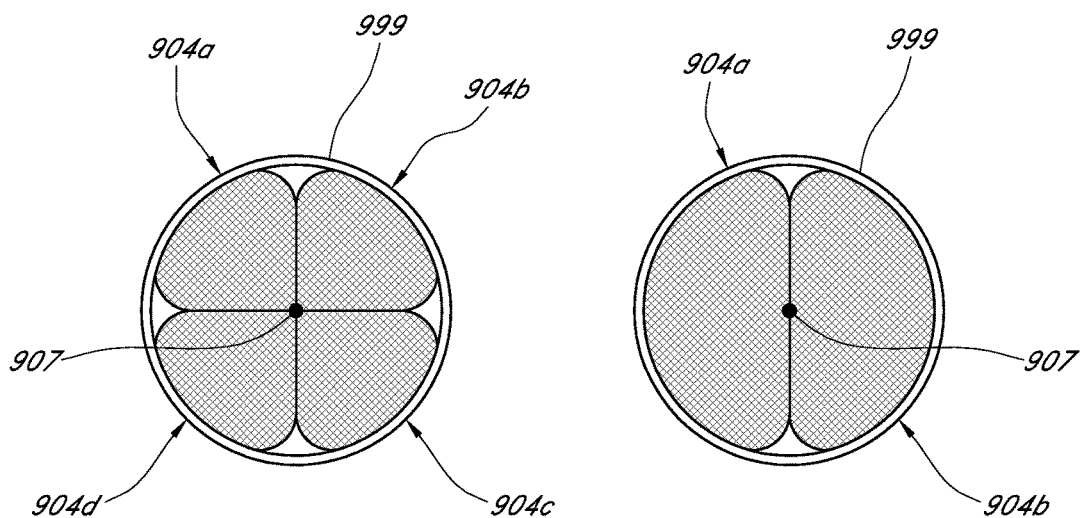
FIG. 39B  FIG. 39C
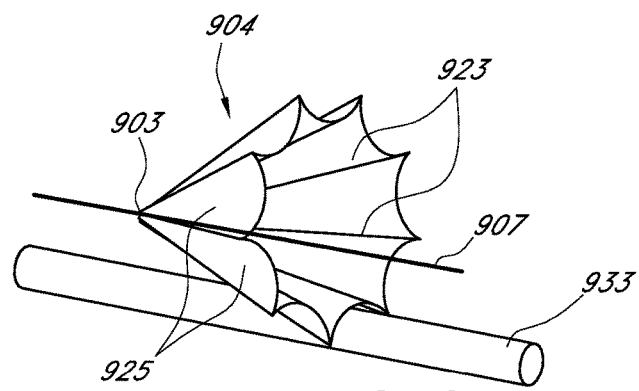
FIG. 40A

METHOD OF ISOLATING THE CEREBRAL CIRCULATION DURING A CARDIAC PROCEDURE

CROSS-REFERENCE TO RELATED APPLICATIONS

This application is a continuation of U.S. application Ser. No. 13/338,916, filed Dec. 28, 2011, now U.S. Pat. No. 9,055,997, which claims the priority benefit under 35 U.S.C. § 119(e) to U.S. Provisional Application No. 61/428,653, filed Dec. 30, 2010; U.S. Provisional Application No. 61/493,447, filed Jun. 4, 2011; U.S. Provisional Application No. 61/550,889, filed Oct. 24, 2011; and U.S. Provisional Application No. 61/556,142, filed Nov. 4, 2011, the entire contents of which are hereby incorporated by reference and should be considered a part of this specification.

BACKGROUND OF THE INVENTION

Field of the Invention

In general, the disclosure relates to methods and apparatuses for filtering blood. The filtration systems can be catheter-based for insertion into a patient's vascular system.

Description of the Related Art

Thromboembolic disorders, such as stroke, pulmonary embolism, peripheral thrombosis, atherosclerosis, and the like, affect many people. These disorders are a major cause of morbidity and mortality in the United States and throughout the world. Thromboembolic events are characterized by an occlusion of a blood vessel. The occlusion can be caused by a clot which is viscoelastic (jelly-like) and is comprised of platelets, fibrinogen, and other clotting proteins.

Percutaneous aortic valve replacement has been in development for some time now and stroke rates related to this procedure are between four and twenty percent. During catheter delivery and valve implantation plaque or other material may be dislodged from the vasculature and may travel through the carotid circulation and into the brain. When an artery is occluded by a clot or other embolic material, tissue ischemia (lack of oxygen and nutrients) develops. The ischemia will progress to tissue infarction (cell death) if the occlusion persists. Infarction does not develop or is greatly limited if the flow of blood is reestablished rapidly. Failure to reestablish blood-flow can lead to the loss of limb, angina pectoris, myocardial infarction, stroke, or even death.

Occlusion of the venous circulation by thrombi leads to blood stasis which can cause numerous problems. The majority of pulmonary embolisms are caused by emboli that originate in the peripheral venous system. Reestablishing blood flow and removal of the thrombus is highly desirable.

Techniques exist to reestablish blood flow in an occluded vessel. One common surgical technique, an embolectomy, involves incising a blood vessel and introducing a balloon-tipped device (such as a Fogarty catheter) to the location of the occlusion. The balloon is then inflated at a point beyond the clot and used to translate the obstructing material back to the point of incision. The obstructing material is then removed by the surgeon. While such surgical techniques have been useful, exposing a patient to surgery may be traumatic and is best avoided when possible. Additionally, the use of a Fogarty catheter may be problematic due to the possible risk of damaging the interior lining of the vessel as the catheter is being withdrawn.

A common percutaneous technique is referred to as balloon angioplasty where a balloon-tipped catheter is introduced into a blood vessel, typically through an introducing catheter. The balloon-tipped catheter is then advanced to the point of the occlusion and inflated in order to dilate the stenosis. Balloon angioplasty is appropriate for treating vessel stenosis but is generally not effective for treating acute thromboembolisms.

Another percutaneous technique is to place a microcatheter near the clot and infuse Streptokinase, Urokinase, or other thrombolytic agents to dissolve the clot. Unfortunately, thrombolysis typically takes hours or days to be successful. Additionally, thrombolytic agents can cause hemorrhage and in many patients the agents cannot be used at all.

Another problematic area is the removal of foreign bodies. Foreign bodies introduced into the circulation can be fragments of catheters, pace-maker electrodes, guide wires, and erroneously placed embolic material such as thrombogenic coils. Retrieval devices exist for the removal of foreign bodies, some of which form a loop that can ensnare the foreign material by decreasing the size of the diameter of the loop around the foreign body. The use of such removal devices can be difficult and sometimes unsuccessful.

Moreover, systems heretofore disclosed in the art are generally limited by size compatibility and the increase in vessel size as the emboli is drawn out from the distal vascular occlusion location to a more proximal location near the heart. If the embolectomy device is too large for the vessel it will not deploy correctly to capture the clot or foreign body, and if too small in diameter it cannot capture clots or foreign bodies across the entire cross section of the blood vessel. Additionally, if the embolectomy device is too small in retaining volume then as the device is retracted the excess material being removed can spill out and be carried by flow back to occlude another vessel downstream.

Various thrombectomy and foreign matter removal devices have been disclosed in the art. Such devices, however, have been found to have structures which are either highly complex or lacking in sufficient retaining structure. Disadvantages associated with the devices having highly complex structure include difficulty in manufacturability as well as difficulty in use in conjunction with microcatheters. Recent developments in the removal device art features umbrella filter devices having self folding capabilities. Typically, these filters fold into a pleated condition, where the pleats extend radially and can obstruct retraction of the device into the microcatheter sheathing.

Extraction systems are needed that can be easily and controllably deployed into and retracted from the circulatory system for the effective removal of clots and foreign bodies. There is also a need for systems that can be used as temporary arterial or venous filters to capture and remove thromboemboli generated during endovascular procedures. The systems should also be able to be properly positioned in the desired location. Additionally, due to difficult-to-access anatomy such as the cerebral vasculature and the neurovasculature, the systems should have a small collapsed profile.

The risk of dislodging foreign bodies is also prevalent in certain surgical procedures. It is therefore further desirable that such emboli capture and removal apparatuses are similarly useful with surgical procedures such as, without limitation, cardiac valve replacement, cardiac bypass grafting, cardiac reduction, or aortic replacement.

SUMMARY OF THE INVENTION

One aspect of the disclosure is a catheter-based endovascular system and method of use for filtering blood that captures and removes particles caused as a result of a surgical or endovascular procedures. The method and system include a first filter placed in a first vessel within the patient's vascular system and a second filter placed in a second vessel within the patient's vascular system. In this manner, the level of particulate protection is thereby increased.

One aspect of the disclosure is an endovascular filtration system and method of filtering blood that protects the cerebral vasculature from embolisms instigated or foreign bodies dislodged during a surgical procedure. In this aspect, the catheter-based filtration system is disposed at a location in the patient's arterial system between the site of the surgical procedure and the cerebral vasculature. The catheter-based filtration system is inserted and deployed at the site to capture embolisms and other foreign bodies and prevent their travel to the patient's cerebral vasculature so as to avoid or minimize thromboembolic disorders such as a stroke.

One aspect of the disclosure is an endovascular filtration system and method of filtering blood that provides embolic protection to the cerebral vasculature during a cardiac or cardiothoracic surgical procedure. According to this aspect, the filtration system is a catheter-based system provided with at least a first filter and a second filter. The first filter is positioned within the brachiocephalic artery, between the aorta and the right common carotid artery, with the second filter being positioned within the left common carotid artery.

One aspect of the disclosure is a catheter-based endovascular filtration system including a first filter and a second filter, wherein the system is inserted into the patient's right brachial or right radial artery. The system is then advanced through the patient's right subclavian artery and into the brachiocephalic artery. Alternately, the system may be inserted directly into the right subclavian artery. At a position within the brachiocephalic trunk between the aorta and the right common carotid artery, the catheter-based system is manipulated to deploy the first filter. The second filter is then advanced through or adjacent to the deployed first filter into the aorta and then into the left common carotid artery. Once in position within the left common carotid artery the catheter-based system is further actuated to deploy the second filter. After the surgical procedure is completed, the second filter and the first filter are, respectively, collapsed and withdrawn from the arteries and the catheter-based filtration system is removed from the patient's vasculature. In an alternate embodiment, either or both the first and second filters may be detached from the filtration system and left inside the patient for a therapeutic period of time.

One aspect of the disclosure is a catheter-based filtration system comprising a handle, a first sheath, a first filter, a second sheath and a second filter. The first and second sheaths are independently actuatable. The handle can be a single or multiple section handle. The first sheath is translatable relative to the first filter to enact deployment of the first filter in a first vessel. The second sheath is articulatable from a first configuration to one or more other configurations. The extent of articulation applied to the second sheath is determined by the anatomy of a second vessel to which access is to be gained. The second filter is advanced through the articulated second sheath and into the vessel accessed by the second sheath and, thereafter, deployed in the second vessel. Actuation of the first sheath relative to the first filter and articulation of the second filter is provided via the handle. In some embodiments, the handle includes a locking mechanism configured to lock the first sheath relative to the second sheath. In certain embodiments, the handle also includes a distal flush port.

In some aspects of the disclosure, the second filter is carried on a guiding member having a guidewire lumen extending therethrough. In certain aspects, the guiding member is a catheter shaft. A guiding member having a guidewire lumen allows the user to precisely deliver the second filter by advancing the filter system over the guidewire. The guiding member can be configured to have increased column strength to aid advancement of the second filter. In some aspects, the guiding member includes a flexible portion to better position the second filter within the vessel.

In some aspects the first sheath is a proximal sheath, the first filter is a proximal filter, the second sheath is a distal sheath, and the second filter is a distal filter. The proximal sheath is provided with a proximal hub housed within and in sliding engagement with the handle. Movement of the proximal hub causes translation of the proximal sheath relative to the proximal filter. The distal sheath includes a distal shaft section and a distal articulatable sheath section. A wire is provided from the handle to the distal articulatable sheath section. Manipulation of the handle places tension on the wire causing the distal articulatable sheath section to articulate from a first configuration to one or more other configurations. The articulatable distal sheath is capable of rotation, translation, and deflection (both in a single plane and both partially in a first plane and partially in a second, different plane). In some embodiments, the handle includes a locking mechanism to prevent the articulatable distal sheath from deviating from a desired configuration. In certain embodiments, the locking mechanism may lock automatically when the operator actuates a control or releases the handle.

In some aspects the proximal filter and the distal filter are both self-expanding. The proximal filter and the distal filter both may comprise an oblique truncated cone shape. Movement of the proximal sheath relative to the proximal filter causes the proximal filter to expand and deploy against the inside wall of a first vessel. The distal filter is then advanced through or adjacent to the distal shaft and distal articulatable sheath into expanding engagement against the inner wall of a second vessel. In some embodiments, a tethering member extends from the proximal sheath to the proximal filter to help draw the proximal filter opening toward the first vessel wall.

Another aspect of the disclosure is a single filter embolic protection device comprising a single filter device comprising a sheath, a filter shaft, and a filter assembly. In some aspects, the filter assembly is designed to accommodate a catheter-based device passing between the filter and the vessel wall. In certain embodiments, the filter assembly may include a channel, a gap, or an inflatable annulus. The filter assembly may also include one or more filter lobes. In another embodiment, the filter assembly may resemble an umbrella having a plurality of tines and a filter element connecting each tine. The filter assembly may alternatively include a plurality of overlapping filter portions, wherein a catheter may pass between a first filter portion and a second filter portion of the filter assembly.

BRIEF DESCRIPTION OF THE DRAWINGS

FIGS. 1A-1D illustrate an exemplary dual filter system.

FIGS. 6A and 6B illustrate an exemplary embodiment of an articulating distal sheath.

FIGS. 7A-7C illustrate a portion of an exemplary filter system.

FIGS. 8A-8C illustrate an exemplary pull wire.

FIGS. 9A-9C show an exemplary embodiment of a distal sheath with slots formed therein.

FIGS. 9D-9E show an exemplary embodiment of a distal sheath capable of deflecting in multiple directions.

FIGS. 10A and 10B illustrate a portion of exemplary distal sheath adapted to be multi-directional.

FIGS. 13A and 13B illustrate alternative distal sheath and distal shaft portions of an exemplary filter system.

FIG. 14 illustrates a portion of an exemplary system including a distal shaft and a distal sheath.

FIGS. 19A-19C, 20A-20B, 21, 22A-B illustrate exemplary proximal filters.

FIGS. 26A-26G illustrate an exemplary method of preparing an exemplary distal filter assembly for use.

FIGS. 28A-28E illustrate an exemplary distal filter assembly in collapsed and expanded configurations.

FIGS. 29A-29E illustrate a portion of an exemplary filter system with a lower delivery and insertion profile.

FIGS. 30A and 30B illustrate a portion of an exemplary filter system.

FIGS. 31A-31C illustrate an exemplary over-the-wire routing system that includes a separate distal port for a dedicated guidewire.

FIGS. 39A-C illustrate an aortic filter system having multiple aortic filters.

FIGS. 40A-B exemplify multiple embodiments for an aortic filter.

DETAILED DESCRIPTION OF THE PREFERRED EMBODIMENT

Figure 1:
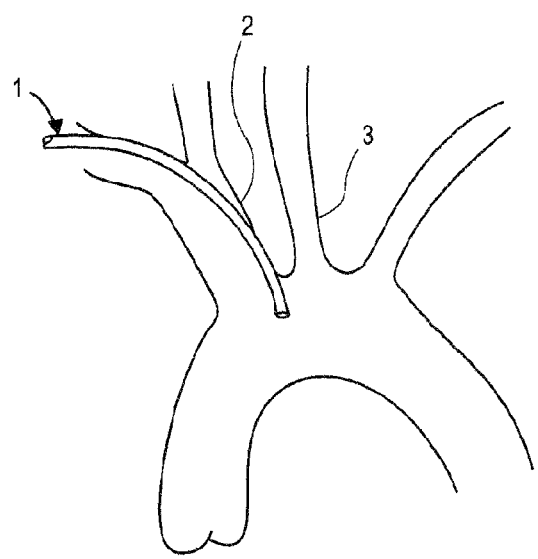
FIG. 1 illustrates an exemplary prior art catheter being advanced through a portion of a subject's vasculature.

Although certain preferred embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process can be performed in any suitable sequence and are not necessarily limited to any particular disclosed sequence. Various operations can be described as multiple discrete operations in turn, in a manner that can be helpful in understanding certain embodiments; however, the order of description should not be construed to imply that these operations are order dependent. Additionally, the structures described herein can be embodied as integrated components or as separate components. For purposes of comparing various embodiments, certain aspects and advantages of these embodiments are described. Not necessarily all such aspects or advantages are achieved by any particular embodiment. Thus, for example, various embodiments can be carried out in a manner that achieves or optimizes one advantage or group of advantages as taught herein without necessarily achieving other aspects or advantages as can also be taught or suggested herein.

The disclosure relates generally to intravascular blood filters used to capture foreign particles. In some embodiments the blood filter is a dual-filter system to trap foreign bodies to prevent them from traveling into the subject's right and left common carotid arteries, while in other embodiments, the blood filter is a single filter system. The filter systems described herein can, however, be used to trap particles in other blood vessels within a subject, and they can also be used outside of the vasculature. The systems described herein are generally adapted to be delivered percutaneously to a target location within a subject, but they can be delivered in any suitable way, and need not be limited to minimally-invasive procedures.

Filter systems in accordance with the present invention can be utilized to reduce the occurrence of emboli entering the cerebral circulation as a consequence of any of a variety of intravascular interventions, including, but not limited to, transcatheter aortic-valve implantation (TAVI), surgical valve repair or replacement, atrial fibrillation ablation, cardiac bypass surgery, or transthoracic graft placement around the aortic arch. For example, the present filter or filters may be placed as described elsewhere herein prior to a minimally invasive or open surgical repair or replacement of a heart valve, such as the mitral or aortic valve. The filter system may alternatively be placed prior to cardiac ablation such as ablation of the pulmonary vein to treat atrial fibrillation. Ablation may be accomplished using any of a variety of energy modalities, such as RF energy, cryo, microwave or ultrasound, delivered via a catheter having a distal end positioned within the heart. The present filter systems may alternatively be placed prior to cardiac bypass surgery, or prior to transthoracic graft placement around the aortic arch, or any of a variety of other surgeries or interventions that are accompanied by a risk of cerebral embolization.

In one application, the filter systems described herein are used to protect the cerebral vasculature against embolisms and other foreign bodies entering the bloodstream during a cardiac valve replacement or repair procedure. To protect both the right common carotid artery and the left common carotid artery during such procedures, the system described herein enters the aorta from the brachiocephalic artery. Once in the aortic space, there is a need to immediately navigate a 180 degree turn into the left common carotid artery. In gaining entry into the aorta from the brachiocephalic artery, use of prior art catheter devices 1 will tend to hug the outer edge of the vessel 2, as shown in FIG. 1. To then gain access to the left common carotid artery 3 with such prior art devices can be a difficult maneuver due to the close proximity of the two vessels which may parallel one another, often within 1 cm of separation, as shown in, for example, FIGS. 1-5. This sharp turn requires a very small radius and may tend to kink the catheter reducing or eliminating a through lumen to advance accessories such as guidewires, filters, stents, and other interventional tools. The catheter-based filter systems described herein can traverse this rather abrupt essentially 180 degree turn to thereby deploy filters to protect both the right and left common carotid arteries.

Figure 1A:
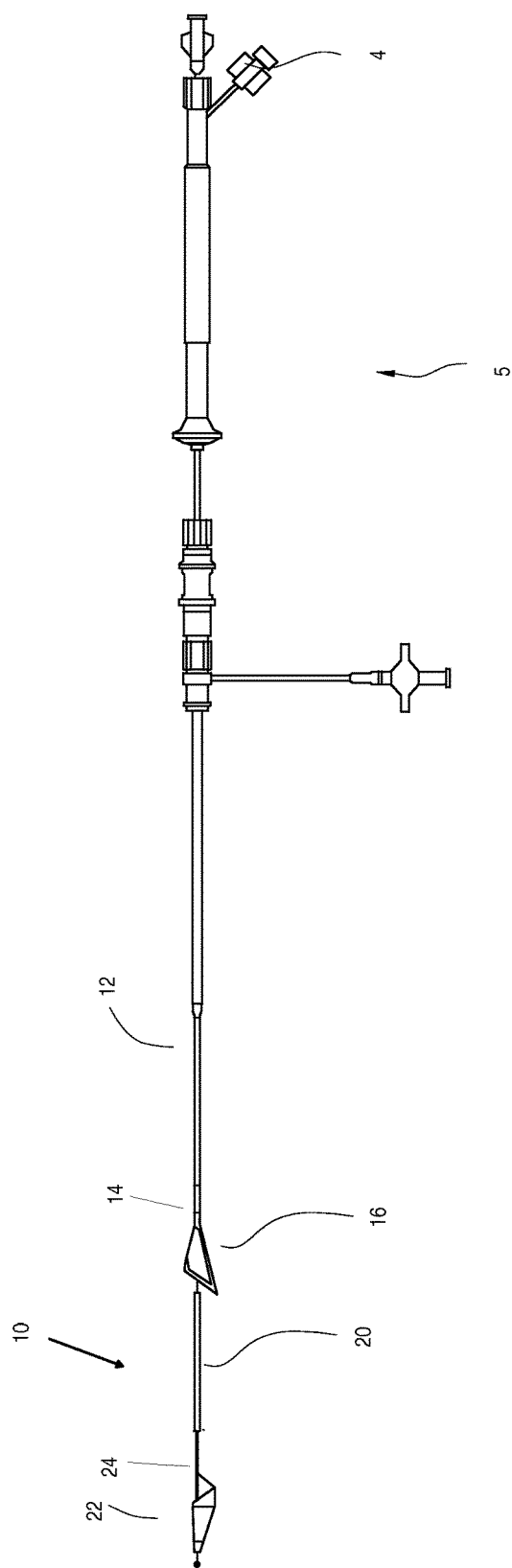

FIGS. 1A-1C illustrate an exemplary filter system having control handle portion 5 and filter system 10. In some embodiments, control handle portion 5 may include a distal flush port 4. Filter system 10 includes proximal sheath 12, proximal shaft 14 coupled to expandable proximal filter 16, distal shaft 18 coupled to distal articulatable sheath 20, distal filter 22, and guiding member 24. FIG. 1B illustrates proximal filter 16 and distal filter 22 in expanded configurations. FIG. 1C illustrates the system in a delivery configuration, in which proximal filter 16 (not seen in FIG. 1C) is in a collapsed configuration constrained within proximal sheath 12, while distal filter 22 is in a collapsed configuration constrained within distal articulatable sheath 20.

Figure 1D:
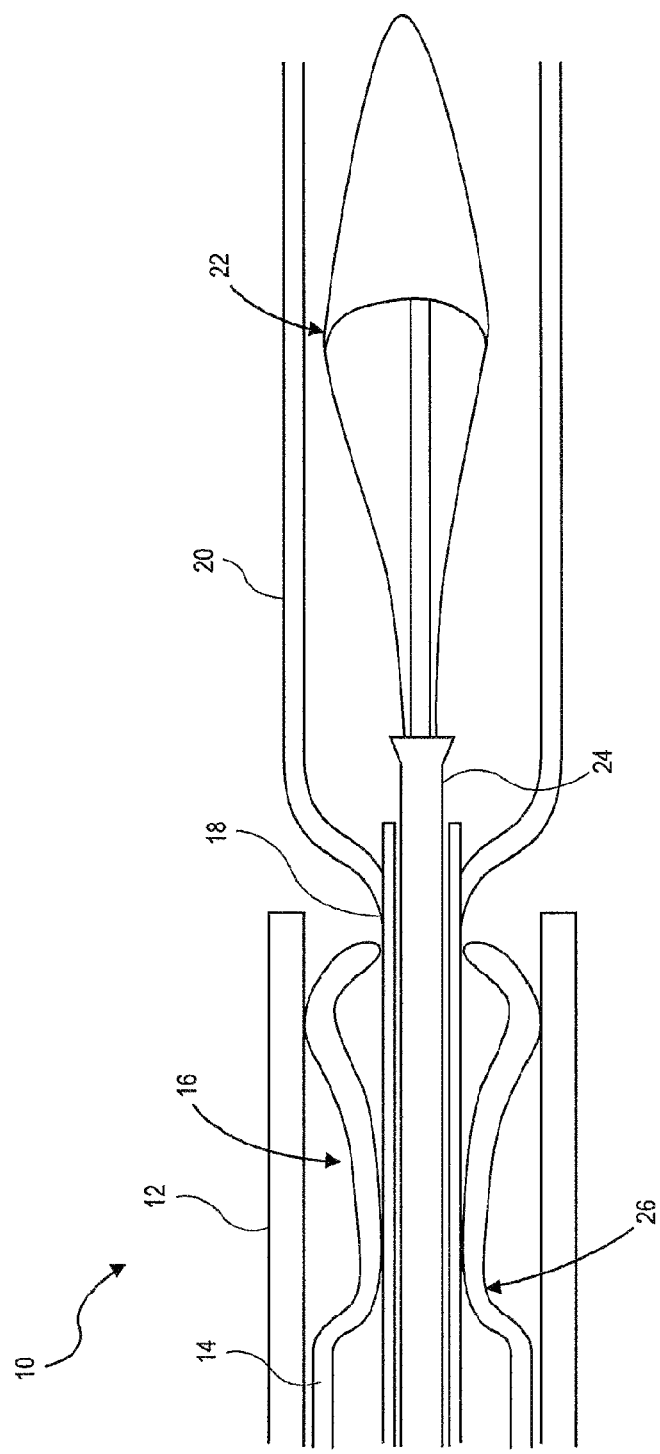

FIG. 1D is a sectional view of partial system 10 from FIG. 1C. Proximal shaft 14 is co-axial with proximal sheath 12, and proximal region 26 of proximal filter 16 is secured to proximal shaft 14. In its collapsed configuration, proximal filter 16 is disposed within proximal sheath 12 and is disposed distally relative to proximal shaft 14. Proximal sheath 12 is axially (distally and proximally) movable relative to proximal shaft 14 and proximal filter 16. System 10 also includes distal sheath 20 secured to a distal region of distal shaft 18. Distal shaft 18 is co-axial with proximal shaft 14 and proximal sheath 12. Distal sheath 20 and distal shaft 18, secured to one another, are axially movable relative to proximal sheath 12, proximal shaft 14 and proximal filter 16. System 10 also includes distal filter 22 carried by guiding member 24. In FIG. 1D distal filter 22 is in a collapsed configuration within distal sheath 22. Guiding member 24 is coaxial with distal sheath 20 and distal shaft 18 as well as proximal sheath 12 and proximal shaft 14. Guiding member 24 is axially movable relative to distal sheath 20 and distal shaft 18 as well as proximal sheath 12 and proximal shaft 14. Proximal sheath 12, distal sheath 20, and guiding member 24 are each adapted to be independently moved axially relative to one other. That is, proximal sheath 12, distal sheath 20, and guiding member 24 are adapted for independent axial translation relative to each of the other two components.

In the embodiments in FIGS. 1A-1F, proximal filter 16 includes support element or frame 15 and filter element 17, while distal filter 22 includes support element 21 and filter element 23. The support elements generally provide expansion support to the filter elements in their respective expanded configurations, while the filter elements are adapted to filter fluid, such as blood, and trap particles flowing therethrough. The expansion supports are adapted to engage the wall of the lumen in which they are expanded. The filter elements have pores therein that are sized to allow the blood to flow therethrough, but are small enough to prevent unwanted foreign particles from passing therethrough. The foreign particles are therefore trapped by and within the filter elements.

Figure 1E:
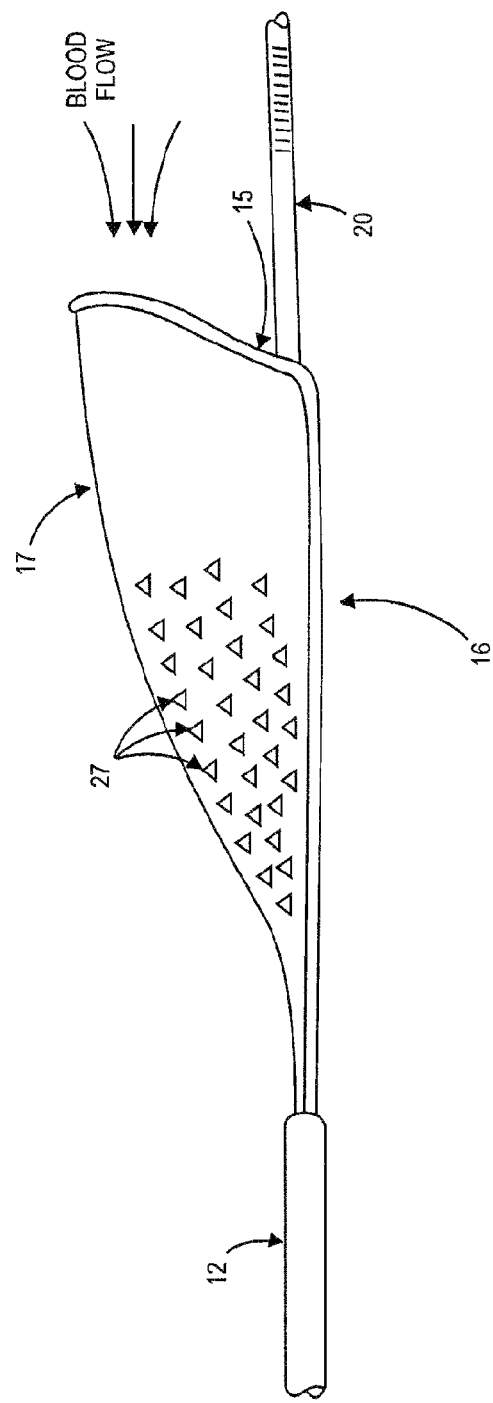
FIGS. 1E and 1F illustrate exemplary proximal filters.
Figure 1F:
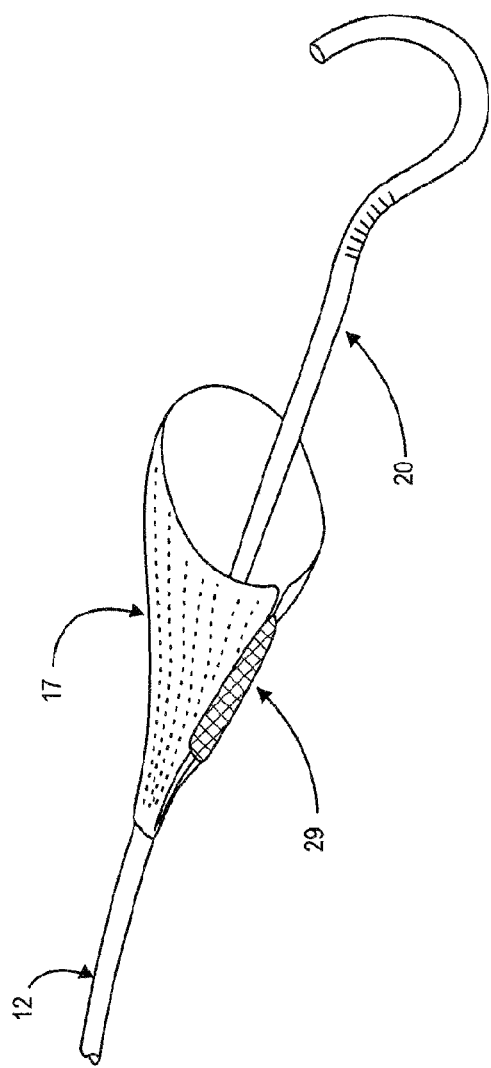

In one embodiment, filter element 17 is formed of a polyurethane film mounted to frame 15, as shown in FIGS. 1E and 1F. Film element 17 can measure about 0.0001 inches to about 0.1 inches in thickness. In some embodiments, the film thickness measures between 0.005 and 0.05, or between 0.015 and 0.025. In some situations, it may be desirable to have a filter with a thickness less than 0.0001 or greater than 0.1 inches. Other polymers may also be used to form the filter element, in the form of a perforated sheet or woven or braided membranes. Thin membranes or woven filament filter elements may alternatively comprise metal or metal alloys, such as nitinol, stainless steel, etc.

Filter element 17 has through holes 27 to allow fluid to pass and will resist the passage of the embolic material within the fluid. These holes can be circular, square, triangular or other geometric shapes. In the embodiment as shown in FIG. 1E, an equilateral triangular shape would restrict a part larger than an inscribed circle but have an area for fluid flow nearly twice as large making the shape more efficient in filtration verses fluid volume. It is understood that similar shapes such as squares and slots would provide a similar geometric advantage. In certain embodiments, the filter holes are laser drilled into the filter membrane, but other methods can be used to achieve a similar result. In some embodiments filter holes 27 are between about 1 micron and 1000 microns (1 mm). In certain embodiments, the hole size is between 1 micron and 500 microns. In other embodiments, the hole size is between 50 microns and 150 microns. However, the hole size can be larger, depending on the location of the filter within the subject and the type of particulate sought to be trapped in the filter.

In several embodiments, frame element 15 can be constructed of a shape memory material such as Nitinol, or other materials such as stainless steel or cobalt super alloy (MP35N for example) that have suitable material properties. Frame element 15 could take the form of a round wire or could also be of a rectangular or elliptical shape to preserve a smaller delivery profile. In one such embodiment, frame element 15 comprises Nitinol wire where the hoop is created from a straight piece of wire and shape set into a frame where two straight legs run longitudinally along the delivery system and create a circular distal portion onto which the filter film will be mounted. The circular or loop portion may include a radiopaque marker such as a small coil of gold, platinum iridium, or other radiopaque marker for visualization under fluoroscopy. In other embodiments, the frame element may not comprise a hoop, but include a spinal element disposed across a longitudinal length of the filter element. In still other embodiments, the filter element may not include a frame element.

The shape of the filter opening or frame elements 15, 17 may take a circular shape when viewed axially or other shape that apposes the vessel wall. In some embodiments, such as those illustrated in FIGS. 1E, 1F and 25D, the shape of frame element 15 and filter element 17 are of an oblique truncated cone having a non-uniform or unequal length around and along the length of the conical filter 16. In such a configuration, much like a windsock, the filter 16 would have a larger opening (upstream) diameter and a reduced ending (downstream) diameter. The unconstrained, fully expanded filter diameter can measure between 3 mm and 30 mm, but in some embodiments, the diameter may be less than 3 mm or greater than 30 mm. In some embodiments, the diameter may range between 10-25 mm or between 15-20 mm. The length of the filter may range between 10 mm and 50 mm, but the length of the filter may be less than 10 mm or greater than 50 mm. In some embodiments, the length may range between 10 mm and 30 mm or between 30 mm and 50 mm. In one embodiment, the diameter of the filter opening could measure about 15-20 mm in diameter and have a length of about 30-50 mm. A selection of different filter sizes would allow treatment of a selection of patients having different vessel sizes.

In some embodiments the material of the filter element is a smooth and/or textured surface that is folded or contracted into a small delivery catheter by means of tension or compression into a lumen. A reinforcement fabric 29, as shown in FIG. 1F, may be added to or embedded in the filter to accommodate stresses placed on the filter material by means of the tension or compression applied. This will also reduce the stretching that may occur during delivery and retraction of filter element 17. This reinforcement material 29 could be a polymer or metallic weave to add additional localized strength. This material could be imbedded into the polyurethane film to reduce its thickness. In one particular embodiment, this imbedded material could be a polyester weave mounted to a portion of the filter near the longitudinal frame elements where the tensile forces act upon the frame and filter material to expose and retract the filter from its delivery system. In some embodiments, the film measures between 0.0005 and 0.05, between 0.0025 and 0.025, or between 0.0015 and 0.0025 inches thick. In certain embodiments, the thickness is between 0.015 and 0.025 inches. In some situations, it may be desirable to have a filter with a thickness less than 0.0001 or greater than 0.1 inches. In some embodiments, the reinforcement fabric has a pore size between about 1 micron and about 1000 microns. In certain embodiments, the pore size is between about 50 microns and about 150 microns. While such an embodiment of the filter elements has been described for convenience with reference to proximal filter element 17, it is understood that distal filter element 23 could similarly take such form or forms.

As shown in FIG. 1B, proximal filter 16 has a generally distally-facing opening 13, and distal filter 22 has a generally proximally-facing opening 19. The filters can be thought of as facing opposite directions. As described in more detail below, the distal sheath is adapted to be steered, or bent, relative to the proximal sheath and the proximal filter. As the distal sheath is steered, the relative directions in which the openings face will be adjusted. Regardless of the degree to which the distal sheath is steered, the filters are still considered to having openings facing opposite directions. For example, the distal sheath could be steered to have a 180 degree bend, in which case the filters would have openings facing in substantially the same direction. The directions of the filter openings are therefore described if the system were to assume a substantially straightened configuration, an example of which is shown in FIG. 1B. Proximal filter element 17 tapers down in the proximal direction from support element 15, while distal filter element 23 tapers down in the distal direction from support element 21. A fluid, such as blood, flows through the opening and passes through the pores in the filter elements, while the filter elements are adapted to trap foreign particles therein and prevent their passage to a location downstream to the filters.

In several embodiments, the filters are secured to separate system components. In the embodiment in FIGS. 1A-1D, for example, proximal filter 16 is secured to proximal shaft 14, while distal filter 22 is secured to guiding member 24. In FIGS. 1A-1D, the filters are secured to independently-actuatable components. This allows the filters to be independently positioned and controlled. Additionally, the filters are collapsed within two different tubular members in their collapsed configurations. In the embodiment in FIGS. 1A-1D, for example, proximal filter 16 is collapsed within proximal sheath 12, while distal filter 22 is collapsed within distal sheath 20. In the system's delivery configuration, the filters are axially-spaced from one another; however, in an alternative embodiment, the filters may be positioned such that a first filter is located within a second filter. For example, in FIG. 1D, distal filter 22 is distally-spaced relative to proximal filter 16.

In some embodiments the distal sheath and the proximal sheath have substantially the same outer diameter (see, e.g., FIGS. 1C and 1D). When the filters are collapsed within the sheaths, the sheath portion of the system therefore has a substantially constant outer diameter, which can ease the delivery of the system through the patient's body and increase the safety of the delivery. In FIG. 1D, distal and proximal sheaths 20 and 12 have substantially the same outer diameter, both of which have larger outer diameters than the proximal shaft 14. Proximal shaft 14 has a larger outer diameter than distal shaft 18, wherein distal shaft 18 is disposed within proximal shaft 14. Guiding member 24 has a smaller diameter than distal shaft 18. In some embodiments the proximal and distal sheaths have an outer diameter between 3 French (F) and 14 F. In certain embodiments, the outer diameter is between 4 F and 8 F. In still other embodiments, the outer diameter is between 4 F and 6 F. In some embodiments the sheaths have different outer diameters. For example, the proximal sheath can have a size of 6 F, while the distal sheath has a size of 5 F. In an alternate embodiment the proximal sheath is 5 F and the distal sheath is 4 F. A distal sheath with a smaller outer diameter than the proximal sheath reduces the delivery profile of the system and can ease delivery. In some methods of use, the filter system is advanced into the subject through an incision made in the subject's right radial artery. In a variety of medical procedures a medical instrument is advanced through a subject's femoral artery, which is larger than the right radial artery. A delivery catheter used in femoral artery access procedures has a larger outer diameter than would be allowed in a filter system advanced through a radial artery. Additionally, in some uses the filter system is advanced from the right radial artery into the aorta via the brachiocephalic trunk. The radial artery has the smallest diameter of the vessels through which the system is advanced. The radial artery therefore limits the size of the system that can be advanced into the subject when the radial artery is the access point. The outer diameters of the systems described herein, when advanced into the subject via a radial artery, are therefore smaller than the outer diameters of the guiding catheters (or sheaths) typically used when access is gained via a femoral artery.

FIG. 6A illustrates a portion of a filter delivery system in a delivery configuration. The system's delivery configuration generally refers to the configuration when both filters are in collapsed configurations within the system. FIG. 6B illustrates that the distal articulating sheath is independently movable with 3 degrees of freedom relative to the proximal sheath and proximal filter. In FIG. 6A, proximal sheath 60 and distal sheath 62 are coupled together at coupling 61. Coupling 61 can be a variety of mechanisms to couple proximal sheath 60 to distal sheath 62. For example, coupling 61 can be an interference fit, a friction fit, a spline fitting, end to end butt fit or any other type of suitable coupling between the two sheaths. When coupled together, as shown in FIG. 6A, the components shown in FIG. 6B move as a unit. For example, proximal sheath 60, proximal shaft 64, proximal filter 66, distal shaft 68, and the distal filter (not shown but within distal sheath 62) will rotate and translate axially (in the proximal or distal direction) as a unit. When proximal sheath 60 is retracted to allow proximal filter 66 to expand, as shown in FIG. 6B, distal sheath 62 can be independently rotated ("R"), steered ("S"), or translated axially ("T") (either in the proximal "P" direction or distal "D" direction). The distal sheath therefore has 3 independent degrees of freedom: axial translation, rotation, and steering. The adaptation to have 3 independent degrees of freedom is advantageous when positioning the distal sheath in a target location, details of which are described below.

Figure 2B:
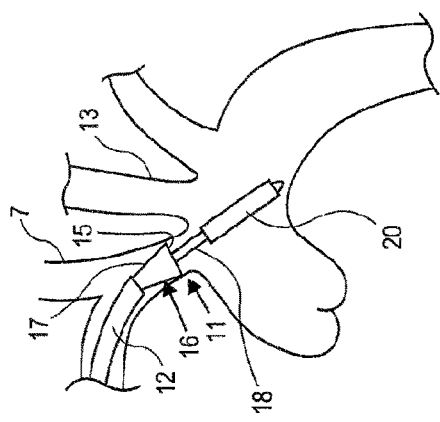
FIGS. 2A-2D illustrate an exemplary method of delivering and deploying a dual filter system
Figure 2D:
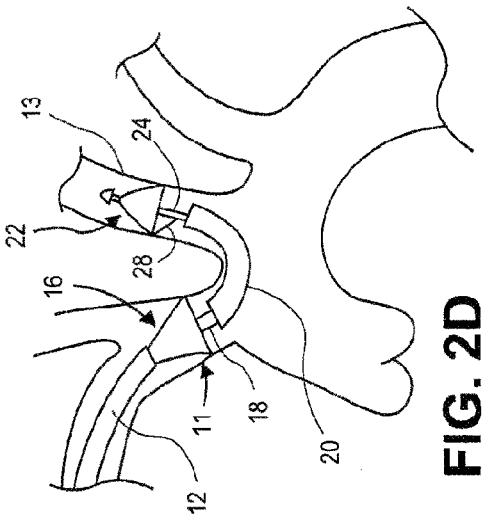
Figure 2A:
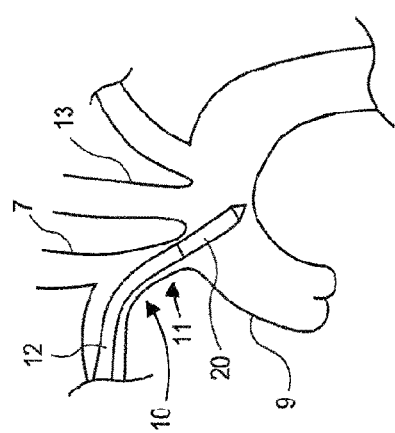

FIGS. 2A-2D illustrate a merely exemplary embodiment of a method of using any of the filter systems described herein. System 10 from FIGS. 1A-1D is shown in the embodiment in FIGS. 2A-2D. System 10 is advanced into the subject's right radial artery through an incision in the right arm. The system is advanced through the right subclavian artery and into the brachiocephalic trunk 11, and a portion of the system is positioned within aorta 9 as can be seen in FIG. 2A (although that which is shown in FIG. 2A is not intended to be limiting).

Proximal sheath 12 is retracted proximally to allow proximal filter support element 15 to expand to an expanded configuration against the wall of the brachiocephalic trunk 11, as is shown in FIG. 2B. Proximal filter element 17 is secured either directly or indirectly to support element 15, and is therefore reconfigured to the configuration shown in FIG. 2B. The position of distal sheath 20 can be substantially maintained while proximal sheath 12 is retracted proximally. Once expanded, the proximal filter filters blood traveling through the brachiocephalic artery 11, and therefore filters blood traveling into the right common carotid artery 7. The expanded proximal filter is therefore in position to prevent foreign particles from traveling into the right common carotid artery 7 and into the cerebral vasculature.

Figure 2C:
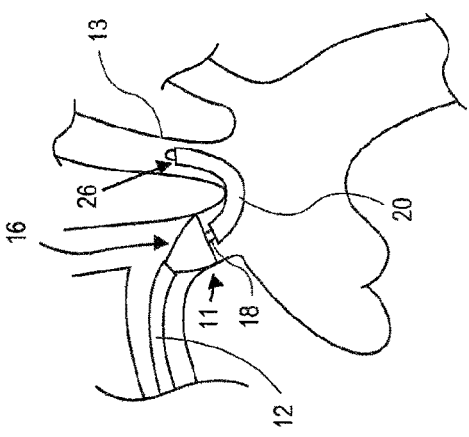

Distal sheath 20 is then steered, or bent, and distal end 26 of distal sheath 20 is advanced into the left common carotid artery 13, as shown in FIG. 2C. Guiding member 24 is thereafter advanced distally relative to distal sheath 20, allowing the distal support element to expand from a collapsed configuration to a deployed configuration against the wall of the left common carotid artery 13 as shown in FIG. 2D. The distal filter element is also reconfigured into the configuration shown in FIG. 2D. Once expanded, the distal filter filters blood traveling through the left common carotid artery 13. The distal filter is therefore in position to trap foreign particles and prevent them from traveling into the cerebral vasculature.

In several embodiments, the proximal and distal filter elements or frame elements comprise elastic or shape memory material causing the filters to expand as they exit their respective sheaths. In other embodiments, mechanical or hydraulic mechanisms may be used to expand each filter element. Once the filters are in place and expanded, an optional medical procedure can then take place, such as a valvuloplasty and/or replacement heart valve procedure. Any plaque or thrombus dislodged during the heart valve procedure that enters into the brachiocephalic trunk or the left common carotid artery will be trapped in the filters.

The filter system can thereafter be removed from the subject (or at any point in the procedure). In an exemplary embodiment, distal filter 22 is first retrieved back within distal sheath 20 to the collapsed configuration. To do this, guiding member 24 is retracted proximally relative to distal sheath 20. This relative axial movement causes distal sheath 20 to engage strut 28 and begin to move strut 28 towards guiding member 24. Support element 21, which is coupled to strut 28, begins to collapse upon the collapse of strut 28. Filter element 23 therefore begins to collapse as well. Continued relative axial movement between guiding member 24 and distal sheath 20 continues to collapse strut 28, support element 21, and filter element 23 until distal filter 22 is retrieved and re-collapsed back within distal sheath 20 (as shown in FIG. 2C). Any foreign particles trapped within distal filter element 23 are contained therein as the distal filter is re-sheathed. Distal sheath 20 is then steered into the configuration shown in FIG. 2B, and proximal sheath is then advanced distally relative to proximal filter 16. This causes proximal filter 16 to collapse around distal shaft 18, trapping any particles within the collapsed proximal filter. Proximal sheath 12 continues to be moved distally towards distal sheath 20 until in the position shown in FIG. 2A. The entire system 10 can then be removed from the subject.

In any of the embodiments mentioned herein, the filter or filters may alternatively be detached from the delivery catheter, and the delivery catheter removed leaving the filter behind. The filter or filters can be left in place permanently, or retrieved by snaring it with a retrieval catheter following a post procedure treatment period of time. Alternatively, the filters may remain attached to the catheter, and the catheter may be left in place post procedure for the treatment period of time. That treatment period may be at least one day, one week, three weeks, five weeks or more, depending upon the clinical circumstances. Patients with an indwelling filter or filters may be administered any of a variety of thrombolytic or anticoagulant therapies, including tissue plasminogen activator, streptokinase, coumadin, heparin and others known in the art.

An exemplary advantage of the systems described herein is that the delivery and retrieval system are integrated into the same catheter that stays in place during the procedure. Unloading and loading of different catheters, sheaths, or other components is therefore unnecessary. Having a system that performs both delivery and retrieval functions also reduces procedural complexity, time, and fluoroscopy exposure time. In addition, only a minimal portion of the catheter is in the aortic arch, thus greatly reducing the change of interference with other catheters.

FIGS. 7A-7B illustrate a perspective view and sectional view, respectively, of a portion of an exemplary filter system. The system includes distal shaft 30 and distal articulatable sheath 34, coupled via coupler 32. FIG. 7B shows the sectional view of plane A. Distal sheath 34 includes steering element 38 extending down the length of the sheath and within the sheath, which is shown as a pull wire. The pull wire can be, for example without limitation, stainless steel, tungsten, alloys of cobalt such as MP35N®, or any type of cable, either comprised of a single strand or two or more strands. Distal sheath 34 also includes spine element 36, which is shown extending down the length of the sheath on substantially the opposite side of the sheath from steering element 38. Spine element 36 can be, for example without limitation, a ribbon or round wire. Spine element 36 can be made from, for example, stainless steel or Nitinol. Spine element 36 resists axial expansion or compression of articulatable sheath 34 upon the application of an actuating axial pull or push force applied to steering element 38, allowing sheath 34 to be deflected toward configuration 40, as shown in phantom in FIG. 7A. FIG. 7C shows an alternative embodiment in which distal sheath 33 has a non-circular cross section. Also shown are spine element 35 and steering element 37.

FIGS. 8A-8C illustrate views of exemplary pull wire 42 that can be incorporated into any distal sheaths described herein. Plane B in FIG. 8B shows a substantially circular cross-sectional shape of pull wire 42 in a proximal portion 44 of the pull wire, while plane C in FIG. 8C shows a flattened cross-sectional shape of distal portion 46. Distal portion 46 has a greater width than height. The flattened cross-sectional shape of distal portion 46 provides for an improved profile, flexibility, and resistance to plastic deformation, which provides for improved straightening.

Figure 9B:
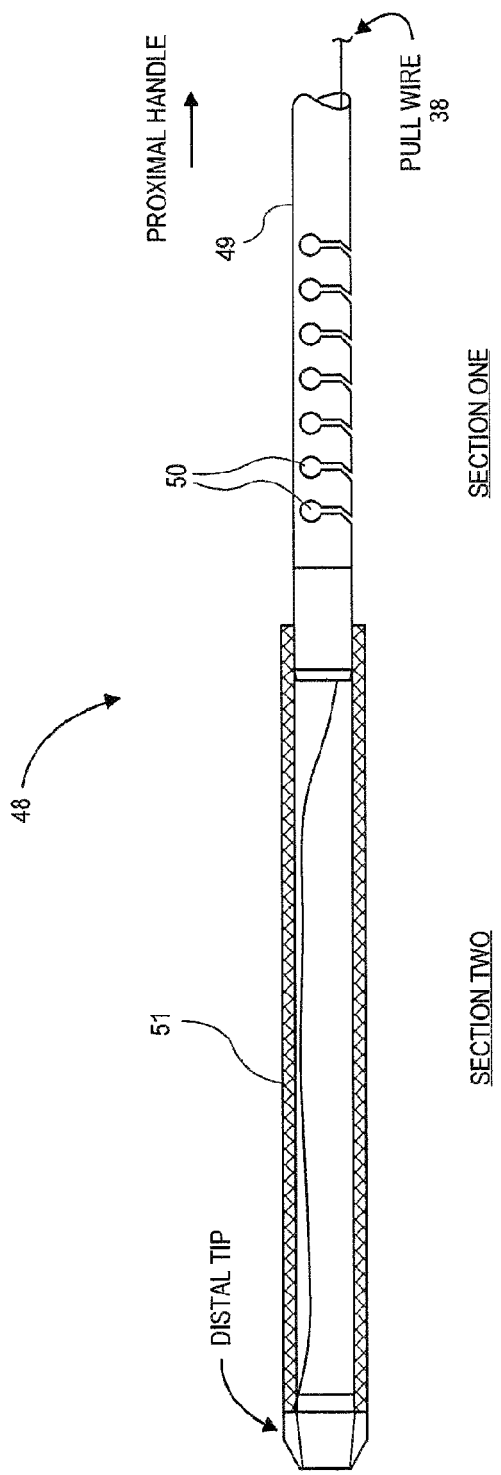
Figure 9C:
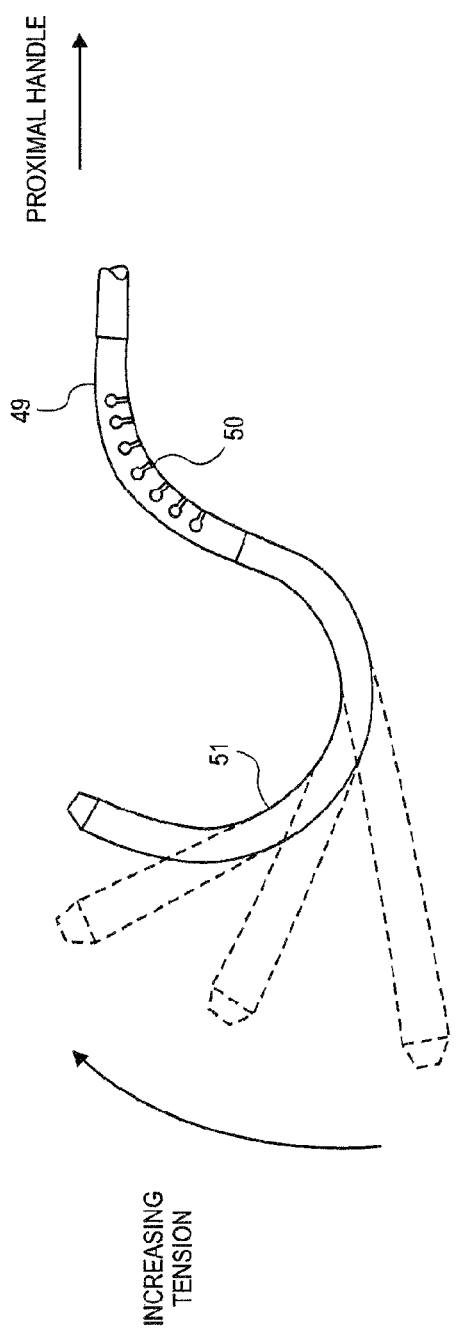

FIGS. 9A-C show an alternative embodiment of distal sheath 48 that includes slots 50 formed therein. The slots can be formed by, for example, grinding, laser cutting or other suitable material removal from distal sheath 48. Alternatively, the slots can be the openings between spaced apart coils or filars of a spring. The characteristics of the slots can be varied to control the properties of the distal sheath. For example, the pitch, width, depth, etc., of the slots can be modified to control the flexibility, compressibility, torsional responsiveness, etc., of distal sheath 48. More specifically, the distal sheath 48 can be formed from a length of stainless steel hypotubing. Transverse slots 50 are preferably formed on one side of the hypotubing, leaving an opposing spine which provides column strength to avoid axial compression or expansion upon application of an axial force to the pull wire and also limits deflection to a desired single plane or predetermined planes.

FIG. 9B shows a further embodiment of the distal sheath in greater detail. In this embodiment distal sheath 48 includes a first proximal articulatable hypotube section 49. Articulatable hypotube section 49 is fixed to distal shaft 30 (not shown in FIG. 9A). A second distal articulatable section 51 is secured to first proximal section 49. Pull wire 38 extends from the handle through distal shaft section 49 and is affixed to a distal portion of distal shaft portion 51. This embodiment allows for initial curvature of distal sheath proximal section 49 in a first direction such as away from the outer vessel wall in response to proximal retraction of the pull wire 38. Distal sheath distal section 51 is then articulated to a second curvature in a second, opposite direction. This second curvature of distal shaft section 51 is adjustable based upon tension or compression loading of the sheath section by pull wire 38. Alternatively, a first pull wire can be attached at a distal portion of section 49 and a second pull wire can be attached at a distal portion of section 51 to allow independent deflection of the two deflection sections.

As shown in FIG. 9B, pull wire 38 in a single pull wire embodiment crosses to an opposite side of the inner lumen defined by sections 49 and 51 from the slots 50 as it transitions from the first distal sheath proximal section 49 to second distal sheath distal section 51. As best shown in FIG. 9C, distal sheath proximal section 49 would articulate first to initialize a first curve, concave in a first direction as the slots 50 compress in response to proximal retraction of the pull wire 38. As the tension on pull wire 38 is increased and the slots bottom out, distal sheath distal section 51 begins to form a second curve concave in a second direction opposite to the direction of the first curve, due to pull wire 38 crossing the inner diameter of the lumen through distal sheath sections 49 and 51. As can be seen in FIG. 9C, as it nears and comes to the maximum extent of its articulation, distal sheath distal section 51 can take the form of a shepherd's staff or crook.

Distal sheath proximal section 49 could take the form of a tubular slotted element or a pre-shaped curve that utilizes a memory material such as Nitinol or any other material exhibiting suitable properties. In some embodiments outer diameter of distal sheath proximal section 49 is between 0.02 inches and 0.2 inches. In certain embodiments, the outer diameter is between 0.05 inches and 0.1 inches, or between 0.06 inches and 0.075 inches. In some embodiments, the inner diameter of distal sheath proximal section 49 is between 0.02 inches and 0.2 inches. In certain embodiments, the inner diameter is between 0.03 inches and 0.08 inches or between 0.05 inches and 0.07 inches. In several embodiments, the length of distal sheath proximal section 49 may measures between 0.1 inches and 2.5 inches. In some embodiments, the length of distal sheath proximal section 49 may measure between about 0.50 inches and 1 inch or between 0.6 inches and 0.8 inches. In certain embodiments, the length of distal sheath proximal section 49 may be longer than 2.5 inches. It is understood that these sizes and proportions will vary depending on the specific application and those listed herein are not intended to be limiting. Transverse slots 50 can measure from about 0.002 inches to about 0.020 inches in width (measured in the axial direction) depending on the specific application and the degree of curvature desired. In some embodiments the slots can measure less than 0.002 inches or greater than 0.02 inches. In certain embodiments, the slots 50 can measure about 0.002 inches to 0.01 inches or between 0.006 and 0.01 inches.

The curvature of proximal section 49 may be varied from about 0 degrees to 90 degrees or more depending on the width and number of the slots 50. In several embodiments, the maximum degree of deflection ranges from about 15 degrees to about 75 degrees, from about 45 degrees to about 60 degrees. Commencement of deflection of distal section 51 can occur prior to, simultaneously with or following commencement of deflection of proximal section 49 based upon the relative stiffness of the sections or configuration of the pull wire as will be apparent to those of skill in the art.

The distal sheath is configured such that the maximum net curvature between the primary axis of the catheter prior to any deflection and the distal tip axis is between about 90 and about 220 degrees. In other embodiments, the maximum deflection is between about 120 degrees and about 200 degrees, or between about 150 degrees and about 180 degrees. When the distal sheath is in its curved configuration, with a net deflection from the primary axis of at least about 150 degrees, the lateral distance between the primary axis and the distal tip ranges from about 5 mm to about 15 mm.

The position of at least a second group of slots 50 may also be rotationally displaced about the axis of the tube with respect to a first group of slots to allow a first portion of the distal sheath to bend in a first plane and a second portion of the distal sheath to bend out-of-plane to access more complex anatomy as shown in FIGS. 9D and 9E. The second set of slots 50 may be displaced circumferentially from the first set of slots by about 5 degrees to about 90 degrees. In certain embodiments, the slots are displaced from about 15 to 60 degrees or from about 20 to about 40 degrees. The curvature of the out of plane curve may vary from about 20 degrees to about 75 degrees, but in some embodiments, the out of plane curvature may be less than 20 degrees or greater than 75 degrees. In several embodiments, the curvature of the out of plane curve is from about 20 degrees to 40 degrees, from about 30 degrees to about 50 degrees, from about 40 degrees to about 60 degrees, or from about 50 degrees to 75 degrees. Alternatively, this out-of-plane bend could be achieved by prebending the tube after laser cutting the slots to create a bias or by any other method which would create a bias. The shape could also be multi-plane or bidirectional where the tube would bend in multiple directions within the same section of laser cut tube.

In several embodiments, distal sheath distal section 51 is a selectable curve based upon the anatomy and vessel location relative to one another. This section 51 could also be a portion of the laser cut element or a separate construction where a flat ribbon braid could be utilized. It may also include a stiffening element or bias ribbon to resist permanent deformation. In one embodiment it would have a multitude of flat ribbons staggered in length to create a constant radius of curvature under increased loading.

Figure 9F:
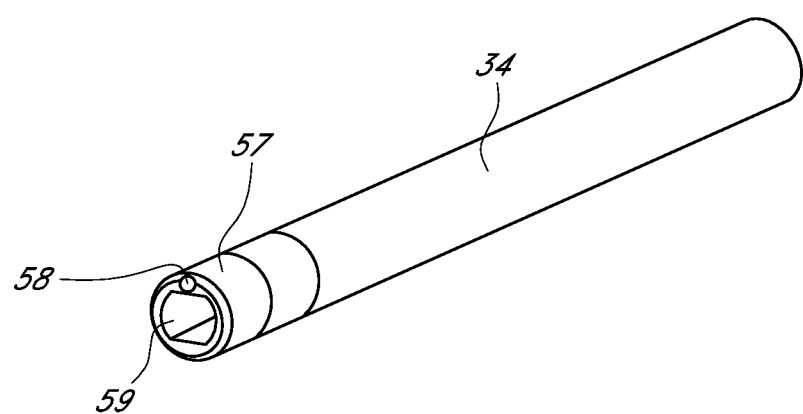
FIGS. 9F and 9G illustrate exemplary guidewire lumen locations in the distal sheath.
Figure 9G:
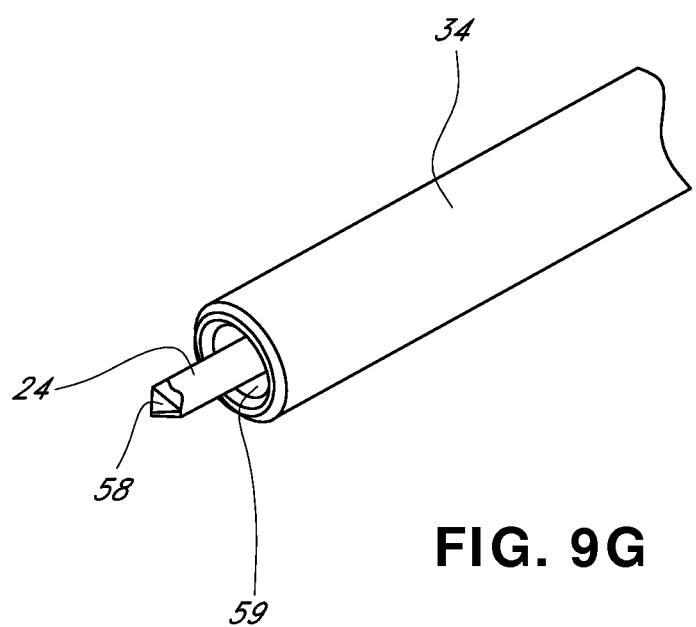

In some embodiments, distal sheath 34 incorporates a guidewire lumen 58 through which a guidewire may pass as shown in FIG. 9F. Alternatively, in FIG. 9G, the guidewire lumen is coaxial with guiding member lumen 59. Removing the guidewire lumen from the wall of distal sheath 34 has the added benefit of increasing the distal sheath luminal cross sectional area, reducing deployment and retrieval forces, and increasing the capacity for debris within the distal sheath.

FIGS. 10A and 10B illustrate a portion of exemplary distal sheath 52 that is adapted to be multi-directional, and is specifically shown to be bi-directional. Distal sheath 52 is adapted to be steered towards the configurations 53 and 54 shown in phantom in FIG. 10A. FIG. 10B is a sectional view in plane D, showing spinal element 55 and first and second steering elements 56 disposed on either side of spinal element 55. Steering elements 56 can be similar to steering element 38 shown in FIG. 7B. The steering elements can be disposed around the periphery of distal sheath at almost any location.

Incorporating steerable functionality into tubular devices is known in the area of medical devices. Any such features can be incorporated into the systems herein, and specifically into the articulatable distal sheaths.

In some embodiments the distal sheath includes radiopaque markers to visualize the distal sheath under fluoroscopy. In some embodiments the distal sheath has radiopaque markers at proximal and distal ends of the sheath to be able to visualize the ends of the sheath.

Figure 11A:
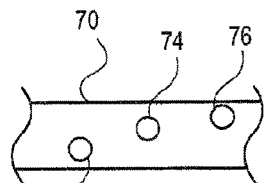
FIGS. 11A-11E illustrate merely exemplary anatomical variations that can exist.
Figure 11B:
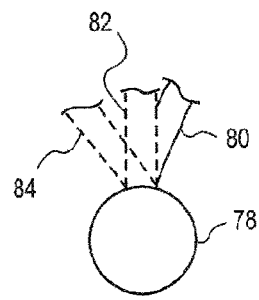
Figure 11C:
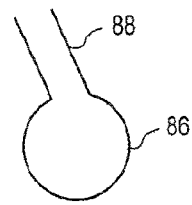
Figure 11D:
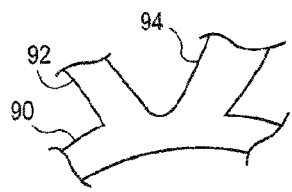
Figure 11E:
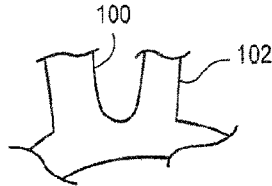

An exemplary advantage of the filter systems described herein is the ability to safely and effectively position the distal sheath. In some uses, the proximal filter is deployed in a first bodily lumen, and the distal filter is deployed in a second bodily lumen different than the first. For example, as shown in FIG. 2D, the proximal filter is deployed in the brachiocephalic trunk and the distal filter is deployed in a left common carotid artery. While both vessels extend from the aortic arch, the position of the vessel openings along the aortic arch varies from patient-to-patient. That is, the distance between the vessel openings can vary from patient to patient. Additionally, the angle at which the vessels are disposed relative to the aorta can vary from patient to patient. Additionally, the vessels do not necessarily lie within a common plane, although in many anatomical illustrations the vessels are typically shown this way. For example, FIGS. 11A-11C illustrate merely exemplary anatomical variations that can exist. FIG. 11A is a top view (i.e., in the superior-to-inferior direction) of aorta 70, showing relative positions of brachiocephalic trunk opening 72, left common carotid artery opening 74, and left subclavian opening 76. FIG. 11B is a side sectional view of aortic 78 illustrating the relative angles at which brachiocephalic trunk 80, left common carotid artery 82, and left subclavian artery 84 can extend from aorta 78. FIG. 11C is a side sectional view of aorta 86, showing vessel 88 extending from aorta 86 at an angle. Any or all of the vessels extending from aorta 86 could be oriented in this manner relative to the aorta. FIGS. 11D and 11E illustrate that the angle of the turn required upon exiting the brachiocephalic trunk 92/100 and entering the left common carotid artery 94/102 can vary from patient to patient. Due to the patient-to-patient variability between the position of the vessels and their relative orientations, a greater amount of control of the distal sheath increases the likelihood that the distal filter will be positioned safely and effectively. For example, a sheath that only has the ability to independently perform one or two of rotation, steering, and axial translation may not be adequately adapted to properly and safely position the distal filter in the left common carotid artery. All three degrees of independent motion as provided to the distal sheaths described herein provide important clinical advantages. Typically, but without intending to be limiting, a subject's brachiocephalic trunk and left carotid artery are spaced relatively close together and are either substantially parallel or tightly acute (see, e.g., FIG. 11E).

Figure 12A:
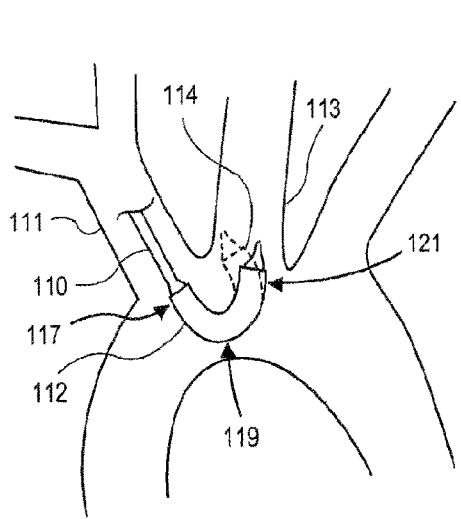
FIGS. 12A and 12B illustrate an exemplary curvature of a distal sheath to help position the distal filter properly in the left common carotid artery.
Figure 12B:
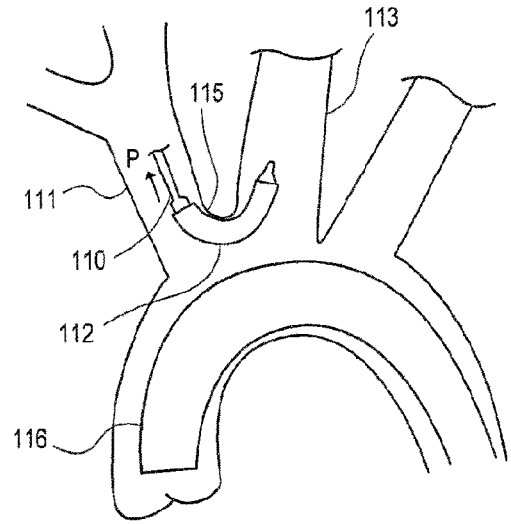

FIGS. 12A and 12B illustrates an exemplary curvature of a distal sheath to help position the distal filter properly in the left common carotid artery. In FIGS. 12A and 12B, only a portion of the system is shown for clarity, but it can be assumed that a proximal filter is included, and in this example has been expanded in brachiocephalic trunk 111. Distal shaft 110 is coupled to steerable distal sheath 112. Distal sheath 112 is steered into the configuration shown in FIG. 12B. The bend created in distal sheath 112, and therefore the relative orientations of distal sheath 112 and left common carotid artery 113, allow for the distal filter to be advanced from distal sheath 112 into a proper position in left common carotid 113. In contrast, the configuration of distal sheath 114 shown in phantom in FIG. 12A illustrates how a certain bend created in the distal sheath can orient the distal sheath in such a way that the distal filter will be advanced directly into the wall of the left common carotid (depending on the subject's anatomy), which can injure the wall and prevent the distal filter from being properly deployed. Depending on the angulation, approach angle, spacing of the openings, etc., a general U-shaped curve (shown in phantom in FIG. 12A) may not be optimal for steering and accessing the left common carotid artery from the brachiocephalic trunk.

In some embodiments the distal sheath is adapted to have a preset curved configuration. The preset configuration can have, for example, a preset radius of curvature (or preset radii of curvature at different points along the distal sheath).

When the distal sheath is articulated to be steered to the preset configuration, continued articulation of the steering element can change the configuration of the distal sheath until is assumes the preset configuration. For example, the distal sheath can comprise a slotted tube with a spine extending along the length of the distal sheath. Upon actuation of the steering component, the distal sheath will bend until the portions of the distal sheath that define the slots engage, thus limiting the degree of the bend of the distal sheath. The curve can be preset into a configuration that increases the likelihood that the distal filter will, when advanced from the distal sheath, be properly positioned within the left common carotid artery.

FIGS. 13A and 13B illustrate alternative distal sheath and distal shaft portions of an exemplary filter system. FIGS. 13A and 13B only show distal shaft 120 and distal sheath 122 for clarity, but the system may also includes a proximal filter (not shown but has been deployed in brachiocephalic trunk). The distal shaft/distal sheath combination has a general S-bend configuration, with distal shaft 120 including a first bend 124 in a first direction, and distal sheath 122 configured to assume bend 126 in a second direction, wherein the first and second bends form the general S-bend configuration. FIG. 13B shows distal sheath 122 pulled back in the proximal direction relative to the proximal filter to seat the curved distal sheath against the bend. This both helps secure the distal sheath in place as well as reduces the cross sectional volume of the filter system that is disposed with the aorta. The distal shaft and distal sheath combination shown in FIGS. 13A and 13B can be incorporated into any of the filter systems described herein.

Exemplary embodiments of the delivery and deployment of a multi-filter embolic protection apparatus will now be described with reference to FIGS. 2A-2D, 13A, 13B, 14, 1, 3, 4 and 5. More particularly, the delivery and deployment will be described with reference to placement of the filter system in the brachiocephalic and left common carotid arteries. The preferred access for the delivery of the multi-filter system 10 is from the right radial or right brachial artery, however other access locations such as the right subclavian artery are possible. The system is then advanced through the right subclavian artery to a position within the brachiocephalic artery 11. At this point, proximal filter 16 may be deployed within into expanding engagement with the inner lining of brachiocephalic artery 11. Alternatively, access to the left common carotid could be gained prior to deployment of proximal filter 16. Deployment of proximal filter 16 protects both the brachiocephalic artery 11 and the right common carotid artery 7 against emboli and other foreign bodies in the bloodstream.

Figure 3:
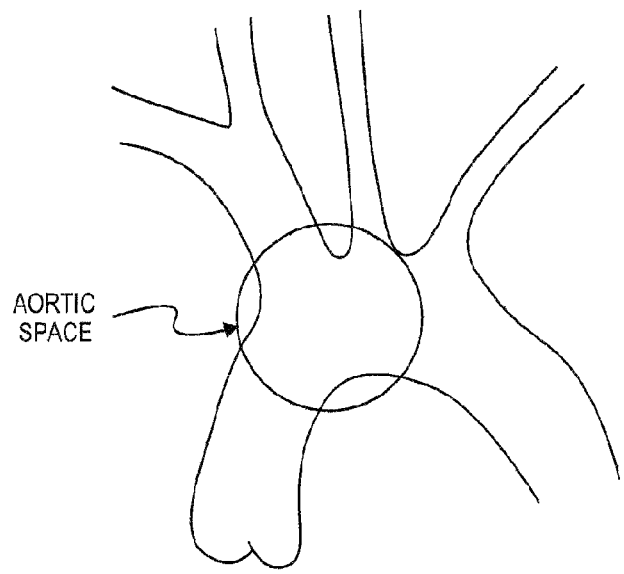
FIGS. 3-5 illustrate a portion of an exemplary delivery procedure for positioning a blood filter.
Figure 4:
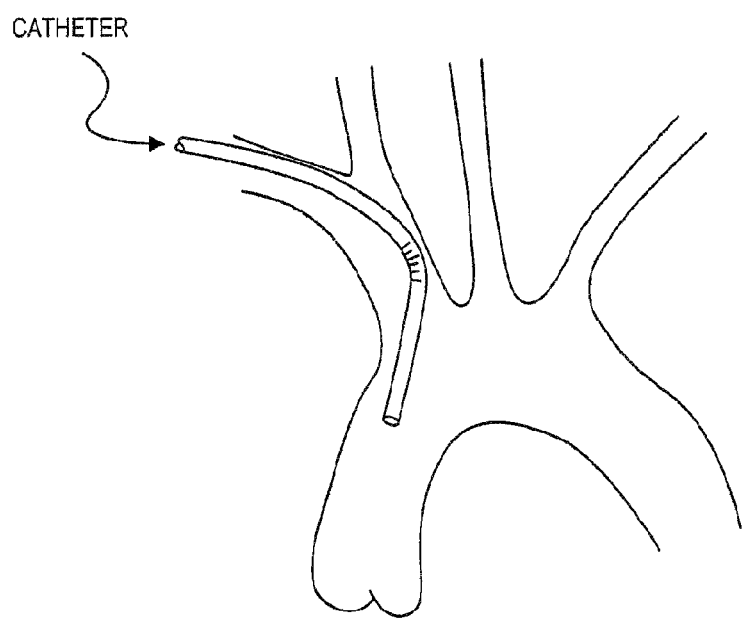
Figure 5:
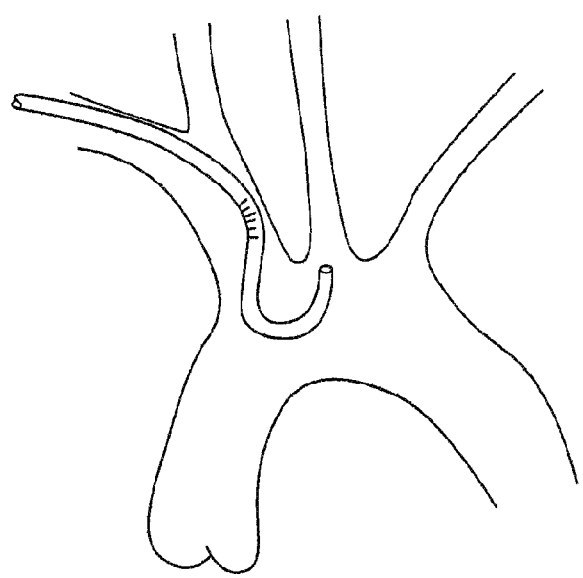

Entry into the aortic space, as illustrated in FIG. 3, is then accomplished by further advancement of the system from the brachiocephalic trunk. During this step, the filter system will tend to hug the outer portion of the brachiocephalic trunk as shown in FIG. 4. Initial tensioning of pull wire 38 causes distal sheath 48 to move the catheter-based filter system off the wall of the brachiocephalic artery just before the ostium or entrance into the aorta, as shown in FIG. 4. As the catheter path will hug the outer wall of the brachial cephalic artery, a curve directed away from this outer wall will allow additional space for the distal portion of the distal sheath to curve into the left common carotid artery, as shown in FIG. 5.

The width of slots 50 will determine the amount of bending allowed by the tube when tension is applied via pull wire 38. For example, a narrow width slot would allow for limited bending where a wider slot would allow for additional bending due to the gap or space removed from the tube. As the bending is limited by the slot width, a fixed shape or curve may be obtained when all slots are compressed and touching one another. Additional features such as chevrons may be cut into the tube to increase the strength of the tube when compressed. Other means of forming slots could be obtained with conventional techniques such as chemical etching, welding of individual elements, mechanical forming, metal injection molding or other conventional methods.

Once in the aortic space, the distal sheath is further tensioned to adjust the curvature of the distal shaft distal section 51, as shown in FIG. 9B. The amount of deflection is determined by the operator of the system based on the particular patient anatomy.

Other techniques to bias a catheter could be external force applications to the catheter and the vessel wall such as a protruding ribbon or wire from the catheter wall to force the catheter shaft to a preferred position within the vessel. Flaring a radial element from the catheter central axis could also position the catheter shaft to one side of the vessel wall. Yet another means would be to have a pull wire external to the catheter shaft exiting at one portion and reattaching at a more distal portion where a tension in the wire would bend or curve the catheter at a variable rate in relation to the tension applied.

This multi-direction and variable curvature of the distal sheath allows the operator to easily direct the filter system, or more particularly, the distal sheath section thereof, into a select vessel such as the left common carotid artery or the left innominate artery. Furthermore, the filter system allows the operator to access the left common carotid artery without the need to separately place a guidewire in the left common carotid artery. The clinical variations of these vessels are an important reason for the operator to have a system that can access differing locations and angulations between the vessels. The filter systems described herein will provide the physician complete control when attempting to access these vessels.

Once the distal sheath is oriented in the left common carotid, the handle can be manipulated by pulling it and the filter system into the bifurcation leaving the aortic vessel clear of obstruction for additional catheterizations, an example of which is shown in FIG. 12B. At this time, distal filter 22 can be advanced through proximal shaft 14 and distal shaft 18 into expanding engagement with left common carotid artery 13.

FIG. 14 illustrates a portion of an exemplary system including distal shaft 130 and distal sheath 132. Distal sheath is adapted to be able to be steered into what can be generally considered an S-bend configuration, a shepherd's staff configuration, or a crook configuration, comprised of first bend 131 and second bend 133 in opposite directions. Also shown is rotational orb 134, defined by the outer surface of the distal sheath as distal shaft 130 is rotated at least 360 degrees in the direction of the arrows shown in FIG. 14. If a typical aorta is generally in the range from about 24 mm to about 30 mm in diameter, the radius of curvature and the first bend in the S-bend can be specified to create a rotational orb that can reside within the aorta (as shown in FIG. 14), resulting in minimal interference with the vessel wall and at the same time potentially optimize access into the left common carotid artery. In other distal sheath and/or distal shaft designs, such as the one shown in FIG. 12A, the rotational orb created by the rotation of distal shaft 110 is significantly larger, increasing the risk of interference with the vessel wall and potentially decreasing the access into the left common carotid artery. In some embodiments, the diameter of the rotation orb for a distal sheath is less than about 25 mm.

Referring back to FIG. 12A, distal sheath 112, in some embodiments, includes a non-steerable distal section 121, an intermediate steerable section 119, and a proximal non-steerable section 117. When the distal sheath is actuated to be steered, only steerable portion 119 bends into a different configuration. That is, the non-steerable portions retain substantially straight configurations. The distal non-steerable portion remains straight, which can allow the distal filter to be advanced into a proper position in the left common carotid artery.

While FIG. 12A shows distal sheath 112 in a bent configuration, the distal sheath is also positioned within the lumen of the aorta. In this position, the distal sheath can interfere with any other medical device or instrument that is being advanced through the aorta. For example, in aortic valve replacement procedures, delivery device 116, with a replacement aortic valve disposed therein, is delivered through the aorta as shown in FIG. 12B. If components of the filter system are disposed within the aorta during this time, delivery device 116 and the filter system can hit each other, potentially damaging either or both systems. The delivery device 116 can also dislodge one or both filters if they are in the expanded configurations. The filter system can additionally prevent the delivery device 116 from being advanced through the aorta. To reduce the risk of contact between delivery device 116 and distal sheath 112, distal sheath 112 (and distal shaft 110) is translated in the proximal direction relative to the proximal filter (which in this embodiment has already been expanded but is not shown), as is shown in FIG. 12B. Distal sheath 112 is pulled back until the inner curvature of distal sheath 112 is seated snugly with the vasculature 115 disposed between the brachiocephalic trunk 111 and the left common carotid artery 113. This additional seating step helps secure the distal sheath in place within the subject, as well as minimize the amount of the filter system present in the aortic arch. This additional seating step can be incorporated into any of the methods described herein, and is an exemplary advantage of having a distal sheath that has three degrees of independent motion relative to the proximal filter. The combination of independent rotation, steering, and axial translation can be clinically significant to ensure the distal filter is properly positioned in the lumen, as well as making sure the filter system does not interfere with any other medical devices being delivered to the general area inside the subject.

An additional advantage of the filter systems herein is that the distal sheath, when in the position shown in FIG. 12B, will act as a protection element against any other medical instruments being delivered through the aorta (e.g., delivery device 116). Even if delivery device 116 were advanced such that it did engage distal sheath 112, distal sheath 112 is seated securely against tissue 115, thus preventing distal sheath 112 from being dislodged. Additionally, distal sheath 112 is stronger than, for example, a wire positioned within the aorta, which can easily be dislodged when hit by delivery device 116.

Figure 15A:
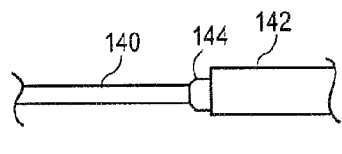
FIGS. 15A-15D illustrate alternative embodiments of the coupling of the distal shaft and distal sheath.
Figure 15B:
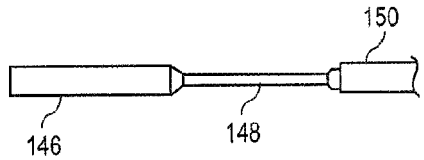
Figure 15C:
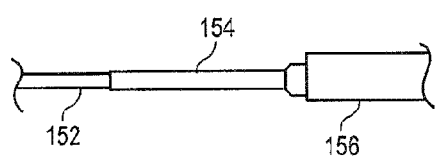
Figure 15D:
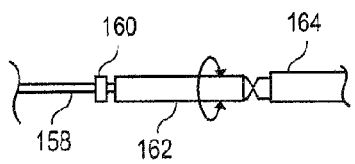

FIGS. 15A-15D illustrate alternative embodiments of the coupling of the distal shaft and distal sheath. In FIG. 15A distal shaft 140 is secured to distal sheath 142 by coupler 144. Shaft 140 has a low profile to allow for the collapse of the proximal filter (see FIG. 1C). Shaft 140 also has column strength to allow for axial translation, has sufficient torque transmission properties, and is flexible. The shaft can have a support structure therein, such as braided stainless steel. For example, the shaft can comprise polyimide, Polyether ether ketone (PEEK), Nylon, Pebax, etc. FIG. 15B illustrates an alternative embodiment showing tubular element 146, distal shaft 148, and distal sheath 150. Tubular element 146 can be a hypotube made from stainless steel, Nitinol, etc. FIG. 15C illustrates an exemplary embodiment that includes distal shaft 152, traction member 154, and distal sheath 156. Traction member 154 is coupled to shaft 152 and shaft 152 is disposed therein. Traction member 154 couples to shaft 152 for torquebility, deliverability, and deployment. Traction member 154 can be, for example without limitation, a soft silicone material, polyurethane, polyimide, or other material having suitable properties. FIG. 15D shows an alternative embodiment in which the system includes bushing 162 disposed over distal shaft 158, wherein distal shaft 158 is adapted to rotate within bushing 162. The system also includes stop 160 secured to distal shaft 158 to substantially maintain the axial position of bushing 162. When the system includes bushing 162, distal sheath 164 can be rotated relative to the proximal sheath and the proximal filter when the distal sheath and proximal sheath are in the delivery configuration (see FIG. 1B).

Figure 16:
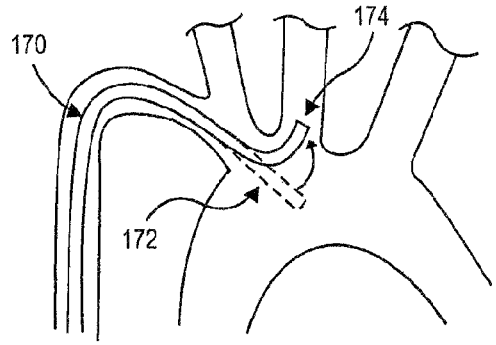
FIG. 16 illustrates an exemplary embodiment of a filter system in which the distal sheath is biased to a curved configuration.

FIG. 16 illustrates an exemplary embodiment of filter system 170 in which distal sheath 172 is biased to a curved configuration 174. The biased curved configuration is adapted to facilitate placement, delivery, and securing at least the distal filter. As shown, the distal sheath is biased to a configuration that positions the distal end of the distal sheath towards the left common carotid artery.

Figure 17:
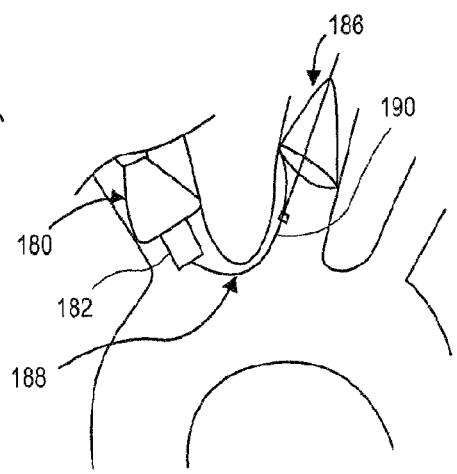
FIG. 17 illustrates a portion of an alternative filter system.

FIG. 17 illustrates a portion of an exemplary filter system and its method of use. FIG. 17 shows a system and portion of deployment similar to that shown in FIG. 2D, but distal sheath 182 has been retracted proximally relative to guiding member 190 and distal filter 186. Distal sheath 182 has been retracted substantially from the aortic arch and is substantially disposed with the brachiocephalic trunk. Guiding member 190 can have preset curve 188 adapted to closely mimic the anatomical curve between the brachiocephalic trunk and the left common carotid artery, thus minimizing the amount of the system that is disposed within the aorta. As shown, distal sheath 182 has been retracted proximally relative to proximal filter 180.

Figure 18A:
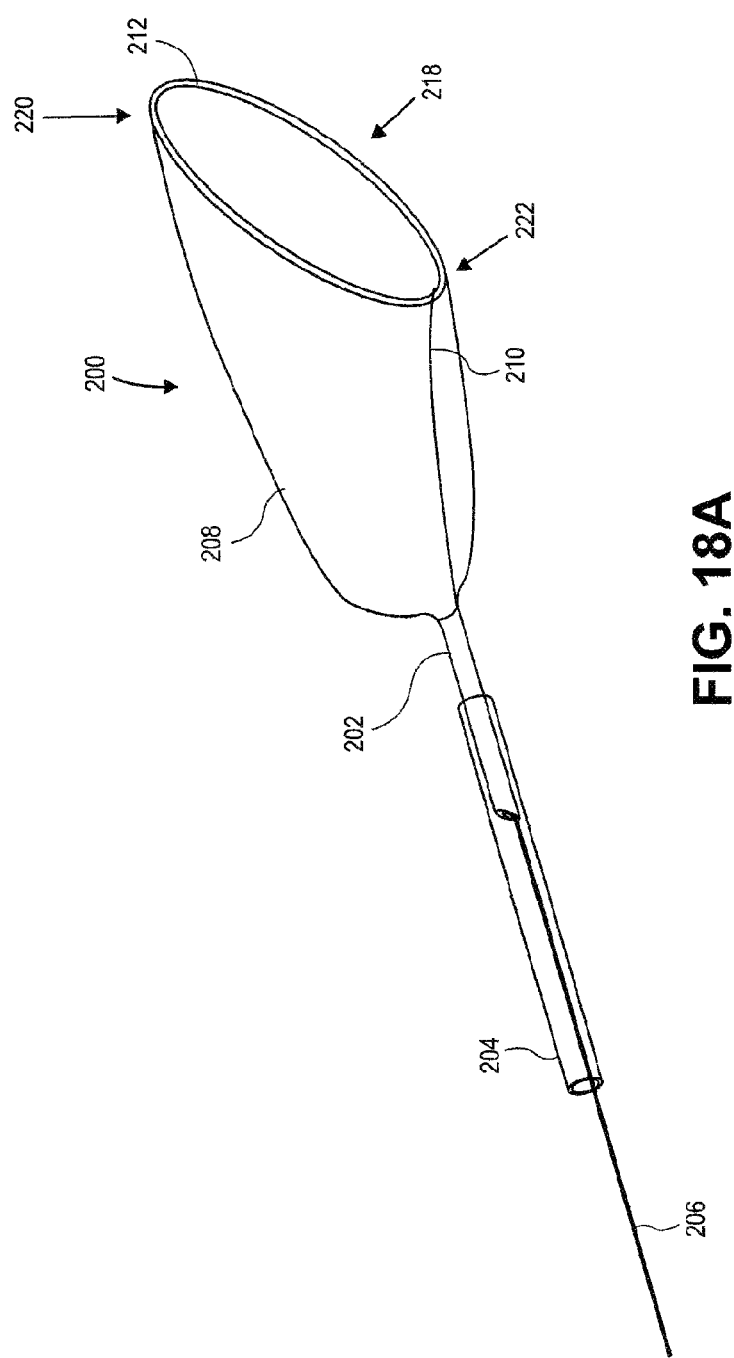
FIGS. 18A and 18B illustrate an exemplary proximal filter.
Figure 18B:
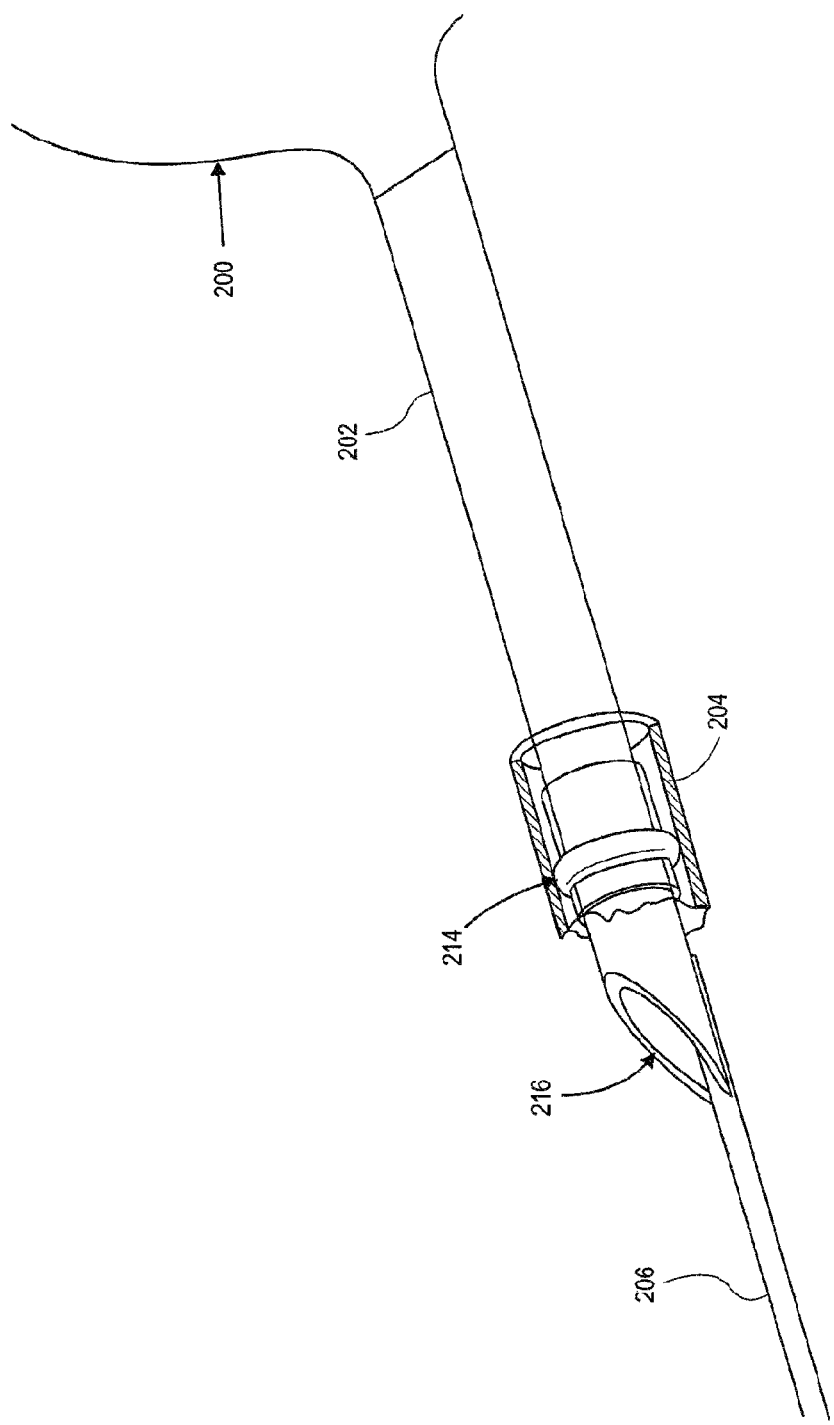

FIG. 18A is a perspective view of a portion of an exemplary embodiment of a filter system, while FIG. 18B is a close-up view of a portion of the system shown in FIG. 18A. The distal sheath and the distal filter are not shown in FIGS. 18A and 18B for clarity. The system includes proximal filter 200 coupled to proximal shaft 202, and push rod 206 coupled to proximal shaft 202. A portion of proximal sheath 204 is shown in FIG. 18A in a retracted position, allowing proximal filter 200 to expand to an expanded configuration. Only a portion of proximal sheath 204 is shown, but it generally extends proximally similar to push rod 206. The proximal end of proximal shaft 202 is beveled and defines an aspiration lumen 216, which is adapted to receive an aspirator (not shown) to apply a vacuum to aspirate debris captured within distally facing proximal filter 200. Push rod 206 extends proximally within proximal sheath 204 and is coupled to an actuation system outside of the subject, examples of which are described below. Push rod 206 takes up less space inside proximal sheath 204 than proximal shaft 202, providing a lower profile.

The system also includes proximal seal 214 disposed on the outer surface of proximal shaft 202 and adapted to engage the inner surface of the proximal sheath. Proximal seal 214 prevents bodily fluids, such as blood, from entering the space between proximal sheath 204 and proximal shaft 202, thus preventing bodily fluids from passing proximally into the filter system. The proximal seal can be, for example without limitation, a molded polymer. The proximal seal can also be machined as part of the proximal shaft, such that they are not considered two separate components.

In some specific embodiments the push rod is between 0.001 inches and 0.05 inches in diameter. In some embodiments, the diameter is between 0.01 inches and 0.025 inches in diameter. The pushrod can be constructed from any number of polymeric or metal materials, such as stainless steel. The proximal shaft can be, for example without limitation, an extruded or molded plastic, a hypotube (e.g., stainless steel), machined plastic, metal, etc.

Proximal filter 200 includes filter material 208, which comprises pores adapted to allow blood to pass therethrough, while debris does not pass through the pores and is captured within the filter material. Proximal filter 200 also includes strut 210 that extends from proximal shaft 202 to expansion support 212. Expansion support 212 has a generally annular shape but that is not intended to be limiting. Proximal filter 200 also has a leading portion 220 and a trailing portion 222. Leading portion 220 generally extends further distally than trailing portion 222 to give filter 200 a generally canted configuration relative to the proximal shaft. The canted design provides for decreased radial stiffness and a better collapsed profile. Strut 210 and expansion support 212 generally provide support for filter 200 when in the expanded configuration, as shown in FIG. 18A.

Figure 19A:
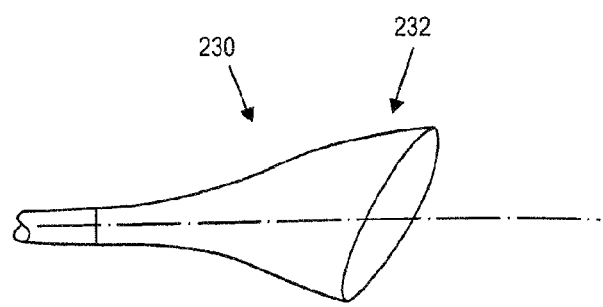
Figure 19B:
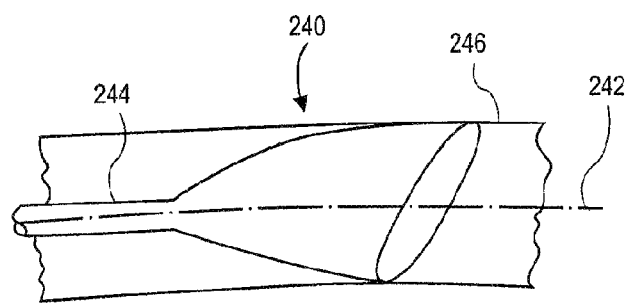
Figure 19C:
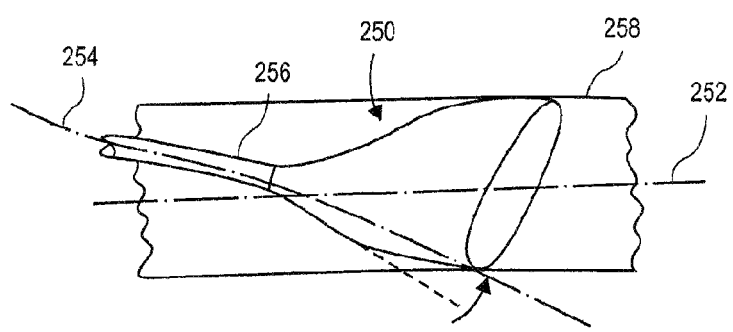

FIGS. 19A-19C illustrate exemplary embodiments of proximal filters and proximal shafts that can be incorporated into any of the systems herein. In FIG. 19A, filter 230 has flared end 232 for improved filter-wall opposition. FIG. 19B shows proximal shaft 244 substantially co-axial with vessel 246 in which filter 240 is expanded. Vessel 246 and shaft 244 have common axis 242. FIG. 19C illustrates longitudinal axis 254 of shaft 256 not co-axial with axis 252 of lumen 258 in which filter 250 is expanded.

FIGS. 20A and 20B illustrate an exemplary embodiment including proximal filter 260 coupled to proximal shaft 262. Filter 260 includes filter material 264, including slack material region 268 adapted to allow the filter to collapse easier. Filter 260 is also shown with at least one strut 270 secured to shaft 262, and expansion support 266. As shown in the highlighted view in FIG. 20B, filter 260 includes seal 274, radiopaque coil 276 (e.g., platinum), support wire 278 (e.g., Nitinol wire), and filter material 264. Any of the features in this embodiment can be included in any of the filter systems described herein.

FIG. 21 illustrates an exemplary embodiment of a proximal filter. Proximal filter 280 is coupled to proximal shaft 282. Proximal filter 280 includes struts 286 extending from proximal shaft 282 to strut restraint 288, which is adapted to slide axially over distal shaft 284. Proximal filter 280 also includes filter material 290, with pores therein, that extends from proximal shaft 282 to a location axially between proximal shaft 282 and strut restraint 288. Debris can pass through struts 286 and become trapped within filter material 290. When proximal filter 280 is collapsed within a proximal sheath (not shown), struts 286 elongate and move radially inward (towards distal shaft 284). Strut restraint 288 is adapted to move distally over distal shaft 284 to allow the struts to move radially inward and extend a greater length along distal shaft 284.

Figure 22A:
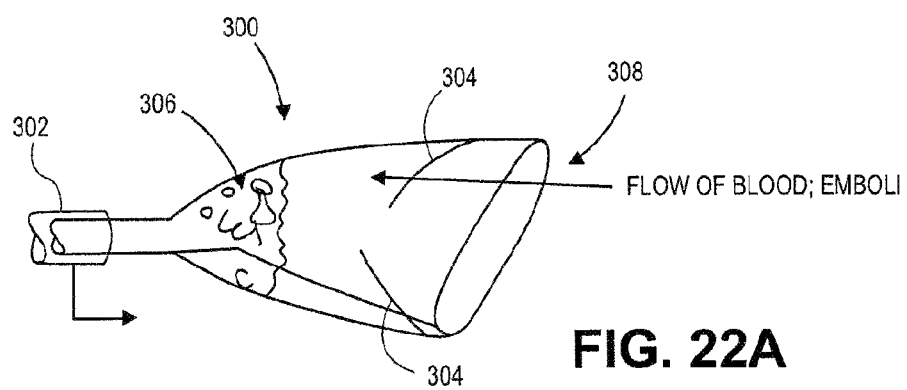
Figure 22B:
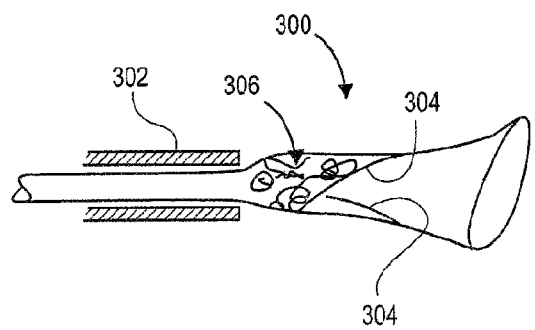

FIGS. 22A and 22B illustrate an exemplary embodiment of a proximal filter that can be incorporated into any filter system described herein. The system includes proximal filter 300 and proximal sheath 302, shown in a retracted position in FIG. 22A. Proximal filter 300 includes valve elements 304 in an open configuration in FIG. 22A. When valve elements 304 are in the open configuration, foreign particles 306 can pass through opening 308 and through the valve and become trapped in proximal filter 300, as is shown in FIG. 22A. To collapse proximal filter 300, proximal sheath 302 is advanced distally relative to proximal filter 300. As the filter begins to collapse, the valve elements are brought closer towards one another and into a closed configuration, as shown in FIG. 22B. The closed valve prevents extrusion of debris during the recapture process.

Figure 23A:
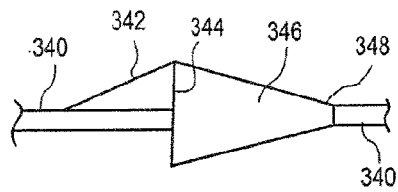
FIGS. 23A-23F illustrate exemplary distal filters.

The distal filters shown are merely exemplary and other filters may be incorporated into any of the systems herein. FIG. 23A illustrates a portion of an exemplary filter system. The system includes guiding member 340 (distal sheath not shown), strut 342, expansion support 344, and filter element 346. Strut 342 is secured directly to guiding member 340 and strut 342 is secured either directly or indirectly to expansion support 344. Filter material 346 is secured to expansion support 344. Distal end 348 of filter material 346 is secured to guiding member 340.

Figure 23B:
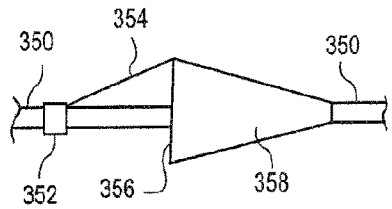

FIG. 23B illustrates a portion of an exemplary filter system. The system includes guiding element 350, strut support 352 secured to guiding element 350, strut 354, expansion support 356, and filter material 358. Strut support 352 can be secured to guiding element 350 in any suitable manner (e.g., bonding), and strut 354 can be secured to strut support 352 in any suitable manner.

Figure 23C:
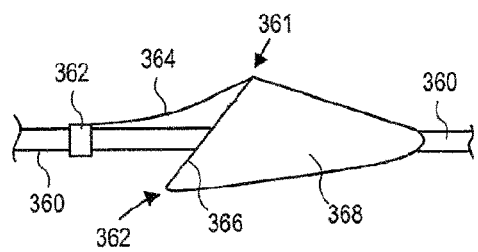
Figure 23D:
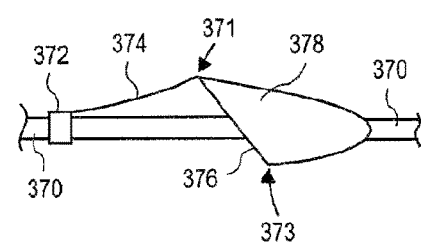

FIG. 23C illustrates a portion of an exemplary filter system. The system includes guiding element 360, strut support 362 secured to guiding element 360, strut 364, expansion support 366, and filter material 368. Expansion support 366 is adapted to be disposed at an angle relative to the longitudinal axis of guiding member 360 when the distal filter is in the expanded configuration. Expansion support 366 includes trailing portion 362 and leading portion 361. Strut 364 is secured to expansion support 366 at or near leading portion 361. FIG. 23D illustrates an exemplary embodiment that includes guiding member 370, strut support 372, strut 374, expansion support 376, and filter material 378. Expansion support 376 includes leading portion 373, and trailing portion 371, wherein strut 374 is secured to expansion element 376 at or near trailing portion 371. Expansion support 376 is disposed at an angle relative to the longitudinal axis of guiding member 370 when the distal filter is in the expanded configuration.

Figure 23E:
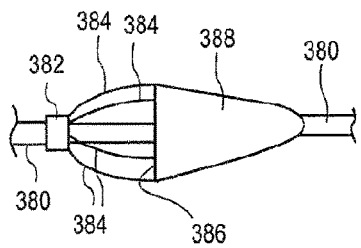

FIG. 23E illustrates an exemplary embodiment of a distal filter in an expanded configuration. Guiding member 380 is secured to strut support 382, and the filter includes a plurality of struts 384 secured to strut support 382 and to expansion support 386. Filter material 388 is secured to expansion support 386. While four struts are shown, the distal filter may include any number of struts.

Figure 23F:
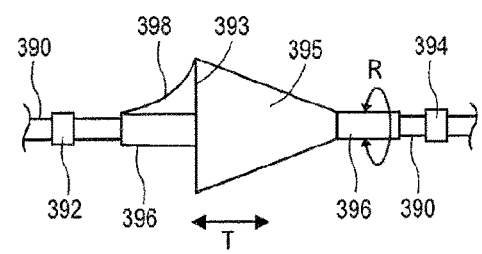

FIG. 23F illustrates an exemplary embodiment of a distal filter in an expanded configuration. Proximal stop 392 and distal stop 394 are secured to guiding member 390. The distal filter includes tubular member 396 that is axially slidable over guiding member 390, but is restricted in both directions by stops 392 and 394. Strut 398 is secured to slidable member 396 and to expansion support 393. Filter material 395 is secured to slidable member 396. If member 396 slides axially relative to guiding member 390, filter material 395 moves as well. Member 396 is also adapted to rotate in the direction "R" relative to guiding member 390. The distal filter is therefore adapted to independently move axially and rotationally, limited in axial translation by stops 392 and 394. The distal filter is therefore adapted such that bumping of the guiding member or the distal sheath will not disrupt the distal filter opposition, positioning, or effectiveness.

As shown in FIGS. 23A-23B, in some embodiments, the strut 342, 354 has a straight configuration. A straight configuration may allow for a shorter attachment between the filter and the guiding member. In other embodiments, as shown in FIGS. 23C-23D, the strut 364, 374, takes a curved configuration. In still other embodiments, the strut has two or more curves. For example, the strut may take a sinusoidal configuration and transition from a first curve to the opposite curve to aid in transition to the filter frame. In some embodiments, the first curve may have a larger radius than the opposite curve. In still other embodiments, the first curve may have a smaller radius than the opposite curve.

Figure 24A:
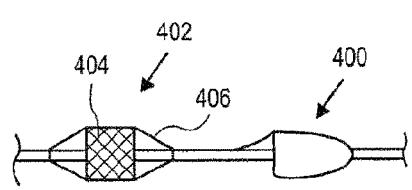
FIGS. 24A-24C illustrate exemplary embodiments in which the system includes at least one distal filter positioning, or stabilizing, anchor.
Figure 24B:
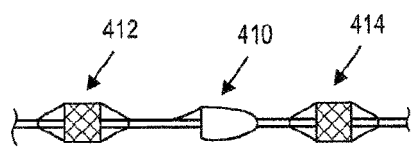
Figure 24C:
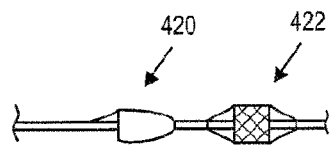

FIGS. 24A-24C illustrate exemplary embodiments in which the system includes at least one distal filter positioning, or stabilizing, anchor. The positioning anchor(s) can help position the distal anchor in a proper position and/or orientation within a bodily lumen. In FIG. 24A the system includes distal filter 400 and positioning anchor 402. Anchor 402 includes expandable stent 404 and expandable supports 406. Supports 406 and filter 400 are both secured to the guiding member. Anchor 402 can be any suitable type of expandable anchor, such as, for example without limitation, stent 404. Anchor 402 can be self-expandable, expandable by an expansion mechanism, or a combination thereof. In FIG. 24A, stent 404 can alternatively be expanded by an expansion balloon. Anchor 402 is disposed proximal to filter 400. FIG. 24B illustrates an embodiment in which the system includes first and second anchors 412 and 414, one of which is proximal to filter 410, while the other is distal to filter 410. FIG. 24C illustrates an embodiment in which anchor 422 is distal relative to filter 420.

In some embodiments the distal filter is coupled, or secured, to a guiding member that has already been advanced to a location within the subject. The distal filter is therefore coupled to the guiding member after the distal filter has been advanced into the subject, rather than when the filter is outside of the subject. Once coupled together inside the subject, the guiding member can be moved (e.g., axially translated) to control the movement of the distal filter. In some embodiments the guiding member has a first locking element adapted to engage a second locking element on the distal filter assembly such that movement of the guiding member moves the distal filter in a first direction. In some embodiments the distal filter assembly has a third locking element that is adapted to engage the first locking element of the guiding member such that movement of the guiding member in a second direction causes the distal filter to move with the guiding member in the second direction. The guiding member can therefore be locked to the distal filter such that movement of the guiding member in a first and a second direction will move the distal filter in the first and second directions.

Figure 25A:
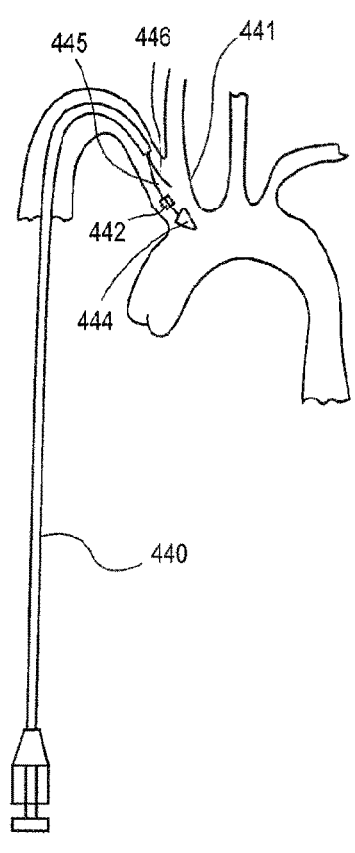
FIGS. 25A-25D illustrate an exemplary embodiment of coupling a distal filter to a docking wire inside of the subject.
Figure 25B:
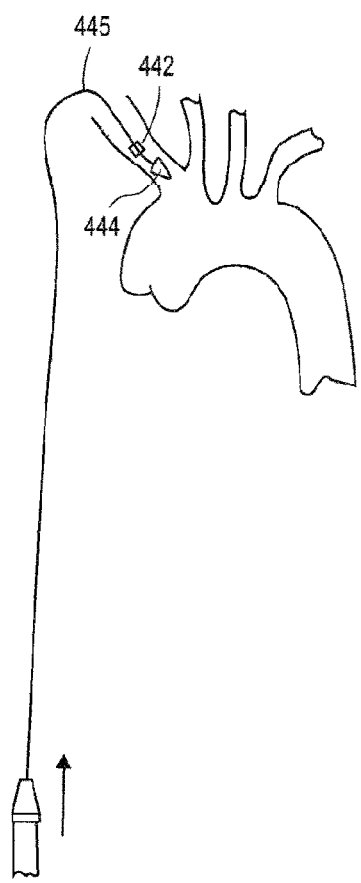
Figure 25C:
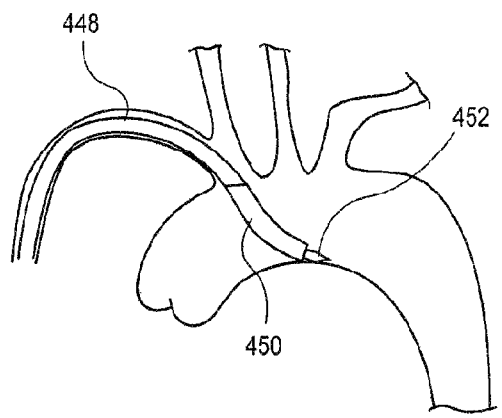
Figure 25D:
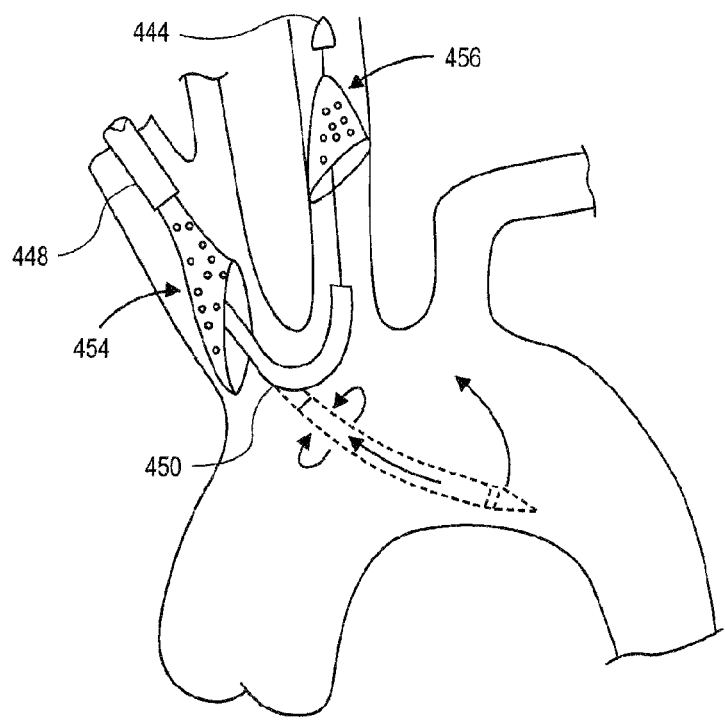

By way of example, FIGS. 25A-25D illustrate an exemplary embodiment of coupling the distal filter to a docking wire inside of the subject, wherein the docking wire is subsequently used to control the movement of the distal filter relative to the distal sheath. In FIG. 25A, guide catheter 440 has been advanced through the subject until the distal end is in or near the brachiocephalic trunk 441. A docking wire, comprising a wire 445, locking element 442, and tip 444, has been advanced through guide catheter 440, either alone, or optionally after guiding wire 446 has been advanced into position. Guiding wire 446 can be used to assist in advancing the docking wire through guide catheter 440. As shown, the docking wire has been advanced from the distal end of guide catheter 440. After the docking wire is advanced to the desired position, guide catheter 440, and if guiding wire 446 is used, are removed from the subject, leaving the docking wire in place within the subject, as shown in FIG. 25B. Next, as shown in FIG. 25C, the filter system, including proximal sheath 448 with a proximal filter in a collapsed configuration therein (not shown), distal sheath 450, with a distal filter assembly (not shown) partially disposed therein, is advanced over wire 445 until a locking portion of the distal filter (not shown but described in detail below) engages locking element 442. The distal filter assembly will thereafter move (e.g., axially) with the docking wire. Proximal sheath 448 is retracted to allow proximal filter 454 to expand (see FIG. 25D). Distal sheath 450 is then actuated (e.g., bent, rotated, and/or translated axially) until it is in the position shown in FIG. 25D. A straightened configuration of the distal sheath is shown in phantom in FIG. 25D, prior to bending, proximal movement, and/or bending. The docking wire is then advanced distally relative to distal sheath 450, which advances distal filter 456 from distal sheath 450, allowing distal filter 456 to expand inside the left common carotid artery, as shown in FIG. 25D.

Figure 26A:
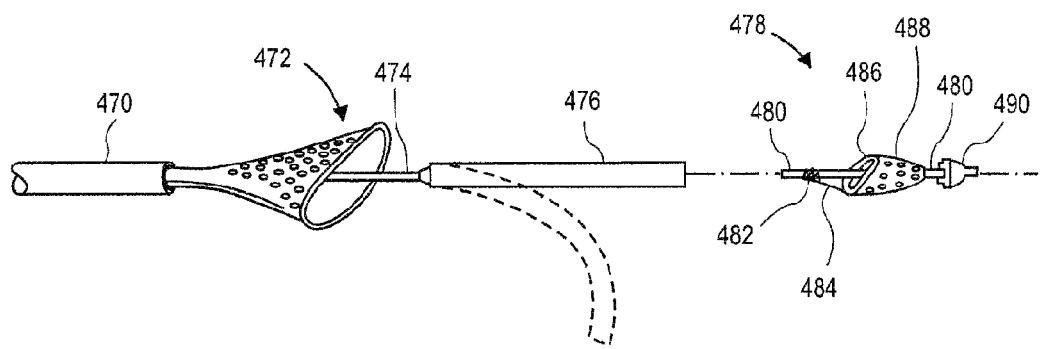
Figure 26B:
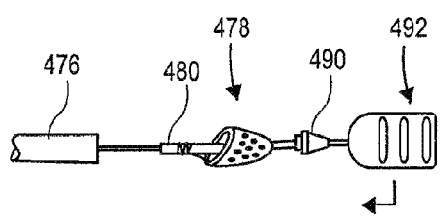
Figure 26C:
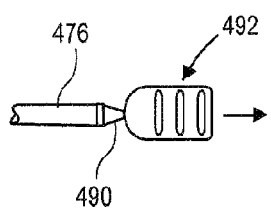
Figure 26D:
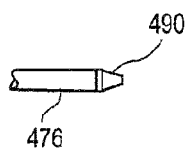

FIGS. 26A-26D illustrate an exemplary method of preparing an exemplary distal filter assembly for use. FIG. 26A illustrates a portion of the filter system including proximal sheath 470, proximal filter 472 is an expanded configuration, distal shaft 474, and articulatable distal sheath 476. Distal filter assembly 478 includes an elongate member 480 defining a lumen therein. Elongate member 480 is coupled to distal tip 490. Strut 484 is secured both to strut support 482, which is secured to elongate member 480, and expansion support 486. Filter element 488 has pores therein and is secured to expansion support 486 and elongate member 480. To load distal filter assembly 478 into distal sheath 476, loading mandrel 492 is advanced through distal tip 490 and elongate member 480 and pushed against distal tip 490 until distal filter assembly 478 is disposed within distal sheath 476, as shown in FIG. 26C. Distal tip 490 of the filter assembly remains substantially distal to distal sheath 476, and is secured to the distal end of distal sheath 476. Distal tip 490 and distal sheath 476 can be secured together by a frictional fit or other type of suitable fit that disengages as described below. Loading mandrel 492 is then removed from the distal filter and distal sheath assembly, as shown in FIG. 26D.

FIG. 26E illustrates docking wire 500 including wire 502, lock element 504, and distal tip 506. Docking wire 500 is first advanced to a desired position within the subject, such as is shown in FIG. 25B. The assembly from FIG. 26D is then advanced over docking wire, wherein distal tip 490 is first advanced over the docking wire. As shown in the highlighted view in FIG. 26F, distal tip 490 of the distal filter assembly includes first locking elements 510, shown as barbs. As the filter/sheath assembly continues to be distally advanced relative to the docking wire, the docking wire locking element 504 pushes locks 510 outward in the direction of the arrows in FIG. 26F. After lock 504 passes locks 510, locks 510 spring back inwards in the direction of the arrows shown in FIG. 26G. In this position, when docking wire 500 is advanced distally (shown in FIG. 26F), lock element 504 engages with lock elements 510, and the lock element 504 pushes the distal filter assembly in the distal direction. In this manner the distal filter can be distally advanced relative to the distal sheath to expand the distal filter. Additionally, when the docking wire is retracted proximally, locking element 504 engages the distal end 512 of elongate member 480 and pulls the distal filter in the proximal direction. This is done to retrieve and/or recollapse the distal filter back into the distal sheath after it has been expanded.

Figures 27A, 27B:
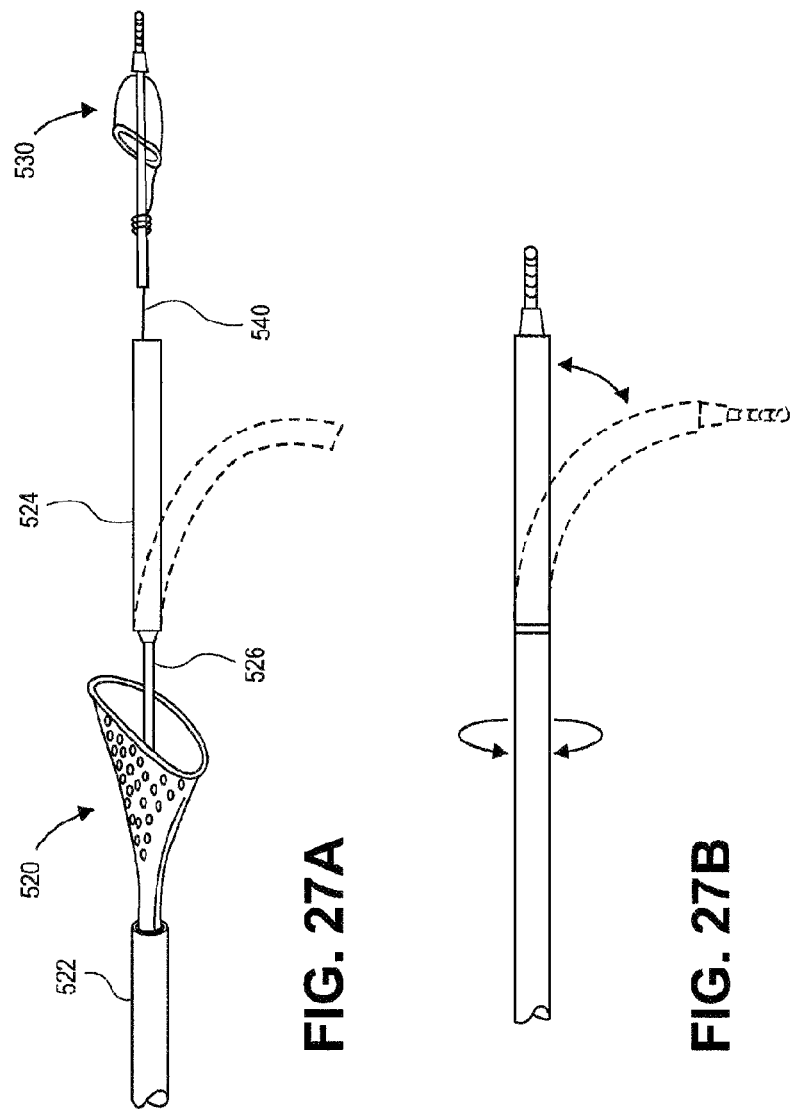
FIGS. 27A and 27B illustrate an exemplary embodiment in which a guiding member, secured to a distal filter before introduction into the subject is loaded into an articulatable distal sheath.

FIGS. 27A and 27B illustrate an exemplary embodiment in which guiding member 540, secured to distal filter 530 before introduction into the subject is loaded into articulatable distal sheath 524. The system also includes proximal filter 520, proximal sheath 522, and distal shaft 526. FIG. 27B shows the system in a delivery configuration in which both filters are collapsed.

Figure 28B:
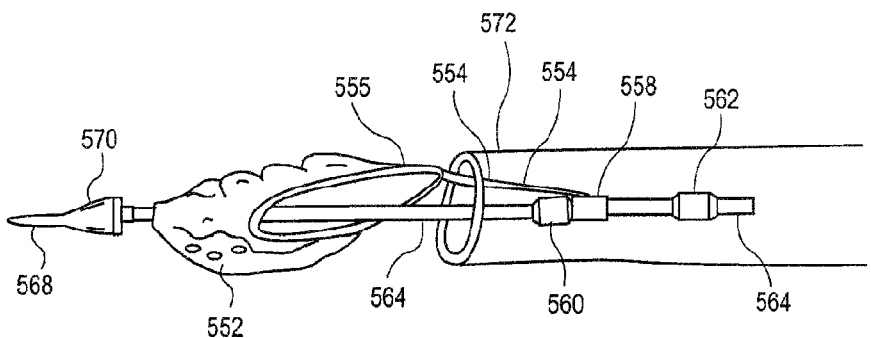

FIGS. 28A-28E illustrate an exemplary distal filter assembly in collapsed and expanded configurations. In FIG. 28A, distal filter assembly 550 includes a distal frame, which includes strut 554 and expansion support 555. The distal frame is secured to floating anchor 558, which is adapted to slide axially on elongate member 564 between distal stop 560 and proximal stop 562, as illustrated by the arrows in FIG. 28A. The distal filter assembly also includes membrane 552, which has pores therein and is secured at its distal end to elongate member 564. The distal filter assembly is secured to a guiding member, which includes wire 566 and soft distal tip 568. The guiding member can be, for example, similar to the docking wire shown in FIGS. 26A-26E above, and can be secured to the distal filter assembly as described in that embodiment.

The floating anchor 558 allows filter membrane 552 to return to a neutral, or at-rest, state when expanded, as shown in FIG. 28A. In its neutral state, there is substantially no tension applied to the filter membrane. The neutral deployed state allows for optimal filter frame orientation and vessel apposition. In the neutral state shown in FIG. 28A, floating anchor 558 is roughly mid-way between distal stop 560 and proximal stop 562, but this is not intended to be a limiting position when the distal filter is in a neutral state.

Figure 28C:
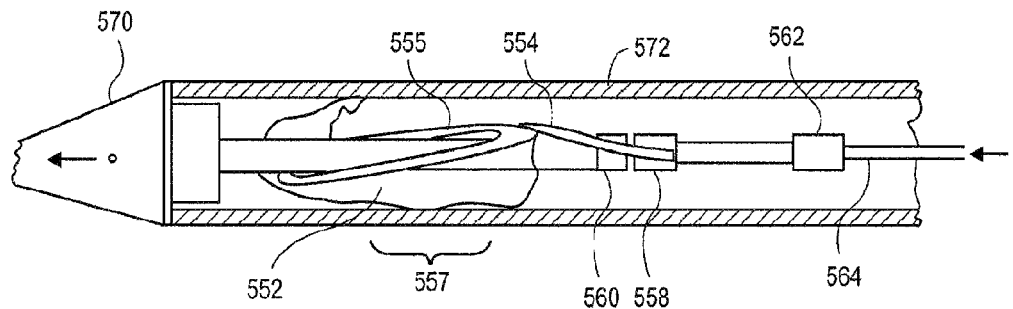
Figure 28D:
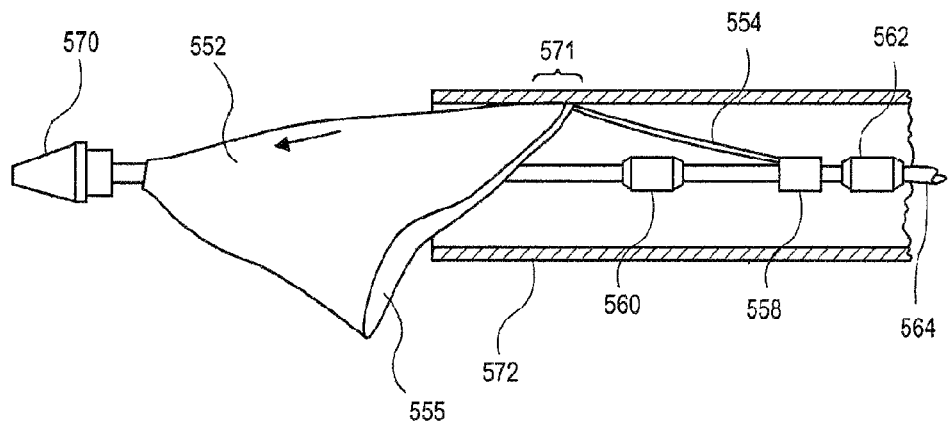
Figure 28E:
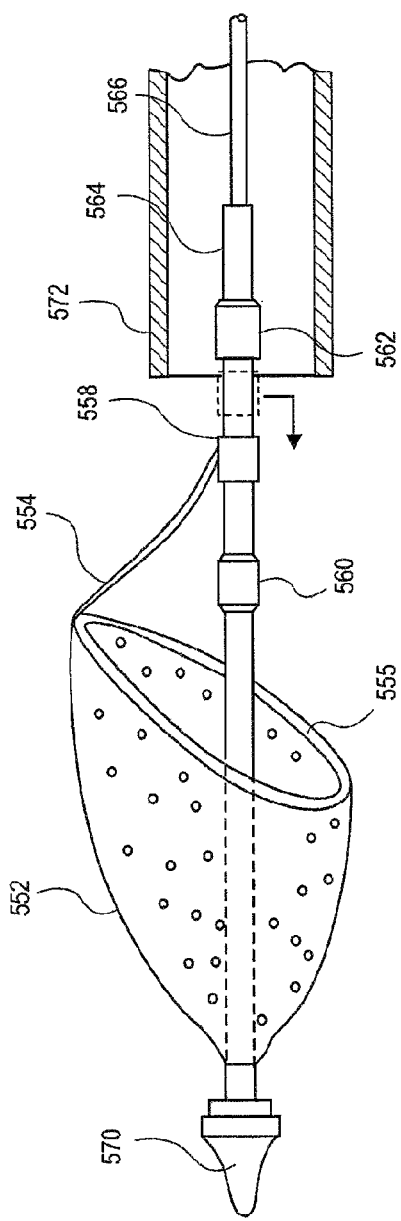

FIG. 28B illustrates the distal filter being sheathed into distal sheath 572. During the sheathing process, the distal filter is collapsed from an expanded configuration (see FIG. 28A) towards a collapsed configuration (see FIG. 28C). In FIG. 28B, distal sheath 572 is moving distally relative to the distal filter. The distal end of the distal sheath 572 engages with strut 554 as it is advanced distally, causing the distal end of strut 554 to moves towards elongate member 564. Strut 554 can be thought of as collapsing towards elongate member 564 from the configuration shown in FIG. 28A. The force applied from distal sheath 572 to strut 554 collapses the strut, and at the same time causes floating anchor 558 to move distally on tubular member 564 towards distal stop 560. In FIG. 28B, floating anchor 558 has been moved distally and is engaging distal stop 560, preventing any further distal movement of floating anchor 558. As strut 554 is collapsed by distal sheath 572, strut 554 will force the attachment point between strut 554 and expansion support 555 towards tubular member 564, beginning the collapse of expansion support 555. Distal sheath 572 continues to be advanced distally relative to the distal filter (or the distal filter is pulled proximally relative to the distal sheath, or a combination of both) until the distal filter is collapsed within distal sheath 572, as is shown in FIG. 28C. Filter membrane 552 is bunched to some degree when the filter is in the configuration shown in FIG. 28C. To deploy the distal filter from the sheath, guiding member 566 is advanced distally relative to the distal sheath (or the distal sheath is moved proximally relative to the filter). The distal portions of filter membrane 552 and expansion support 555 are deployed first, as is shown in FIG. 28D. Tension in the filter membrane prevents wadding and binding during the deployment. When strut 554 is deployed from the distal sheath, expansion support 555 and strut 554 are able to self-expand to an at-rest configuration, as shown in FIG. 28E. Floating anchor 558 is pulled in the distal direction from the position shown in FIG. 28D to the position shown in FIG. 28E due to the expansion of strut 554.

FIGS. 29A-29E illustrate a portion of an exemplary filter system with a lower delivery and insertion profile. In FIG. 29A, the system includes proximal sheath 604 with a larger outer diameter than distal sheath 602. In some embodiments proximal sheath 604 has a 6 F outer diameter, while distal sheath 602 has a 5 F outer diameter. A guiding member including distal tip 606 is disposed within the distal sheath and the proximal sheath. FIG. 29B illustrates tear-away introducer 608, with receiving opening 610 and distal end 612. Introducer is first positioned within a subject with receiving opening 610 remaining outside the patient. As shown in FIG. 29C, the smaller diameter distal sheath is first advanced through the receiving opening of introducer 608 until the distal end of the distal sheath is disposed distal relative to the distal end of the introducer. The introducer is then split apart and removed from the subject, as shown in FIG. 29D. The filter system can then be advanced distally through the subject. The introducer can be a 5 F introducer, which reduces the insertion and delivery profile of the system.

The embodiments in FIGS. 25A-25B above illustrated some exemplary systems and methods for routing filter systems to a desired location within a subject, and additional exemplary embodiments will now be described. FIGS. 30A and 30B illustrate an exemplary embodiment similar to that which is shown in FIGS. 27A and 27B. The filter system shows distal filter 650 and proximal filter 644 in expanded configurations. Proximal sheath 642 has been retracted to allow proximal filter 644 to expand. Distal filter, which is secured to guiding member 648, are both advanced distally relative to distal articulating sheath 640. The filter system does not have a dedicated guidewire that is part of the system, but distal sheath 640 is adapted to be rotated and steered to guide the system to a target location within the subject.

FIGS. 31A-31C illustrate an exemplary over-the-wire routing system that includes a separate distal port for a dedicated guidewire. A portion of the system is shown in FIG. 31B, including distal articulating sheath 662 and proximal sheath 660 (the filters are collapsed therein). FIG. 31B is a highlighted view of a distal region of FIG. 31A, showing guidewire entry port 666 near the distal end 664 of distal sheath 662. FIG. 31C is a sectional view through plane A of distal sheath 662, showing guidewire lumen 672, spine element 678, distal filter lumen 674, and steering element 676 (shown as a pull wire). Guidewire lumen 672 and distal filter lumen 674 are bi-axial along a portion of distal sheath, but in region 670 guidewire lumen 672 transitions from within the wall of distal sheath 662 to being co-axial with proximal sheath 660.

To deliver the system partially shown in FIGS. 31A-31C, a guidewire is first delivered to a target location within the subject. The guidewire can be any type of guidewire. With the guidewire in position, the proximal end of the guidewire is loaded into guidewire entry port 666. The filter system is then tracked over the guidewire to a desired position within the subject. Once the system is in place, the guidewire is withdrawn from the subject, or it can be left in place. The proximal and distal filters can then be deployed as described in any of the embodiments herein.

FIGS. 32A-32E illustrate an exemplary routing system which includes a rapid-exchange guidewire delivery. The system includes distal articulating sheath 680 with guidewire entry port 684 and guidewire exit port 686. The system also includes proximal sheath 682, a distal filter secured to a guiding member (collapsed within distal sheath 680), and a proximal filter (collapsed within proximal sheath 682). After guidewire 688 is advanced into position within the patient, the proximal end of guidewire 688 is advanced into guidewire entry port 684. Distal sheath (along with the proximal sheath) is tracked over guidewire 688 until guidewire 688 exits distal sheath 680 at guidewire exit port 686. Including a guidewire exit port near the entry port allows for only a portion of the guidewire to be within the sheath(s), eliminating the need to have a long segment of guidewire extending proximally from the subject's entry point. As soon as the guidewire exits the exit port, the proximal end of the guidewire and the proximal sheath can both be handled.

Figure 32A:
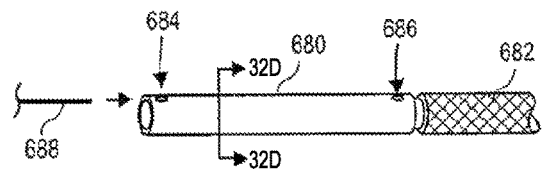
FIGS. 32A-32E illustrate an exemplary routing system which includes a rapid-exchange guidewire delivery.
Figure 32B:
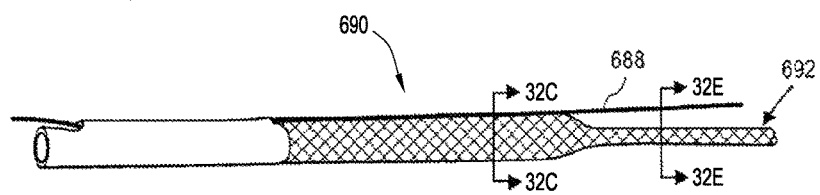
Figure 32C:
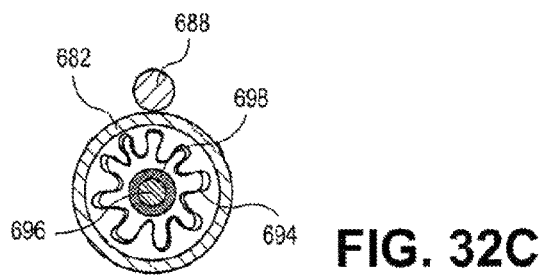

FIG. 32B shows guidewire 688 extending through the guidewire lumen in the distal sheath and extending proximally from exit port 686. Guidewire 688 extends adjacent proximal sheath 682 proximal to exit port 686. In FIG. 32B, portion 690 of proximal sheath 682 has a diameter larger than portion 692 to accommodate the proximal filter therein. Portion 692 has a smaller diameter for easier passage of the proximal sheath and guidewire. FIG. 32C shows a sectional view through plane 32C-32C of FIG. 32B, with guidewire 688 exterior and adjacent to proximal sheath 682. Proximal filter 694 is in a collapsed configuration within proximal sheath 682, and guiding member 696 is secured to a distal filter, both of which are disposed within distal shaft 698.

Figure 32D:
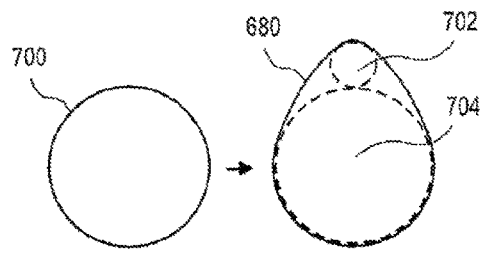

FIG. 32D shows relative cross-sections of exemplary introducer 700, and distal sheath 680 through plane 32D-32D. Distal sheath 680 includes guidewire lumen 702 and distal filter lumen 704. In some embodiments, introducer 700 is 6 F, with an inner diameter of about 0.082 inches. In comparison, the distal sheath can have a guidewire lumen of about 0.014 inches and distal filter lumen diameter of about 0.077 inches.

Figure 32E:
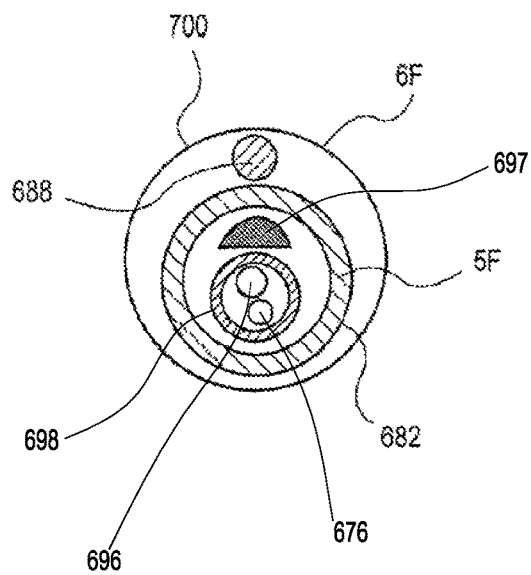

FIG. 32E shows a sectional view through plane 32E-32E, and also illustrates the insertion through introducer 700. Due to the smaller diameter of portion 692 of proximal sheath 682, guidewire 688 and proximal sheath 682 more easily fit through introducer 700 than the distal sheath and portion of the proximal sheath distal to portion 692. The size of the introducer may vary depending on the diameter of the filter system. The introducer may range in size from 4 F to 15 F. In certain embodiments, the size of the introducer is between 4 F and 8 F. Guidewire 688 may vary in diameter between 0.005 and 0.02 inches or between 0.01 and 0.015 inches. In some situations, it may be desirable to have a guidewire smaller than 0.005 inches or larger than 0.02 inches in diameter. The smaller diameter proximal portion 692 of proximal sheath 682 allows for optimal sheath and guidewire movement with the introducer sheath. In certain aspects, it may be desirable for the cross-section of proximal filter deployment member 697 to take a non-circular shape to reduce the profile of proximal sheath 682. Guiding member 696 and distal sheath pull wire 676 are both disposed through distal shaft 698.

In certain embodiments, the guiding member is a core wire. Use of a core wire may be desirable to decrease the diameter of the filter system. A core wire is also flexible and able to access tortuous anatomies. The material and diameter of the guiding member may vary depending on the desired level of column strength or flexibility. In certain embodiments, the core wire may be tapered such that a distal section of the core wire has a smaller diameter than a proximal section of the core wire to increase flexibility at the distal section.

In certain clinical scenarios, it may be desirable for the guiding member to take the form of a tubular core member having a guidewire lumen running therethrough. In several embodiments, the tubular core member is a catheter shaft. The presence of the guidewire lumen allows the user to deliver the filter system to the correct position by advancing the filter system over the guidewire. A tubular core member allows the user to select an appropriate guidewire for the procedure rather than restricting the user to the wire core shaft. A guiding member having a guidewire lumen can potentially reduce the delivery profile of the filter system by not requiring separate lumens for the guiding member and the guidewire.

Figure 33A:
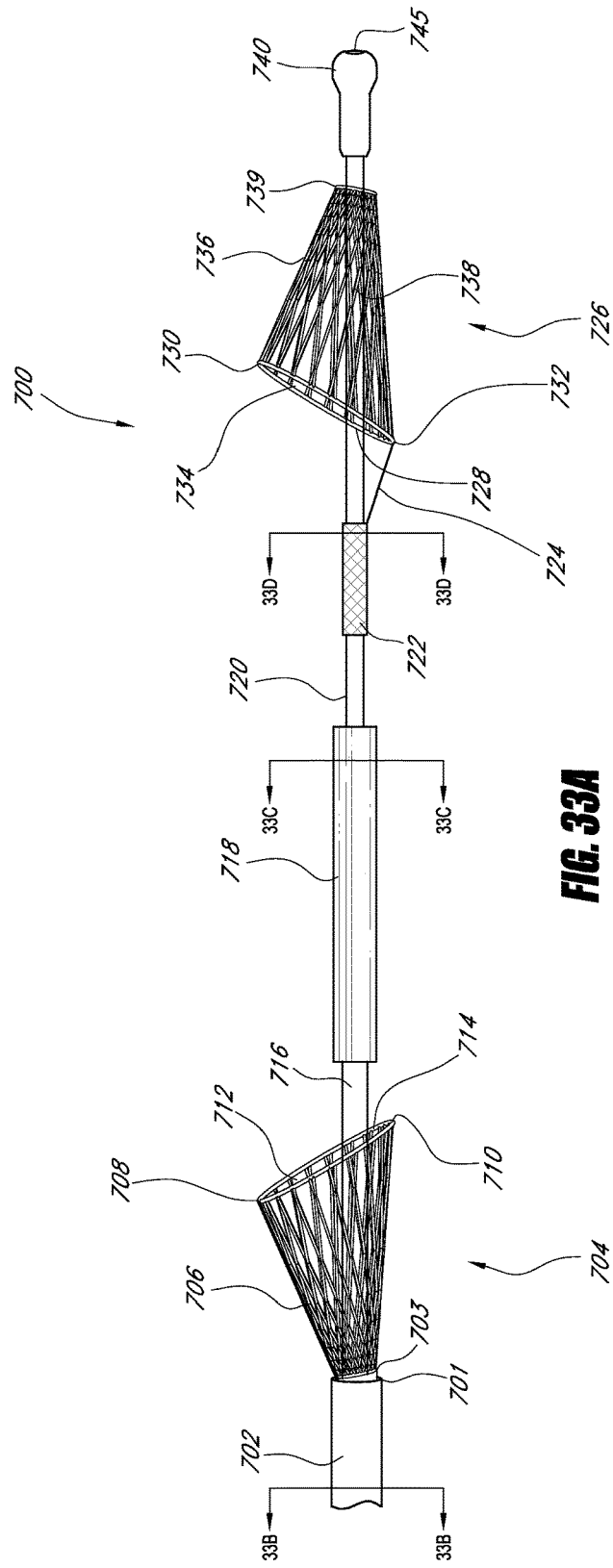
FIGS. 33A-D illustrates a filter system which includes a tubular core member.

FIG. 33A illustrates filter system 700 having tubular core member 720 extending along an elongate axis of filter system 700 and slidably disposed through distal shaft 716. The distal end of tubular core member 720 is positioned in a distal, atraumatic tip 740 of filter system 700, while the proximal end of tubular core member 720 is positioned in the control handle. The proximal end of tubular core member 720 is connected to an actuation mechanism capable of advancing tubular core member 720 distally or retracting tubular core member 720 proximally with respect to distal shaft 716. Distal filter assembly 726 may be mounted on a distal section of tubular core member 720. Proximal filter 704 and distal filter 726 are illustrated as formed from a plurality of struts such as a woven wire or laser cut basket, however any of the polymeric membrane filters disclosed elsewhere herein may be used in filter system 700.

In certain embodiments, tubular core member 720 defines a guidewire lumen 745. Tubular core member 720 may have a distal guidewire entry port at the distal end of tubular core member 720 and a proximal guidewire exit port at the proximal end of tubular core member 720. In other embodiments, the proximal guidewire port may be positioned at any position along the length of the tubular core member.

The length of tubular core member 720 may range from about 50 cm to about 300 cm. In some embodiments, the length may be less than 50 cm; while in other embodiments, the length may be greater than 300 cm. In several embodiments, the length of tubular core member 720 is between about 50 and about 150 cm, between about 75 and about 125 cm, or between about 100 cm and about 150 cm. The inner diameter of tubular core member 720 may range from about 0.01 to about 0.075 cm. In other embodiments, the inner diameter of tubular core member 720 is less than 0.01 cm; while in still other embodiments, the inner diameter is greater than 0.075 cm. The outer diameter of tubular core member 720 may range from about 0.025 to about 0.1 cm. In certain embodiments, the outer diameter of tubular core member 720 is less than 0.025 cm; while in other embodiments, the inner diameter is greater than 0.1 cm.

In certain clinical scenarios, it may be desirable to increase the column strength of tubular core member 720, thus improving support and pushability to aid advancement of distal filter assembly 726 out of distal sheath 718. In certain scenarios, tubular core member 720 may be constructed from a material stiffer than the material from which distal shaft 716 is constructed. A stiffer tubular core member 720 can help improve the column strength of filter system 700. The tubular core member 720 may be constructed from metallic materials such as stainless steel, Nitinol, cobalt chromium (MP35N), or other alloys used in medical devices. Alternatively, tubular core member 720 may be constructed from a polymer construction such as nylon, polyester, polypropylene, polyimide, or other polymers exhibiting similar properties. In some embodiments, tubular core member 720 may be constructed from a combination of metallic materials and polymeric materials. In some embodiments, the inner diameter of tubular core member 720 is either coated with or constructed of a lubricious polymer (e.g. HDPE, PTFE, FEP, etc.). In still other embodiments, tubular core member may include reinforcements. For example, a ribbon or other stiffening member may extend along a section of tubular core member 720. Alternatively, tubular core member 720 may have a multi-lumen profile, a first lumen for a guidewire and a second lumen for a stiffening mandrel. Tubular core member 720 may also transition from a multi-lumen profile to a single lumen profile to increase flexibility along the single lumen section of the tubular core member. In still other embodiments, tubular core member 720 may include one or more longitudinal strands dispersed within the tubular core member shaft to improve tensile strength. In some embodiments, tubular core member 720 may have a braided or coiled shaft to increase column strength. In certain embodiments, the braid consists of both metallic and polymer materials. In other embodiments, the braid consists of only metal; while in still other embodiments, the braid consists of only polymer materials.

In other clinical scenarios, it may be desirable to provide more flexibility in certain sections or along the entire length of tubular core member 720. When filter system 700 is deployed in a curved lumen, a rigid tubular core member 720 or other guiding member may pull the leading portion 732 of distal filter 736 away from the vessel wall if the distal region of tubular core member 720 or other guiding member lacks sufficient flexibility to deflect relative to filter system 700 in a tortuous anatomy.

In certain embodiments, tubular core member 720 may be constructed from a more flexible material. In other embodiments, a first portion of tubular core member 720 may be constructed from a flexible material, while a second portion of tubular core member 720 is constructed from a stiffer material. Alternatively, removal of portions of tubular core member 720 may provide greater flexibility along certain sections of tubular core member 720. For example, a series of slots, cuts, or a spiral pattern may be cut into a section of tubular core member 720 to provide a flex zone having a greater flexibility than proximal and distal adjacent portions of tubular core member 720. The pattern of cuts may vary along the tubular core member shaft to vary flexibility along tubular core member 720. The flexible portion may alternatively comprise a coil, helix, or interrupted helix. In other embodiments, a first portion of the tubular core member may also have a thinner wall than a second portion of the tubular core member. In still other embodiments, tubular core member 720 may be tapered to increase stiffness along a first section of the tubular core member and increase flexibility along a second section of the tubular core member.

In certain embodiments, a distal section of tubular core member 720 may be more flexible than a proximal section of the tubular core member 720 using any of the methods discussed above. The length of the flexible distal section may measure from about 5 cm to about 50 cm, from about 10 to about 40 cm, or from about 15 to about 25 cm. In other embodiments, the flexible distal section may be less than 5 cm or greater than 50 cm.

Several embodiments may include a flexible coupler 722 to allow distal filter assembly 726 to deflect relative to the rest of filter system 700. In several embodiments, tubular core member 720 includes a flexible coupler 722 positioned proximal to distal filter assembly 726. In several embodiments, flexible coupler 722 defines a lumen through which a guidewire may pass. In some embodiments, flexible coupler 722 is spliced into a gap along tubular core member 720. In some embodiments, tubular core member 720 may comprise a distal tubular core member and a proximal tubular core member. The distal end of the proximal tubular core member may be joined to the proximal end of flexible coupler 722, while the proximal end of the distal tubular core member is joined to the distal end of flexible coupler 722. In still other embodiments, tubular core member 720 and flexible coupler 722 are integrally formed such as by providing core member 720 with a plurality of transverse slots as is described elsewhere herein.

In some clinical scenarios, it may be desirable for flexible coupler 722 to be more flexible than tubular core member 720, while still demonstrating properties strong enough to resist deformation under tensile loads. Flexible coupler 722 may be constructed from materials, such as polymers, multiple polymers, Nitinol, stainless steel, etc. In certain embodiments, flexible coupler 722 may be created by piercing, slotting, grooving, scoring, cutting, laser cutting or otherwise removing material from a tubular body to increase flexibility. Alternatively, a flexible coupler 722 may be integrally formed with tubular core member 720 using any of the above mentioned patterns. In another embodiment, flexible coupler 722 is created by thinning a portion of tubular core member 720 to create a more flexible region. Flexible coupler 722 may also be deformed into a serrated or bellows shape without removing any material from the tubular body. Any of the other methods discussed above to increase the flexibility of tubular core member 720 may also be applied.

In some embodiments, a flexible section 738 of tubular core member 722 may be configured to be more flexible than a proximal section of tubular core member 722. In some aspects, flexible section 738 is positioned distal to flexible coupler 722. The length of flexible section 738 may measure from about 5 mm to about 50 mm, from about 10 to about 30 mm, or from about 20 to about 40 mm. In other embodiments, the flexible distal section may be less than 5 mm or greater than 50 mm.

Figure 33B:
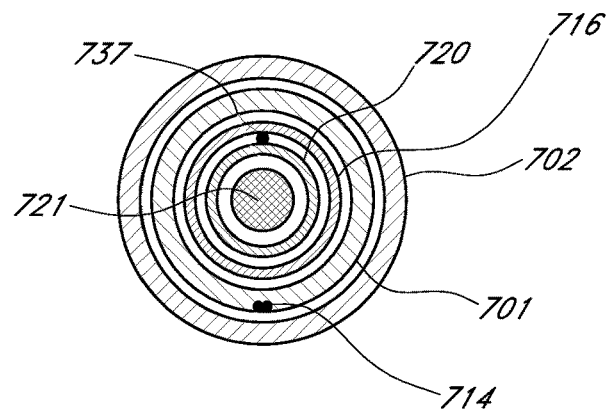
Figure 33C:
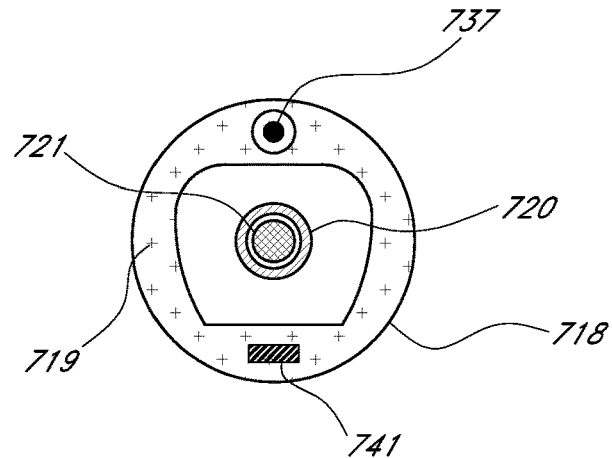
Figure 33D:
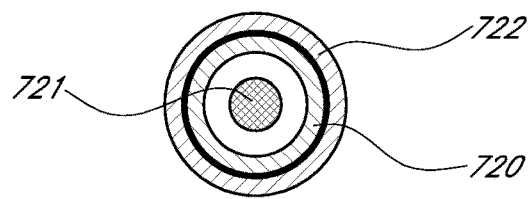

FIGS. 33B-D illustrate cross sections at various positions along the dual filter system depicted in FIG. 33A. FIG. 33B illustrates a cross section of filter system 700, proximal to proximal filter assembly 704. Guidewire 721 is disposed through a lumen defined by tubular core member 720, and tubular core member 720 is disposed through a lumen defined by distal shaft 716. In certain embodiments, at least a portion of distal sheath 718 may be articulated via pull wire 737. FIG. 33B shows that at least a portion of pull wire 737 may be disposed through distal shaft 716, but external to tubular core member 720. In some embodiments, at least a portion of pull wire 737 may pass through a lumen embedded in at least a portion of the distal shaft wall or distal sheath wall. In FIG. 33B, a portion of distal shaft 716 may be disposed through a lumen defined by proximal shaft 701. Proximal filter frame 714 may extend through a lumen embedded in at least a portion of the proximal filter shaft wall 701. Proximal filter shaft 701 is disposed through a lumen defined by proximal sheath 702.

FIG. 33C depicts a cross section distal to the cross section depicted in FIG. 33B through distal sheath 718. Distal sheath is illustrated in a simplified form, but typically will include all of the deflection mechanisms of FIGS. 9A-9E, discussed above. FIG. 33C shows guidewire 721 disposed through a lumen defined by tubular core member 720. At least a portion of tubular core member 720 is disposed through a lumen defined by distal sheath 718. As depicted in 33C, at least a portion of distal sheath 718 may be provided with a reinforcement such as an embedded coil or braid 719 to improve torqueing capabilities. In some embodiments, the entire length of distal sheath 718 may comprise a reinforcing element such as a braid. Pull wire 737 may extend through a lumen extending through at least a portion of the distal sheath 718, and distal sheath spinal element 741 may extend through at least a portion of distal sheath 718. In some embodiments, the outer diameter of distal sheath 718 is substantially similar to the outer diameter of proximal sheath 702. In other embodiments, distal sheath 718 extends through a lumen defined by proximal sheath 702.

FIG. 33D depicts a cross section distal to the cross-section depicted in FIG. 33C. FIG. 33D shows guidewire 721 disposed through a lumen defined by tubular core member 720. Tubular core member 720 is coaxial with flexible coupler 722. In certain embodiments, the diameter of flexible coupler 722 may be larger than the diameter of tubular core member 720. In other embodiments, flexible coupler 722 may have the same diameter as tubular core member 720. In still other embodiments, the diameter of flexible coupler 722 may be smaller than the diameter of tubular core member 720. In certain embodiments, the flexible coupler may not be a separate component.

Figure 34A:
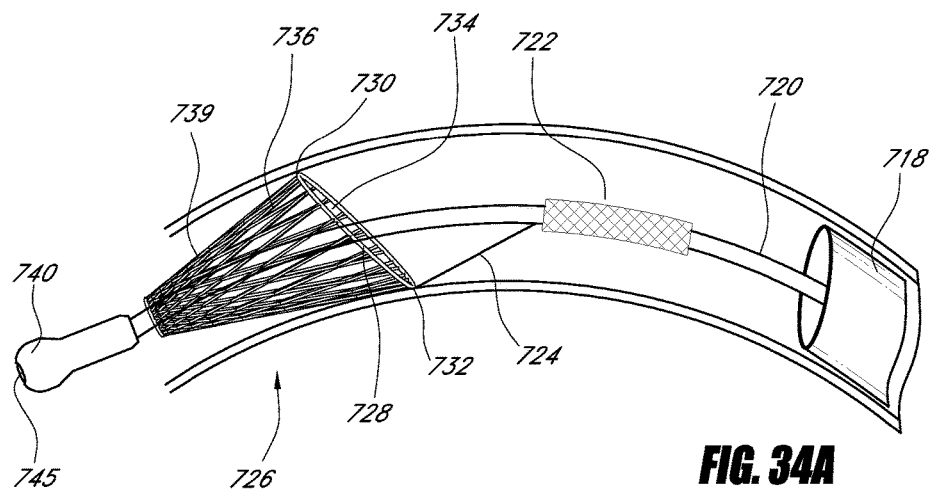
FIGS. 34A-C illustrate a filter system with a flexible coupler.
Figure 34B:
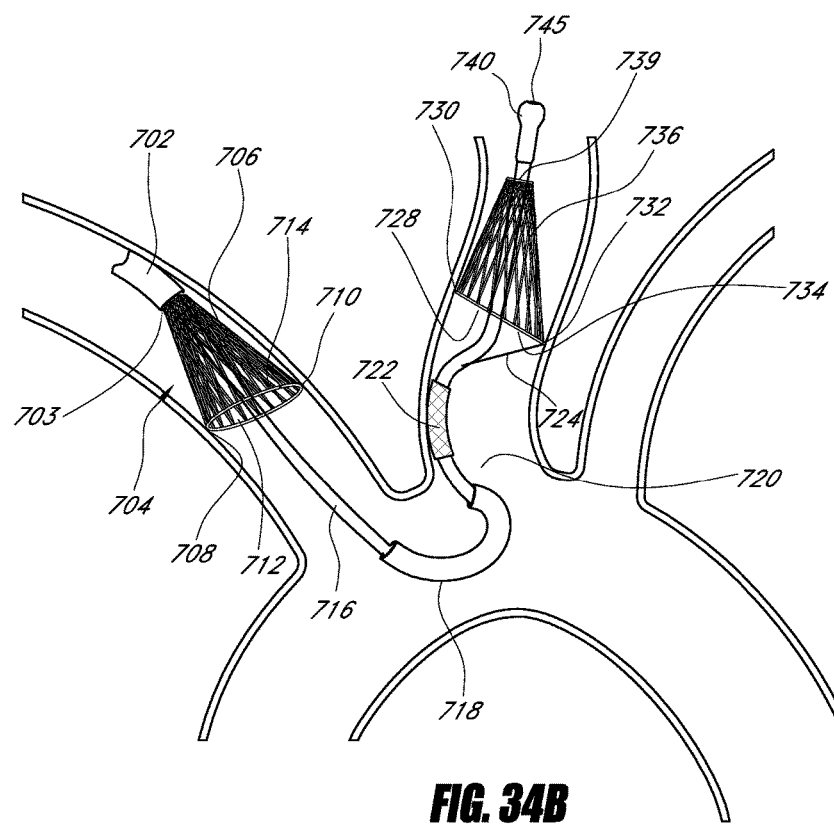
Figure 34C:
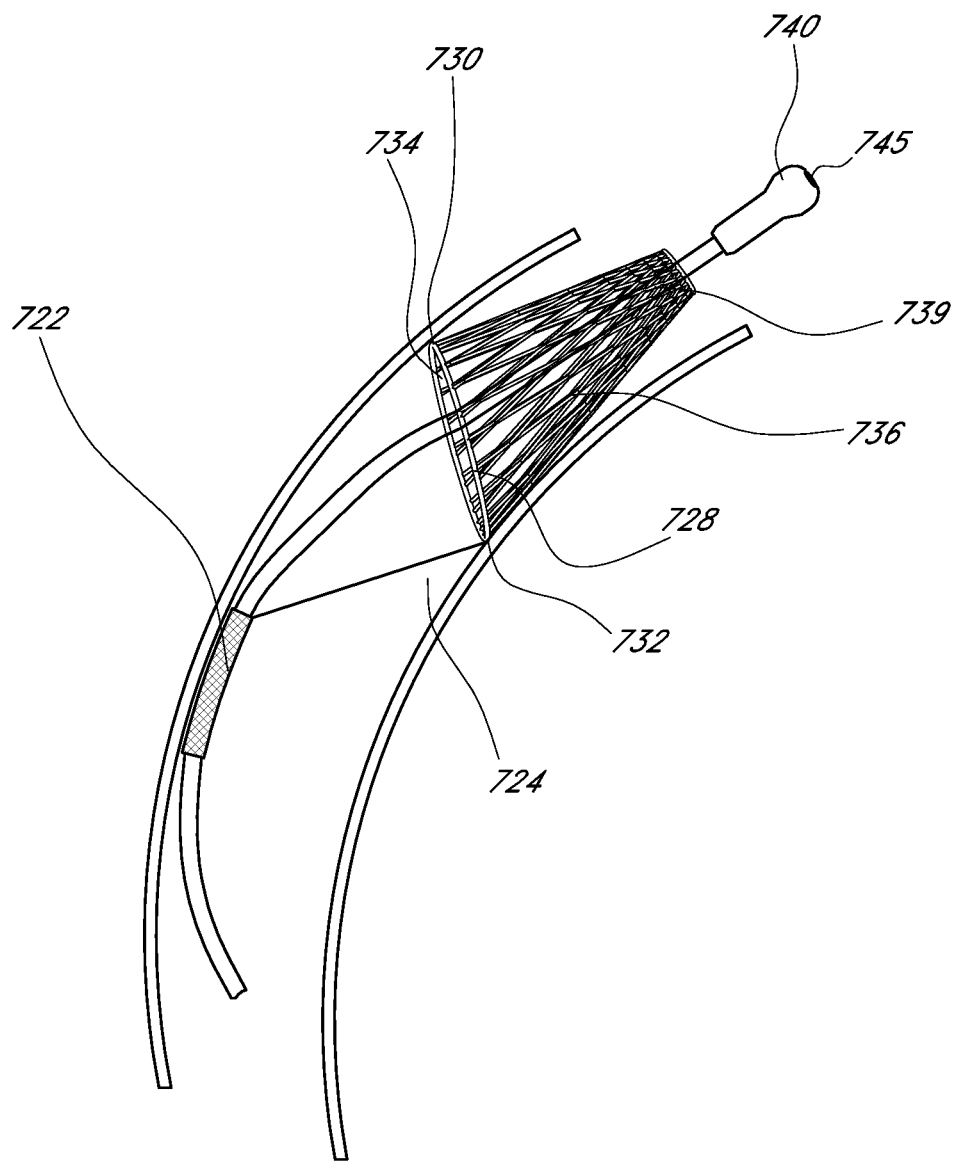

As shown in FIGS. 34A-C, a tubular core member 720 coupled with a flexible coupler 722 has the advantage of providing improved column strength along a substantial length of the filter system 700, but providing the flexibility necessary for distal filter assembly 726 to position itself independent of the position of distal shaft 716. Flexible coupler 722 allows distal filter frame element 728 to create a better seal against the vessel wall to help prevent embolic debris from flowing between distal filter 736 and the vessel wall.

A filter system having a flexible coupler 722 is deployed similarly to the method described in FIGS. 2A-2D. In one embodiment, as distal sheath 718 is advanced into the left common carotid artery, tubular core member 720 is advanced distally relative to distal sheath 718. FIG. 34B illustrates filter system 700 after tubular core member 720 is advanced into the left common carotid artery. Distal filter 736 expands and flexible coupler 722 deflects relative to filter system 700 such that distal filter frame element 728 is circumferentially apposed to the vessel wall. Strut 724 may be proximally retracted as desired to tilt the frame element 728 to improve the fit of the distal filter 736 within the vessel.

In certain embodiments, the stiffness of tubular core member 720 may be further reduced during use by the operator by withdrawing the guidewire until the distal end of the guidewire is proximal to flexible coupler 722 such that the guidewire is no longer disposed within flexible coupler 722, thus reducing stiffness.

Figure 35A:
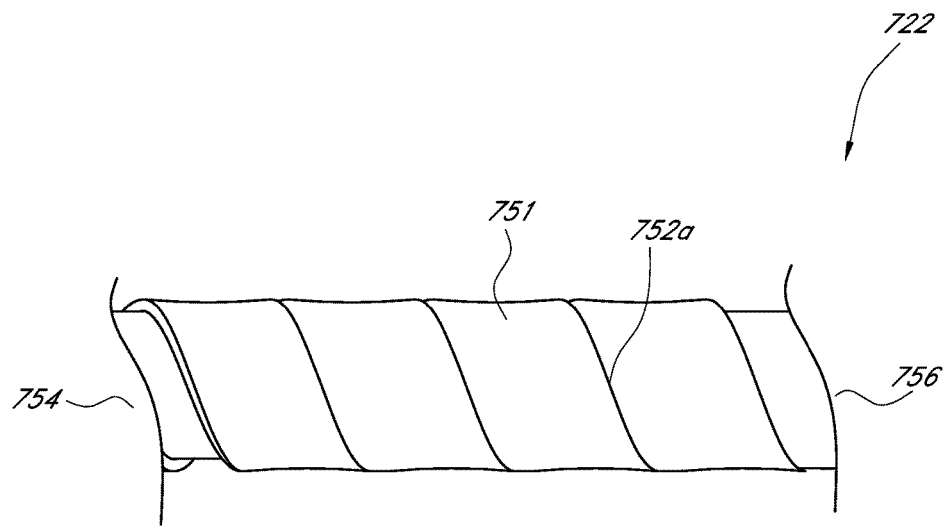
FIGS. 35A-E illustrate alternate designs for a flexible coupler.
Figure 35B:
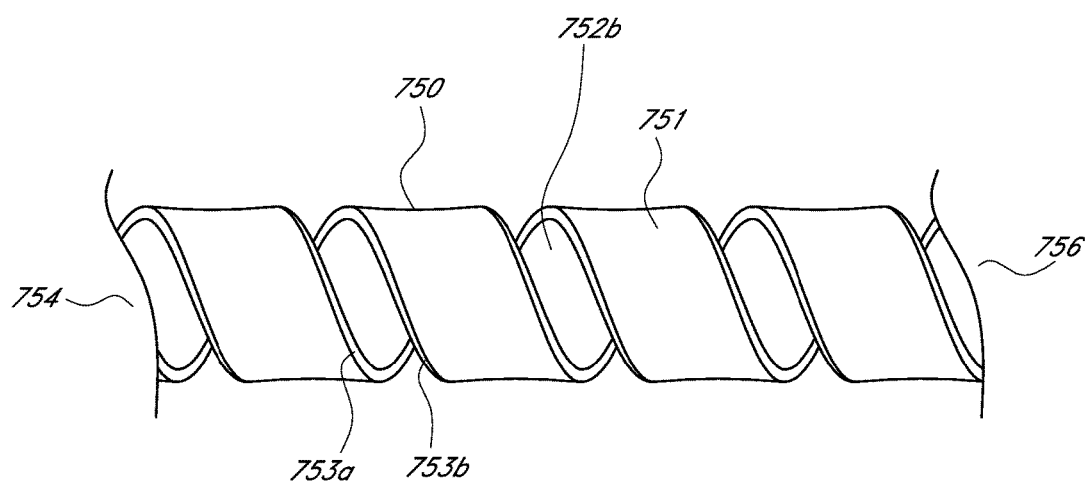

FIGS. 35A-B illustrate a tubular body 750 suitable for use as a flexible coupler 722. A tubular body 750 having a proximal end 754 and a distal end 756 may be formed by wrapping a ribbon or wire around a mandrel or by laser cutting a tube with a spiral pattern to form a coil. The width of spaced regions 752*a,b* between each adjacent coil loop 751 may be different in an unstressed orientation depending on the desired properties. In some embodiments, it may be desirable to provide greater flexibility, in which case, spaced region 752*b* should be wider to allow for a greater range of movement. In certain clinical scenarios, it may be desirable to provide smaller spaced regions 752*a* between each coil portion 751 to help prevent a first edge 753*a* and a second edge 753*b* of each coil portion 751 from dislodging plaque from the vessel wall or damaging the vessel wall. In an alternate embodiment, a flexible coupler 722 having wider spaced regions 752*a* between each coil portion 751 may be covered by a thin sheath such as shrink wrap tubing to provide flexibility and protect the vessel wall from flexible coupler 722.

Figure 35C:
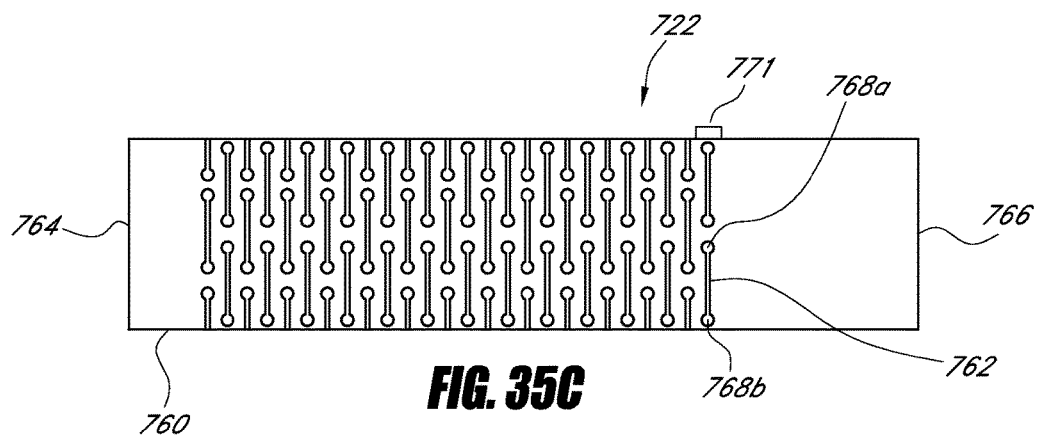

In FIG. 35C, a tubular body 760 having a proximal end 764 and a distal end 766 is laser cut with a plurality of slots 762, each slot 762 having a first end 768*a* and a second end 768*b*. In some embodiments, two or more slots 762 form a circumferential ring 771 around flexible coupler 722. In several embodiments, a plurality of circumferential rings 771 is laser cut into a tubular body 760. The plurality of circumferential rings 771 may be staggered such that a first slot of a first circumferential ring is misaligned from a first slot of a second circumferential ring. The plurality of slots 762 are configured such that flexible coupler 722 flexes angularly while retaining good torque resistance and tensile displacement resistance.

Figure 35D:
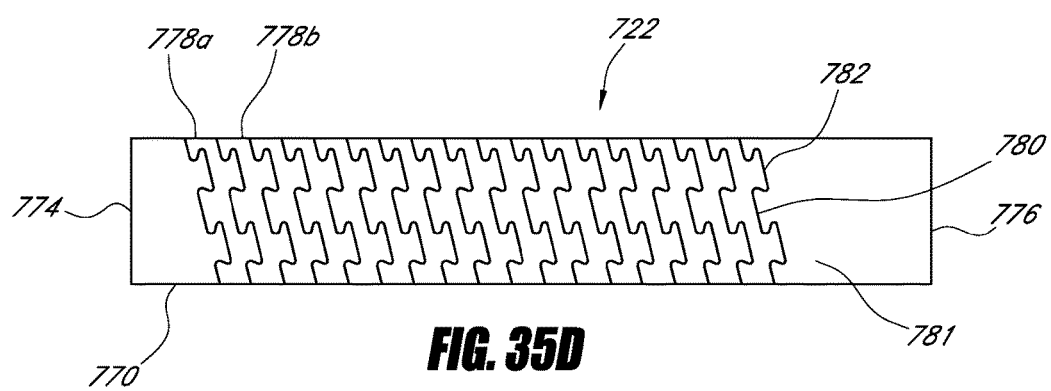
Figure 35E:
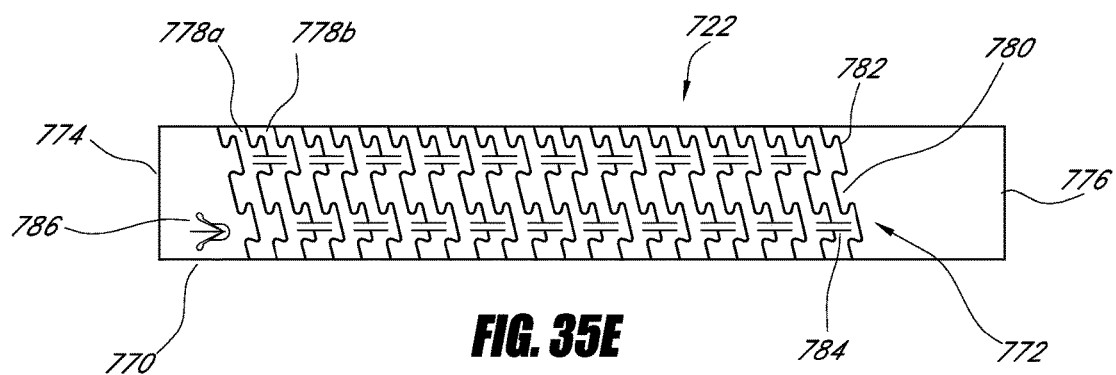

FIG. 35D depicts a flexible coupler 722 constructed from a tubular body 770 having a proximal end 774 and a distal end 776. Tubular body 770 is laser cut with a spiral pattern, the spiral pattern having a plurality of interlocking ring portions, wherein a first interlocking ring portion 778*a* interlocks with a complementary second interlocking ring portion 778*b*. Flexible coupler 722 has an interlocking pattern designed to resist axial deformation (stretching) when placed in tension. FIG. 35E illustrates flexible coupler 722 also having interlocking ring portions 778. In this embodiment, an axial element 784 is positioned across an interlocking feature 782 to improve the axial stiffness of flexible coupler 722 when subject to tensile loading.

Although the above mentioned embodiments were discussed in connection with a tubular core member, the same properties may be applied to any other guiding member. The guiding member may incorporate any of the above mentioned properties alone, or in combination, to manipulate flexibility and column strength along the guiding member shaft. The embodiments may also be used in connection with the proximal filter or any other catheter-based system.

In certain clinical scenarios, it may be desirable for the filter opening to circumferentially appose the vessel wall. This helps prevent debris from flowing past the filter. In a straight lumen, a filter can achieve good apposition with the vessel wall, thus preventing plaque or blood clots from flowing past the filter when it is deployed in a vessel. In contrast, when a filter is deployed in a curved lumen, the filter frame element can settle into a number of different rotational orientations in the lumen. In some clinical scenarios, when the filter is deployed in a curved lumen, it is possible for the filter frame element to pull away from the vessel wall particularly on the inner radius thus leading to poor apposition and blood leakage past the filter.

In current settings, practitioners may seek to overcome this poor positioning by using contrast injections and fluoroscopic imaging in one or more views. The filter is then either re-sheathed and redeployed or rotated or repositioned without re-sheathing, a process that can dislodge plaque from the vessel wall or otherwise damage the vessel. Neither of these solutions is satisfactory due to the extended procedure time and the increased possibility of vessel damage due to increased device manipulation.

In certain scenarios, it may be advantageous to add a tethering member to a filter assembly. FIGS. 36A-E illustrate tethering member 842 attached to proximal filter assembly 804. Tethering member 842 is configured to draw proximal filter frame element 814 closer to the vessel wall in order to form a seal with the inner surface of the vessel. Proper apposition of proximal filter assembly 804 relative to the vessel wall prevents debris from flowing past proximal filter assembly 804. This can be achieved with a flexible tethering member (e.g. monofilament polymer, braided polymer, suture, wire, etc.) or with a rigid or semi-rigid member such as nitinol, thermoplastic, stainless steel, etc.

Figure 36A:
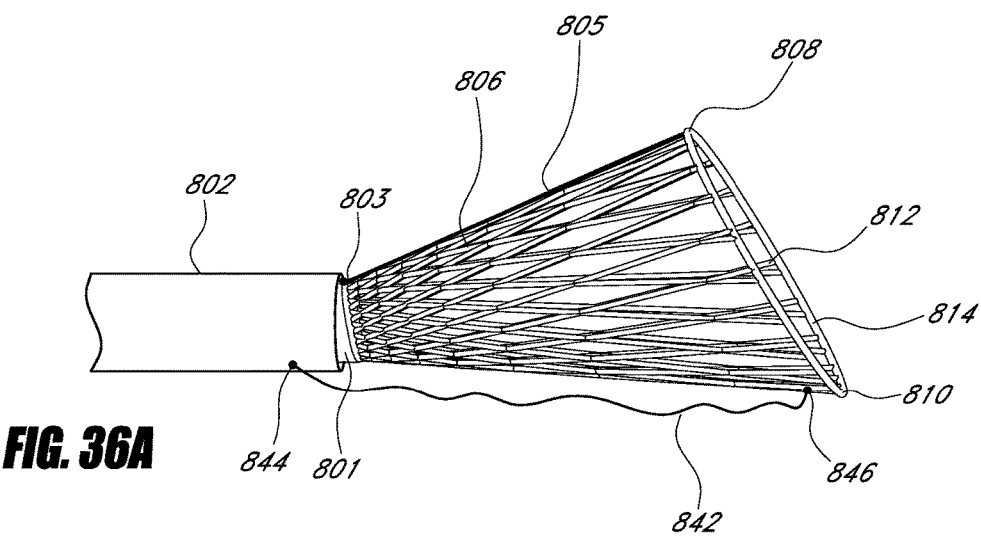
FIGS. 36A-C illustrate a method of using a tethering member.
Figure 36B:
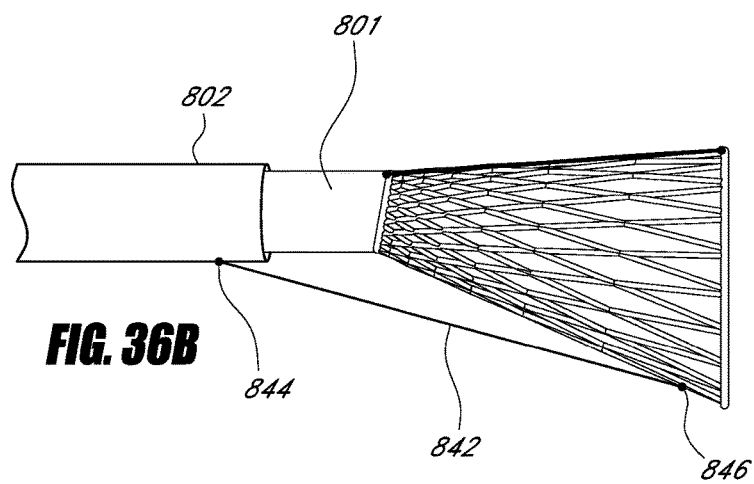
Figure 36C:
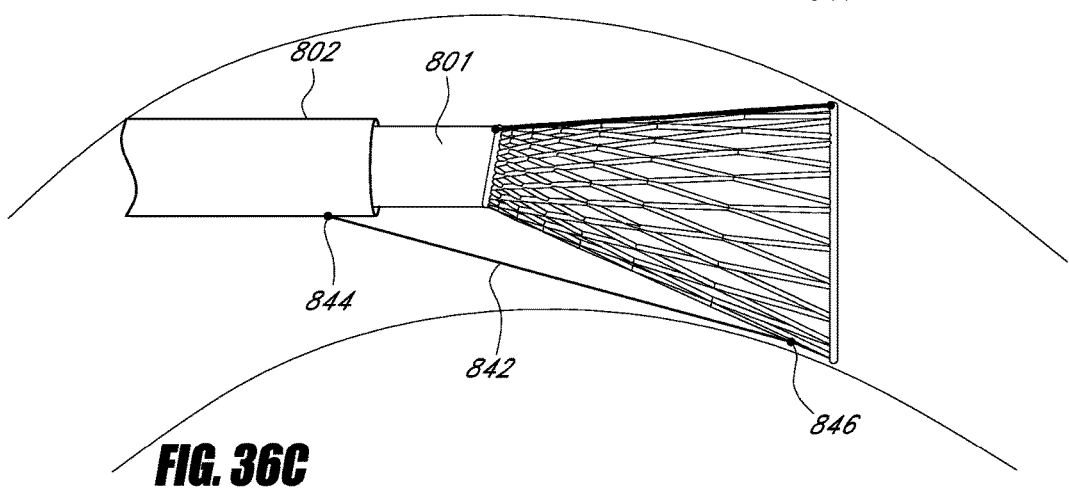

Tethering member 842 has a first end 844 and a second end 846. In FIG. 36A, the first end 844 of tethering member 842 is affixed to proximal sheath 802, while the second end 846 of tethering member 842 is affixed to proximal filter assembly 804. In some embodiments, tethering member 842 is affixed to filter frame element 814; while in other embodiments, tethering member 842 is affixed to proximal filter 806. FIGS. 36B-C illustrate how tethering member 842 laterally deflects the frame 814 and pulls filter frame element 814 toward the vessel wall when the operator retracts proximal sheath 802. Proximally retracting tethering member 842 allows the operator to control the deflection and angle of proximal filter frame element 814. In other embodiments, tethering member 842 can be actuated passively rather than actively (i.e. by the operator) by forming tethering member 842 from an elastic material or spring in order to elastically pull the edge of proximal filter frame element 814 toward the vessel wall.

In still other embodiments, the second end 846 of tethering member 842 may be attached to a feature disposed along proximal filter 806. For example, in FIG. 36E, the second end 846 of tethering member 842 is connected to a rib 848 formed on proximal filter 806. In still other embodiments, the first end 844 of tethering member 842 may be attached to an elongate member such as a pull wire slidably disposed along the length of the catheter system to a control actuator in the control handle. This allows the operator to control the deflection of proximal filter frame element 814 independently from proximal sheath 802.

Figure 36D:
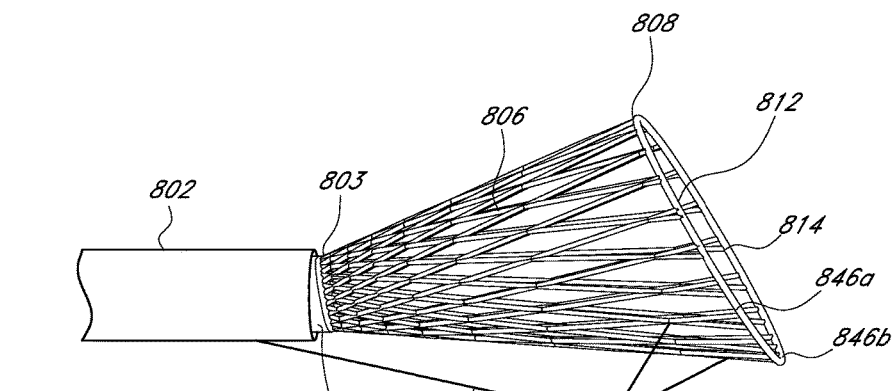
FIGS. 36D-E illustrate attachment points for a tethering member.
Figure 36E:
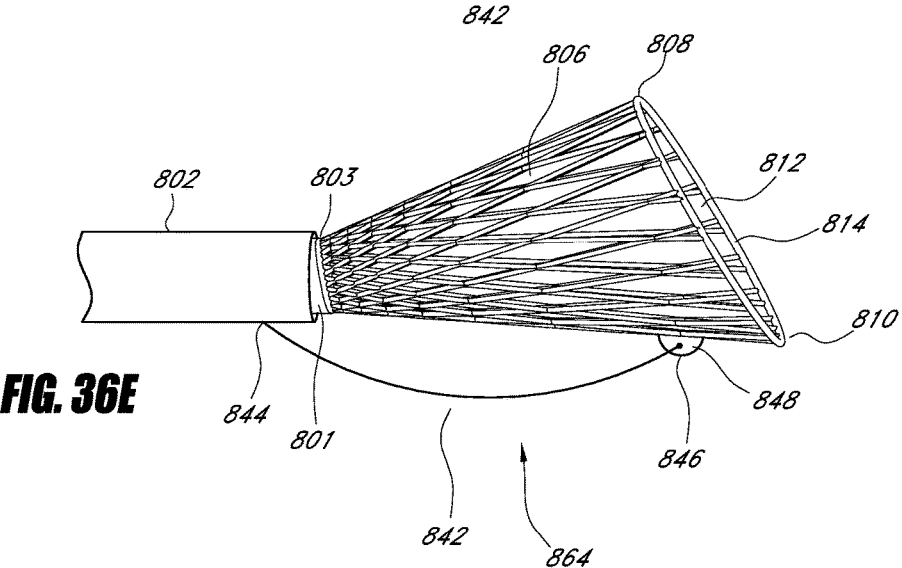

In certain embodiments, it may be preferable to attach a distal end of tethering member 842 to a single location on proximal filter assembly 804. Alternatively, as shown in FIG. 36D, it may be preferable to attach the distal end of tethering member 842 to two or more positions on proximal filter assembly 804.

Figure 37A:
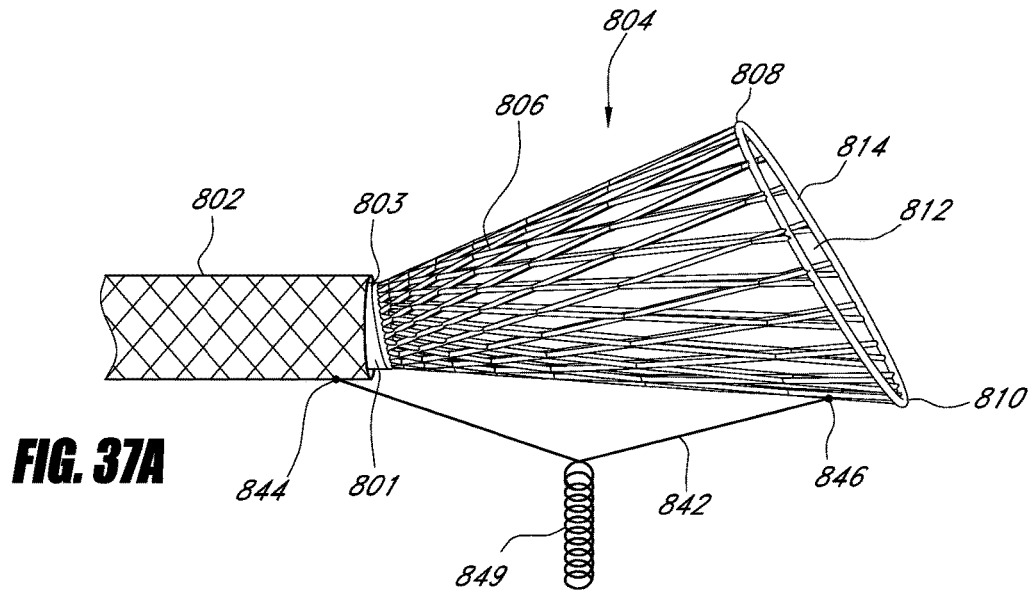
FIGS. 37A-D illustrate multiple embodiments for a tethering member.
Figure 37B:
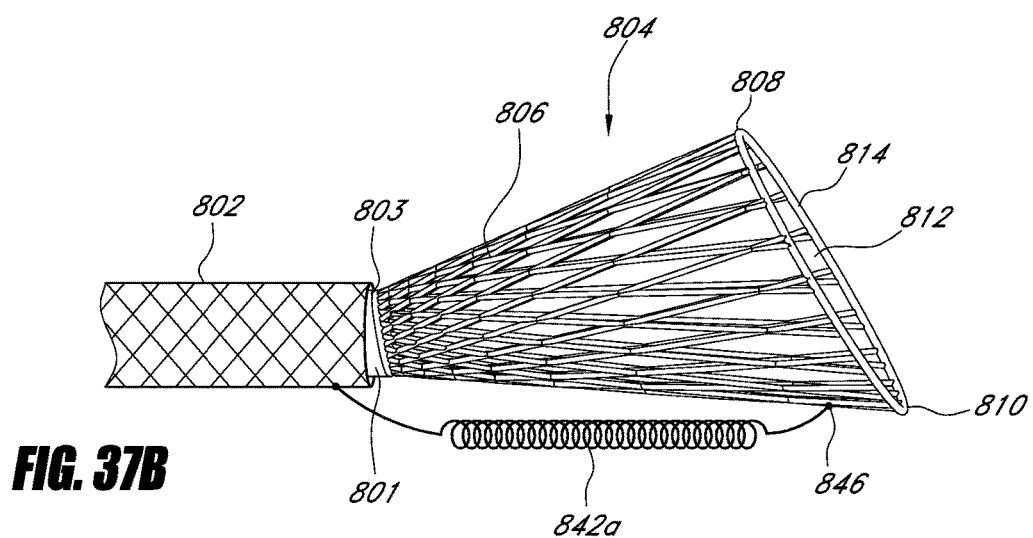
Figure 37C:
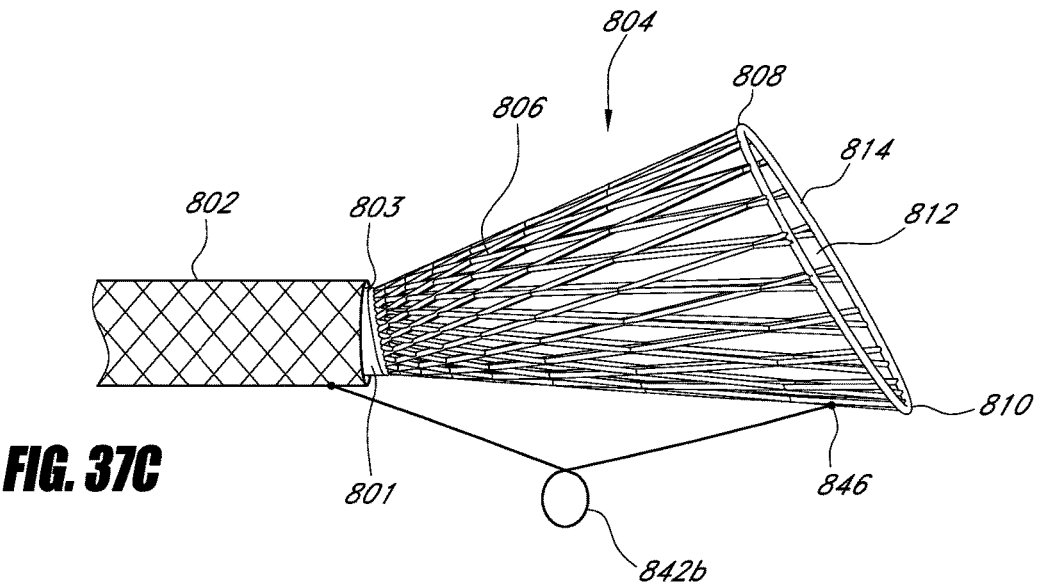
Figure 37D:
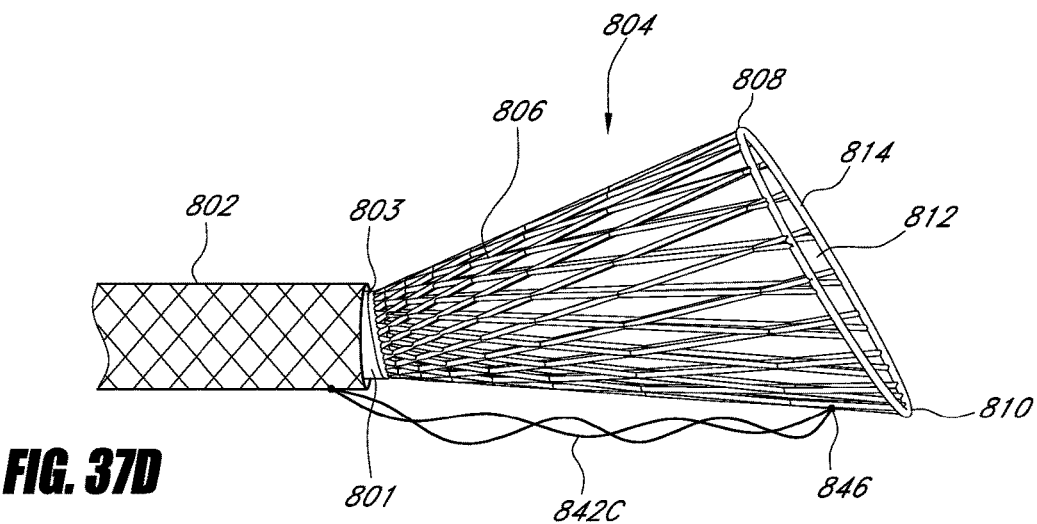

In order to facilitate sheathing and to minimize tangling when proximal filter assembly 804 is collapsed into proximal sheath 802, tethering member 842 may be twisted to form a coil 849, as shown in FIG. 37A. Twisted portion 849 retracts and stays out of the way when proximal filter assembly 804 is sheathed, and twisted portion 849 will untwist and straighten as the operator deploys proximal filter assembly 804. The design is also helpful for controlling the slack in tethering member 842 during sheathing and unsheathing. Tethering member 842 may be formed from a heat deformable polymer and applying heat to deform the polymer into a twisted configuration. Tethering member may alternatively be formed from nitinol or any other material having suitable properties. In other embodiments, it may be preferable for tethering member 842 to form a coil (FIG. 37B), pre-formed to particular shapes (FIG. 37C), or have two or more tethering members (FIG. 37D). One or more tethering members may be formed into any other design that may decrease the likelihood that tethering member 842 will become tangled with other catheters or devices.

Although the previously discussed tethering members have been discussed in connection with proximal filter assemblies, a tethering member may be used in connection with a distal filter, other filter devices, or any intraluminal device that may desirably be laterally displaced, tilted or otherwise manipulated into a desired orientation, such as to improve alignment including improving apposition with a vessel wall.

In some clinical scenarios, it may be desirable to place a single filter in a blood vessel. Any of the above mentioned features of the dual filter embodiments may be applied to the single filter embodiments described below, including, but not limited to, filter design, sheath articulation, or guiding member flexibility or column strength. In addition, filter systems described herein can be utilized in connection with a variety of intravascular interventions. The embodiments described below will be discussed in connection with a TAVI procedure, but the filter systems may be used with other intravascular or surgical interventions such as balloon valvuloplasty, coronary artery bypass grafting, surgical valve replacement, etc. and should not be construed as limited to the TAVI procedure.

In certain situations, it may be desirable to position the filter in the aorta, distal to the aortic valve but proximal to the brachiocephalic artery ostium, such that the entire arterial blood supply can be filtered. The aortic filter may also be positioned in the aorta, between the right brachiocephalic artery ostium and the left carotid artery ostium. In other scenarios, the aortic filter may be positioned between the left carotid artery ostium and the left subclavian artery ostium, while in still other clinical situations may make it preferable to position the aortic filter in the descending aorta, distal to the left subclavian artery ostium. In some cases, an aortic filter can be positioned in the aorta in combination with brachiocephalic and left carotid artery filters in order to capture all embolic debris.

An aortic filter can be positioned at various locations along a catheter system. In one embodiment, the aortic filter can be positioned on a catheter separate from the TAVI or pigtail catheter and inserted through the left or right brachial artery or the right or left femoral artery. Using a separate aortic filter catheter decreases the overall diameter of the TAVI catheter and allows the operator to position the aortic filter independently from aortic valve. Further, the aortic filter will not dislodge plaque along the vessel wall when the TAVI catheter is repositioned or rotated.

In another embodiment, the aortic filter can be positioned on the TAVI catheter shaft, proximal to the valve prosthesis. To decrease the size of the overall catheter system, the diameter of the TAVI catheter system proximal to the valve prosthesis may be reduced in size. This embodiment decreases the number of total devices in the operating environment, thus decreasing the likelihood that devices will get tangled.

In yet another embodiment, the aortic filter may be positioned on the TAVI introducer. This embodiment enables the operator to position the aortic filter independently from the position of the TAVI catheter. The filter is also less likely to dislodge plaque along the vessel wall when the TAVI catheter is repositioned or rotated. Introducing the aortic filter on the TAVI introducer also decreases the total number of catheters into the operating environment.

In still another embodiment, the aortic filter is positioned on a pigtail catheter shaft, proximal to the pigtail. Affixing the aortic filter to the pigtail catheter does not increase the overall diameter of the TAVI system or add any additional catheters into the operating environment.

In one embodiment, the aortic filter is positioned on an extended pigtail introducer sheath. This embodiment enables the operator to position the aortic filter separately from the location of the pigtail without adding any additional catheters into the operating environment. Positioning the aortic filter on the pigtail introducer sheath also does not increase the overall diameter of the TAVI system. Further, the aortic filter will not dislodge plaque along the vessel while when the pigtail and/or TAVI catheter is repositioned or rotated.

Various methods can be used to perform a TAVI procedure in connection with an aortic filter. In one method, the aortic filter is positioned as early as possible in the procedure at any location in the aorta previously described, and the aortic filter may be deployed using any of the above mentioned devices. The TAVI catheter may then be inserted through the filter and the TAVI implantation is performed. Afterward, the TAVI catheter and aortic filter are removed.

In an alternative method, a guidewire is positioned through the aorta and the pigtail catheter is inserted into the aorta. A TAVI catheter can then be advanced to a position just proximal of where the aortic filter will be deployed. The aortic filter may be deployed at any position described above. Using any of the previously discussed embodiments, a catheter carrying an aortic filter deploys an aortic filter in the aorta. The aortic filter also forms a seal against both the TAVI catheter and the vessel wall such that debris cannot flow past the filter. After the aortic filter is deployed, the TAVI catheter is advanced to the implant location and the implant procedure is performed. When the procedure is over, the TAVI catheter is withdrawn just proximal to the filter such that the operator can retrieve the aortic filter. The aortic filter, TAVI, and pigtail catheters are then all withdrawn from the operating environment. These steps are not limited to the order in which they were disclosed. For example, the TAVI catheter may be advanced to the implant location before the aortic filter is deployed.

Figure 38A:
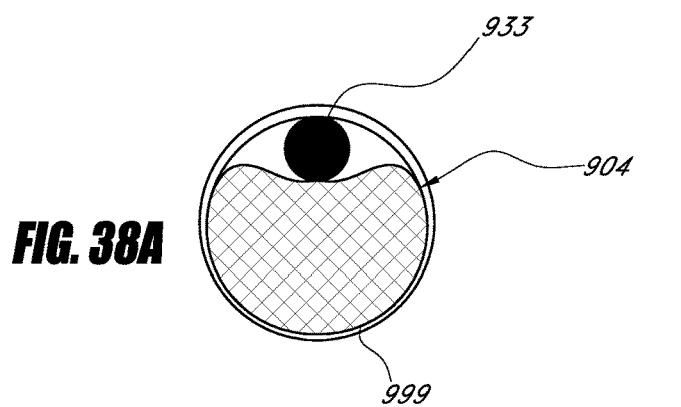
FIGS. 38A-D illustrate multiple embodiments for an aortic filter designed to form a seal around a catheter.

FIG. 38A depicts a TAVI catheter 933 that is deployed across an aortic filter assembly 904 in the aorta 999. In some scenarios, aortic filter assembly 904 may not fully appose the TAVI catheter shaft, thus leaving room for debris to flow between the TAVI catheter 933 and the vessel wall. In these scenarios, it may be preferential to configure aortic filter assembly 904 to appose TAVI catheter 933 and prevent substantially all debris from flowing past aortic filter assembly 904 without significantly degrading filter capture performance. It may also be preferential to modify aortic filter assembly 904 in scenarios where TAVI catheter 933 passes through aortic filter assembly 904.

Figure 38B:
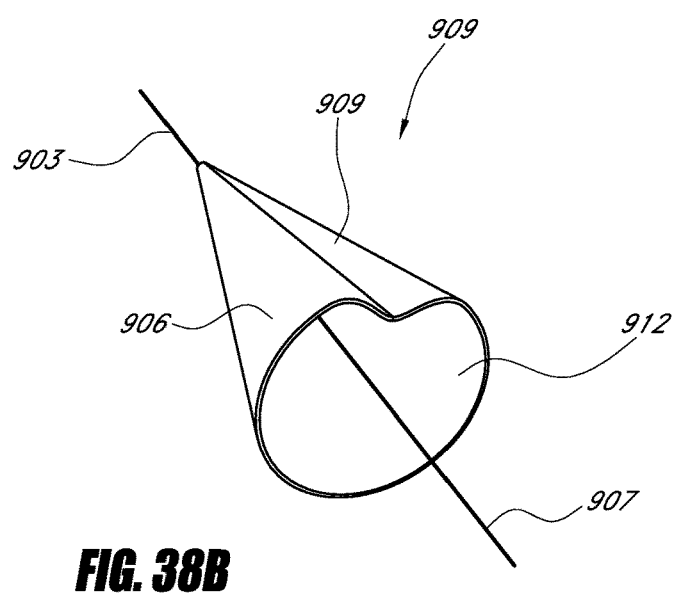

FIG. 38B illustrates an aortic filter assembly 904 designed to pass over a guidewire 907 or other guiding member. Aortic filter assembly 904 may have a channel 909 on the exterior surface of aortic filter assembly 904. Channel 909 is constructed such that a TAVI deployment catheter or other catheter may pass through channel 909. The operator may also rotate aortic filter assembly 904 such that the TAVI catheter properly passes through channel 909. The control handle may indicate the rotational location of channel 909 help the operator correctly orient aortic filter 904. Alternatively, channel 909 may have at least one or two radiopaque markers to enable identification of channel 909 using fluoroscopy.

Figure 38C:
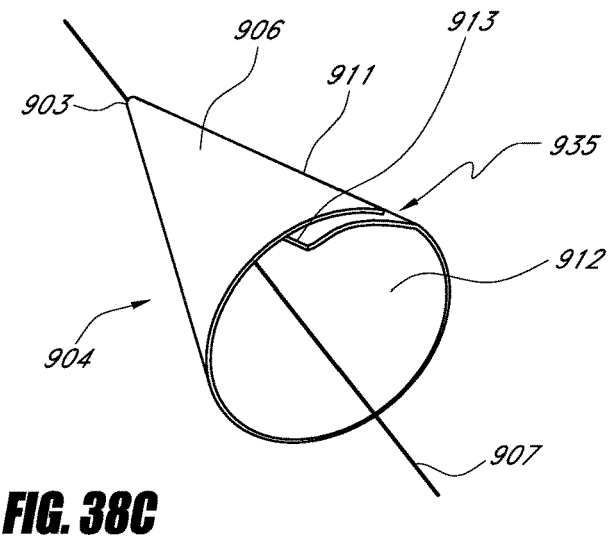

FIG. 38C depicts aortic filter assembly 904 having a leading edge 911 and a trailing edge 913. Aortic filter assembly 904 passes over a guidewire 907 or other guiding member. Leading edge 911 overlaps trailing edge 913 to form an overlapping portion 935. The control handle may indicate the location of overlapping portion 935 so the operator can torque aortic filter assembly 904 to position overlapping portion 935 over the TAVI or other catheter shaft. Overlapping portion 935 may have a radiopaque marker to allow the operator to monitor aortic filter placement under fluoroscopy.

Figure 38D:
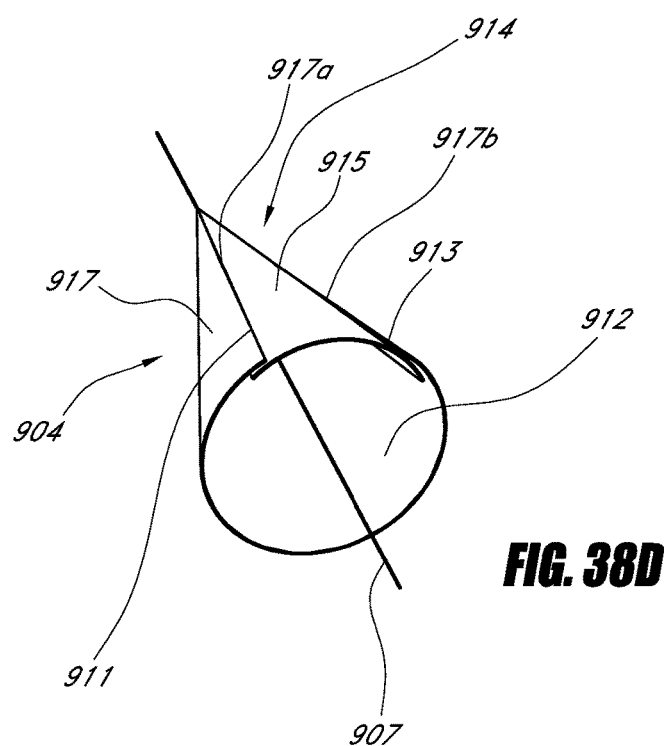

FIG. 38D depicts an aortic filter assembly 904 designed to pass over a guidewire 907 or other guiding member. Aortic filter 904 has a first filter portion 915 and a second filter portion 917, second filter portion 917 having a first edge 917a, and a second edge 917b. The first edge 917a and the second edge 917b of second filter portion 917 overlap first filter portion 915 to form a joint 914. The control handle may indicate the location of joint 914 so the operator can torque aortic filter assembly 904 to position joint 914 against the shaft of the TAVI catheter. As the operator advances a catheter-based device across aortic filter 904, second filter portion 917 caves inward such that joint 914 forms a seal around the catheter shaft. Aortic filter assembly 904 may include a radiopaque marker to allow the operator to identify joint 914 under fluoroscopy.

FIGS. 39 A-C depict an aortic filter device having two or three or four or more aortic lobes or filters. Each aortic filter lobe 904a,b,c is joined together along a first side 919 of each aortic filter lobe 904a,b,c. Aortic filter lobes 904a,b,c join together about a longitudinal axis of the aortic filter system. The aortic filter system is configured such that a TAVI catheter 933 or other catheter-based device may pass between a first aortic filter assembly 904b and a second aortic filter assembly 904c. The first and second aortic filters 904b,c forming a seal around the TAVI catheter 933, thus preventing debris from flowing past the aortic filter system.

FIG. 40A depicts generally conical aortic filter assembly 904 resembling an umbrella. Aortic filter 904 may pass over a guidewire 907 or other guiding member. Aortic filter assembly 904 has a plurality of self-expanding tines 923, each tine having a proximal end and a distal end. Each tine joins together at a first end 903 of aortic filter assembly 904. In addition, a filter portion 925 is suspended between tines 923. Filter portion 925 may be fairly inflexible or flexible to stretch over the TAVI catheter 933 or other catheter-based device. When an operator advances TAVI catheter 933 past aortic filter assembly 904, TAVI catheter 933 passes between a first tine 923 and a second tine 923 such that a filter portion 925 stretches over TAVI catheter 933 to form a seal between filter portion 925 and TAVI catheter 933.

Figure 40B:
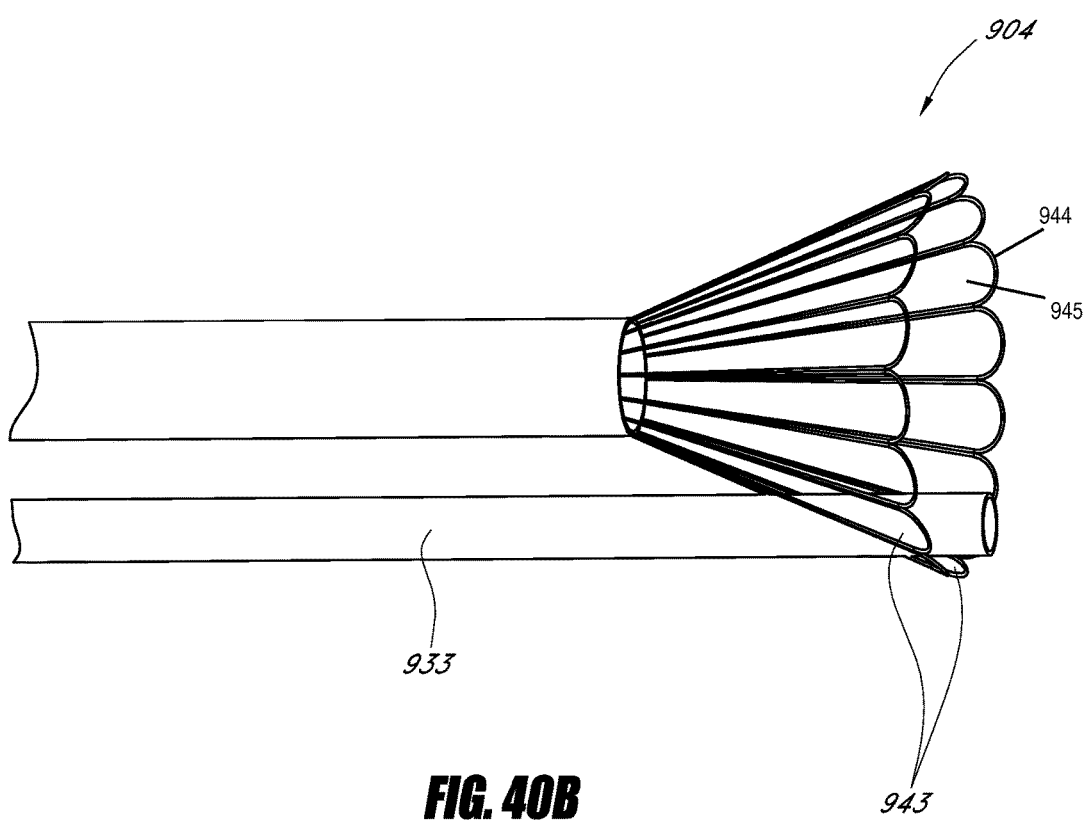

Alternatively, FIG. 40B depicts an aortic filter assembly 904 resembling a flower. In one embodiment, aortic filter assembly 904 has two or more petals 943 arranged in a circular array that allow TAVI catheter 933 or other catheter-based device to pass between petals 943. Petals 943 may overlap one another to create a seal between adjacent petals 943. Petals 943 also create a seal around TAVI catheter 933 as the catheter passes between petals 943. The shape of each petal 943 may include an arch to better accommodate the circular shape of the aorta. Each petal 943 may have a length between two to six centimeters. Although in some embodiments, the length may be less than in two centimeters; while in still other embodiments, the length may be greater than six centimeters. In one embodiment, the individual petals are comprised of a frame 944 that is covered with a filter element 945. The frame 944 may be constructed of a shape memory material such as Nitinol, or other material such as stainless steel, cobalt supper alloy (MP35N for example) that has suitable material properties. The filter element 945 may be constructed of a polyurethane sheet that has been pierced or laser drilled with holes of a suitable size. Other polymers may also be used to form the filter element, in the form of a perforated sheet or woven or braided membranes.

Thin membranes or woven filament filter elements may alternatively comprise metal or metal alloys, such as nitinol, stainless steel, etc.

Any of the aortic filter assemblies described above may also include frame element 914 formed from a material suitable to form a tight seal between aortic filter assembly 904 and TAVI catheter 933 or other catheter-based device as the filters fill under systolic blood pressure.

Figure 41A:
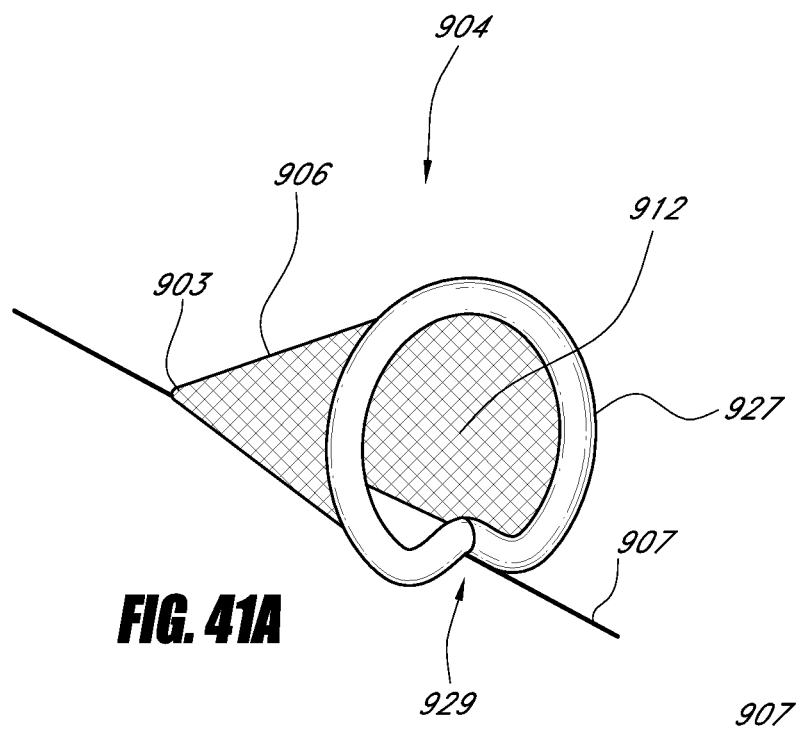
FIGS. 41A-B illustrate an aortic filter having an inflatable annulus.
Figure 41B:
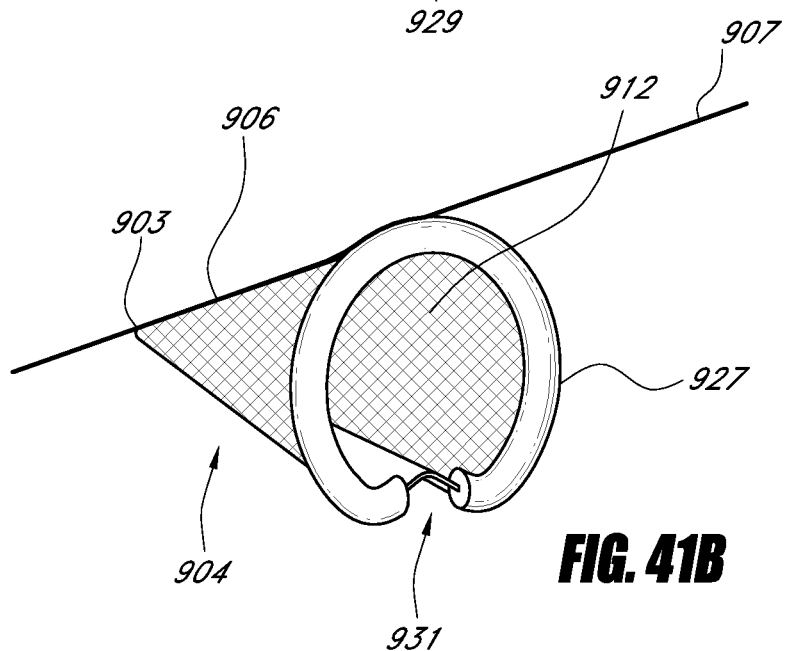

FIGS. 41A-B depicts an aortic filter assembly 904 having an inflatable portion 927 defining a distal opening 912 of aortic filter 906. In some embodiments, inflatable portion 927 forms a continuous ring. Inflatable portion 927 forms a seal against the vessel wall such that debris cannot pass between aortic filter assembly 904 and the vessel wall. Inflatable portion 927 may also form a seal against a TAVI catheter passed between aortic filter assembly 904 and the vessel wall.

As depicted in FIG. 41A, inflatable portion 927 and filter element 906 may form a channel 929 on an exterior surface of aortic filter assembly 904 through which a catheter-based device may pass. Channel 929 forms a seal against the catheter such that debris may not flow between the aortic filter assembly 904 and the catheter.

FIG. 41B illustrates an inflatable portion 927 having a gap 931 through which a catheter-based device may pass. Filter element 906 may also form a channel on the exterior surface of the aortic filter assembly 904 through which the catheter may pass.

In an embodiment which includes an inflatable annulus or other support, the inflatable support is placed in fluid communication with a source of inflation media by way of an inflation lumen extending throughout the longitudinal length of the catheter shaft. Once the filter has been positioned at a desired site, the annulus can be inflated by injection of any of a variety of inflation media, such as saline. The inflation media may thereafter be aspirated from the filter support, to enable collapse and withdraw of the filter. The inflation media may include a radiopaque dye to help the operator locate the inflatable annulus under fluoroscopy.

Although the filter systems described above were discussed in connection with a single filter system, the filter designs may also be used in connection with a dual filter system.

Figure 42:
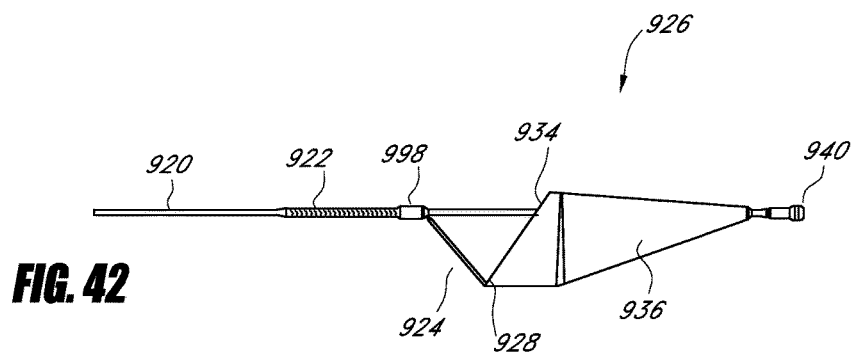
FIG. 42 illustrates a distal portion of an exemplary filter system.

FIG. 42 depicts one embodiment of a filter assembly that may be used in connection with any filter-based device, including the dual filter and single filter systems described above. Filter assembly 926 may comprise a filter membrane 936, a filter frame element 928, and at least one radiopaque marker. Filter membrane may 936 may be constructed from a polyurethane film or any other polymer or material exhibiting suitable properties. In some embodiments, a laser or other mechanism may be used to create at least one filter hole in the filter membrane through which blood may flow. The at least one filter hole is small enough such that a blood clot or piece of embolic debris exceeding a predetermined dimension cannot pass through. The filter membrane may be formed into a conical or other shape by heat sealing a first edge of the filter membrane to a second edge of the filter membrane, although other methods may be used to join a first edge of the filter membrane to a second edge of the filter membrane. In several embodiments, filter assembly 926 may also include flexible coupler 922.

A frame element 928 may be shaped from a Nitinol wire, but, as discussed in earlier paragraphs, the frame element may be shaped from any other suitable material or textured to exhibit desired properties. In some embodiments, at least one radiopaque marker is incorporated into filter assembly 926. In one embodiment, a 90/10 platinum/iridium coil marker is positioned around frame element 928 and bonded with an adhesive. Alternatively, other types of radiopaque markers may be integrated into or affixed to frame element 928. Other methods of affixing the radiopaque marker may also be used.

In several embodiments, filter assembly 926 includes a strut tubing 924. Strut tubing 924 may be constructed from PET heat shrink tube, polyimide tube, or any other material exhibiting suitable properties. In one embodiment, strut tubing 924 is affixed to one or more legs of frame element 928 with an adhesive, although other means for affixation may also be used. Additional mechanisms may also be used to reinforce the adhesive or other means of affixation. Alternatively, strut tube 924 may be slipped over one or more portions of the frame element 928 and may additionally be bonded in place.

In some embodiments, filter membrane 936 may be attached to frame element 928 by heat-sealing a first portion of filter membrane 936 to a second portion of filter membrane 936 to form a sleeve through which frame element 928 may pass. An adhesive may be used to reinforce the bond between the frame element and the filter membrane. Other mechanisms may also be used to affix frame element 928 to filter membrane 936. Additional mechanisms may also be used to reinforce the adhesive or other affixation mechanism.

In some embodiments, frame element 928 is attached to a filter shaft 920 via a stainless steel crimp 998, although other mechanisms may be used to affix frame element 928 to a filter shaft 920. Additional affixation methods may also be used to reinforce the stainless steel crimp 998 or other mechanism.

In several embodiments, a cannulated distal tip 940 having an atraumatic distal end with a guidewire exit port is joined to the distal end of filter shaft 920.

Figure 43:
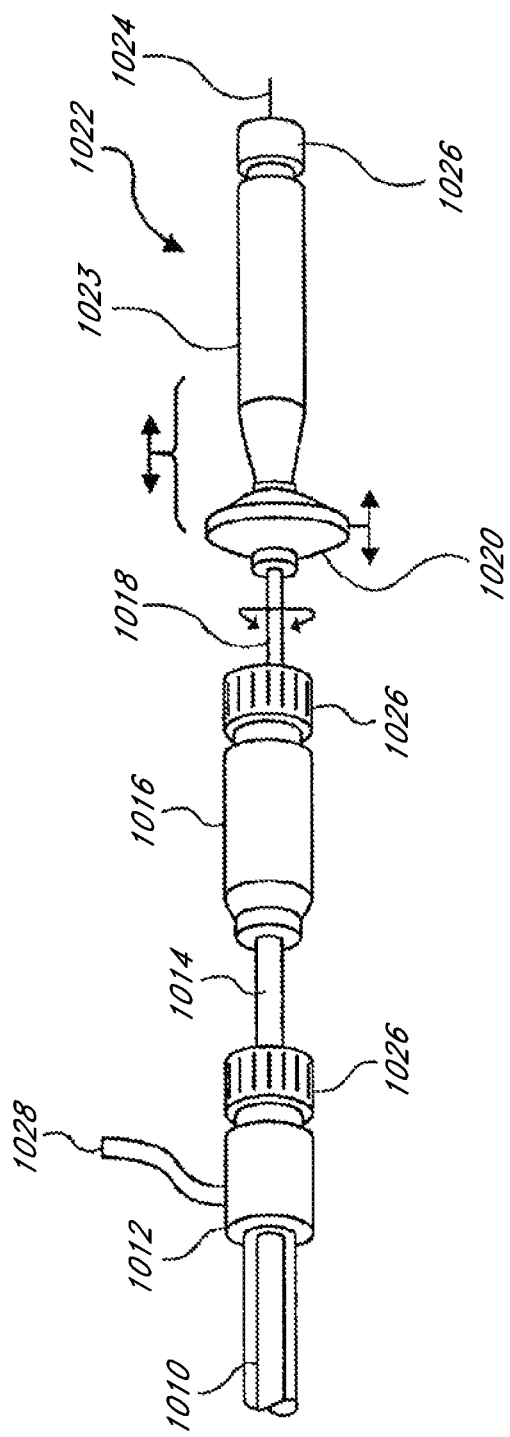
FIGS. 43-46 illustrate exemplary control handles of the blood filter systems.

FIG. 43 illustrates a proximal portion of an exemplary filter system. The portion shown in FIG. 43 is generally the portion of the system that remains external to the subject and is used to control the delivery and actuation of system components. Proximal sheath 1010 is fixedly coupled to proximal sheath hub 1012, which when advanced distally will sheath the proximal filter (as described herein), and when retracted proximally will allow the proximal filter to expand. The actuation, or control, portion also includes handle 1016, which is secured to proximal shaft 1014. When handle 1016 is maintained axially in position, the position of the proximal filter is axially maintained. The actuation portion also includes distal sheath actuator 1022, which includes handle 1023 and deflection control 1020. Distal sheath actuator 1022 is secured to distal shaft 1018. As described herein, the distal articulating sheath is adapted to have three independent degrees of motion relative to the proximal sheath and proximal filter: rotation, axially translation (i.e., proximal and distal), and deflection, and distal sheath actuator 1022 is adapted to move distal sheath 1018 in the three degrees of motion. Distal sheath 1018 is rotated in the direction shown in FIG. 43 by rotating distal sheath actuator 1022. Axial translation of distal sheath occurs by advancing actuator 1022 distally (pushing) or by retracting actuator 1022 proximally (pulling). Distal sheath 218 is deflected by axial movement of deflection control 1020. Movement of deflection control 1020 actuates the pull wire(s) within distal sheath 1018 to control the bending of distal sheath 1018. Also shown is guiding member 1024, which is secured to the distal filter and is axially movable relative to the distal sheath to deploy and collapse the distal filter as described herein. The control portion also includes hemostasis valves 1026, which in this embodiment are rotating.

Figure 44:
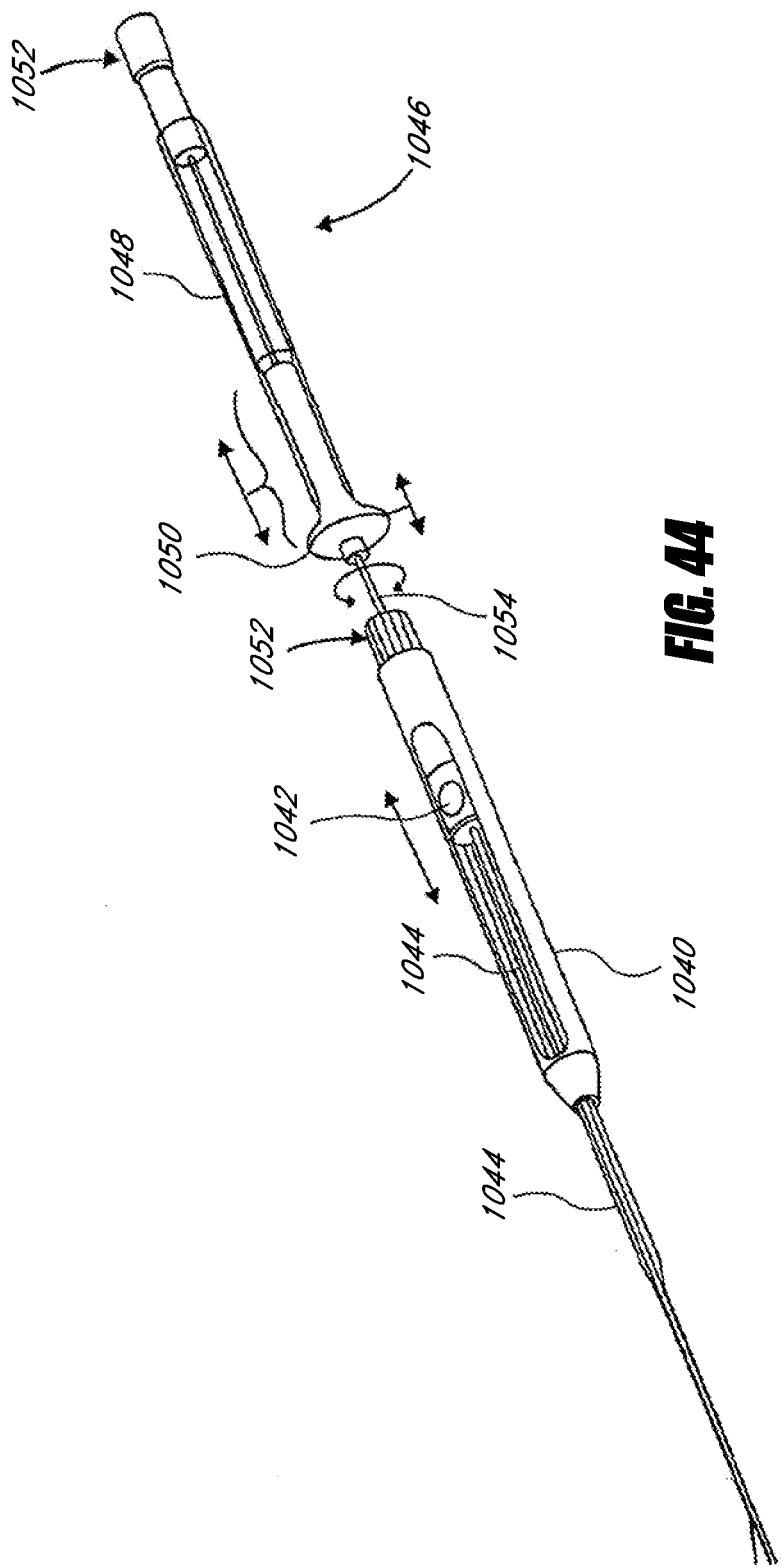

FIG. 44 illustrates an exemplary 2-piece handle design that can be used with any of the filter systems described herein. This 2-piece handle design includes distal sheath actuator 1046, which includes handle section 1048 and deflection control knob 1050. Deflection control knob 1050 of distal sheath actuator 1046 is secured to distal shaft 1054. Axial movement of distal sheath actuator 1046 will translate distal shaft 1054 either distally or proximally relative to the proximal filter and proximal sheath. A pull wire (not shown in FIG. 44) is secured to handle section 1048 and to the distal articulatable sheath (not shown in FIG. 44). Axial movement of deflection control knob 1050 applies tension, or relieves tension depending on the direction of axial movement of deflection control knob 1050, to control the deflection of the distal articulatable sheath relative to the proximal filter and proximal sheath 1044, which has been described herein. Rotation of distal sheath actuator 1046 will rotate the distal sheath relative to the proximal filter and proximal sheath. The handle also includes housing 1040, in which proximal sheath hub 1042 is disposed. Proximal sheath hub 1042 is secured to proximal sheath 1044 and is adapted to be moved axially to control the axial movement of proximal sheath 1044.

Figure 45:
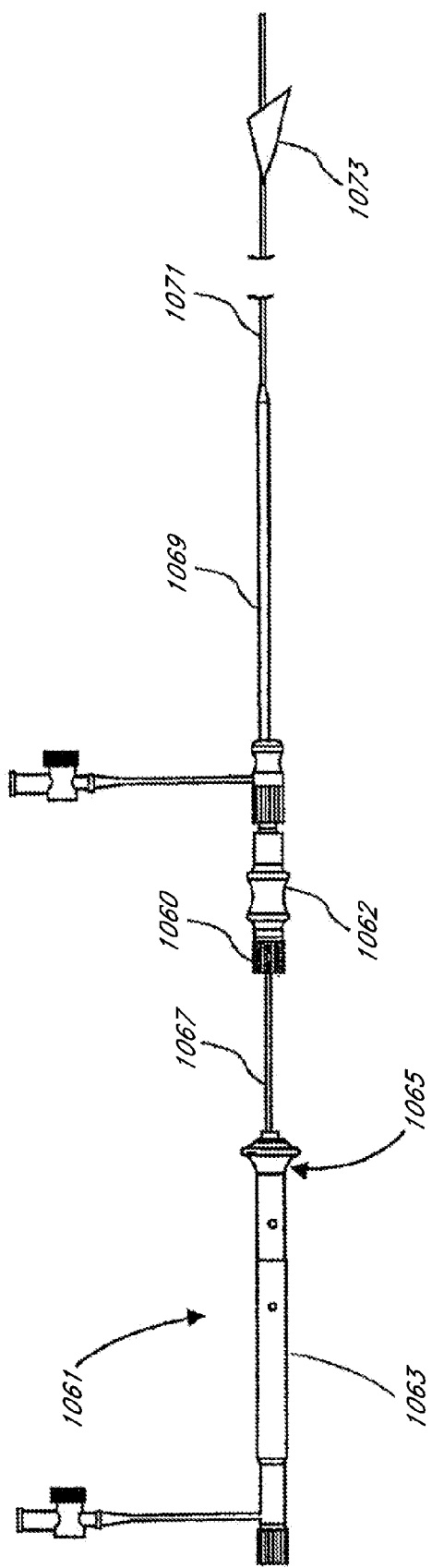

FIG. 45 illustrates another exemplary embodiment of a handle that can be used with any of the filter systems described herein. In this alternate embodiment the handle is of a 3-piece design. This 3-piece handle design comprises a first proximal piece which includes distal sheath actuator 1061, which includes handle section 1063 and deflection control knob 1065. Deflection control knob 1065 of distal sheath actuator 1061 is secured to distal shaft 1067. Axial movement of distal sheath actuator 1061 will translate distal shaft 1067 either distally or proximally relative to the proximal filter and proximal sheath. A pull wire (not shown in FIG. 45) is secured to handle section 1063 and to the distal articulatable sheath (not shown in FIG. 45). Axial movement of deflection control knob 1065 applies tension, or relieves tension depending on the direction of axial movement of deflection control knob 1065, to control the deflection of the distal articulatable sheath relative to the proximal filter and proximal sheath 1069. Rotation of distal sheath actuator 1061 will rotate the distal sheath relative to the proximal filter and proximal sheath 1069. The handle design further includes a second piece comprising central section 1060 which is secured to proximal shaft 1071. A third distal piece of this handle design includes housing 1062. Housing 1062 is secured to proximal sheath 1069. Housing 1062 is adapted to move axially with respect to central section 1060. With central section 1060 held fixed in position, axial movement of housing 1062 translates to axial movement of proximal sheath 1069 relative to proximal shaft 1071. In this manner, proximal filter 1073 is either released from the confines of proximal sheath 1069 into expandable engagement within the vessel or, depending on direction of movement of housing 1062, is collapsed back into proximal sheath 1069.

Figure 46:
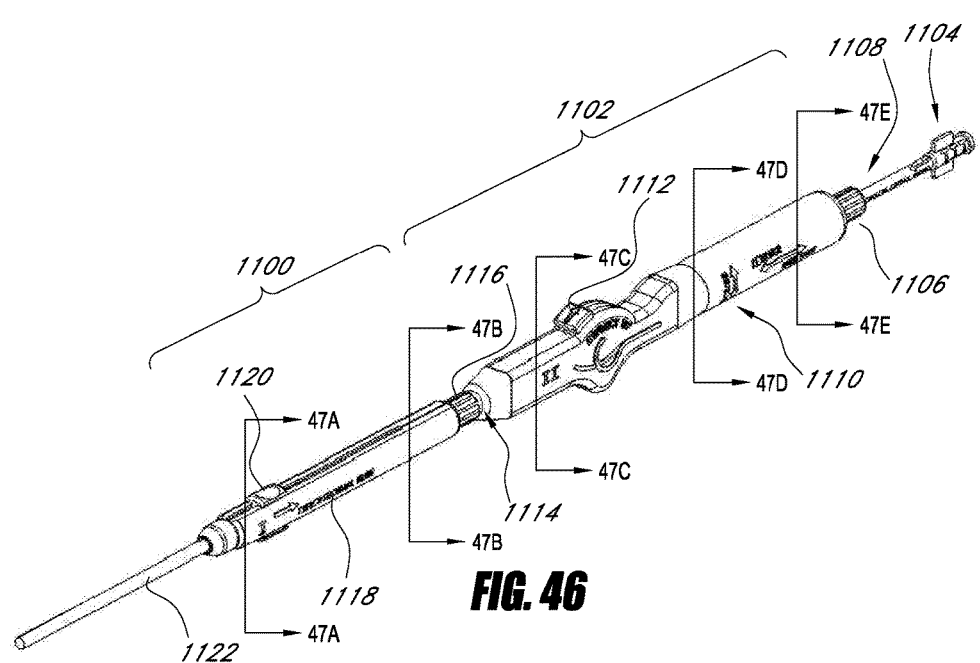

FIG. 46 depicts another embodiment of a control handle. The control handle has a proximal filter control 1100 and a distal filter control 1102. To deploy the device, the distal shaft of the catheter is fed over a guidewire and manipulated into position in the patient's anatomy. To deploy the proximal filter, the proximal filter sheath control 1120 is withdrawn proximally while holding the proximal filter handle 1118 stationary. The proximal filter sheath control 1120 is a sliding control; however, any other control such as a rotating knob, a pivoting lever, etc. may be used to withdraw the sheath.

When the proximal filter is properly deployed, the distal filter contained in the distal sheath is advanced distally and positioned in the target location by advancing the distal filter control 1102 while holding the proximal filter control 1100 stationary. During this positioning process, the distal filter control 1102 can be advanced, retracted or rotated relative to the proximal filter control 1100, and as needed, the deflection of the distal sheath may be controlled by actuating the distal sheath deflection control 1112 relative to the distal filter sheath handle 1110. The distal sheath deflection control 1112 is a pivoting control; however, any other control such as a rotating knob, a sliding knob, etc. may be used to deflect the sheath. Once the sheath containing the collapsed distal filter is positioned correctly, the position of the distal filter control 1102 is locked relative to the proximal filter control 1100 by tightening the proximal handle hemostasis valve 1116. Next, the distal filter may be deployed by advancing the guiding member 1108 by grasping the distal filter Luer fitting 1104 until the filter is deployed. The position and orientation of the distal filter may be adjusted by advancing, retracting or rotating the distal filter Luer fitting 1104 relative to the distal filter sheath handle 1110. Finally, the position of the distal filter may be fixed relative to the distal filter sheath handle 1110 by tightening the distal handle hemostasis valve 1106. To remove the device upon completion of the procedure, the aforementioned procedure is reversed.

FIGS. 47A through 47I illustrate cross-sections through the control handle illustrated in FIG. 46, taken along the section lines indicated in FIG. 46.

Figure 47A:
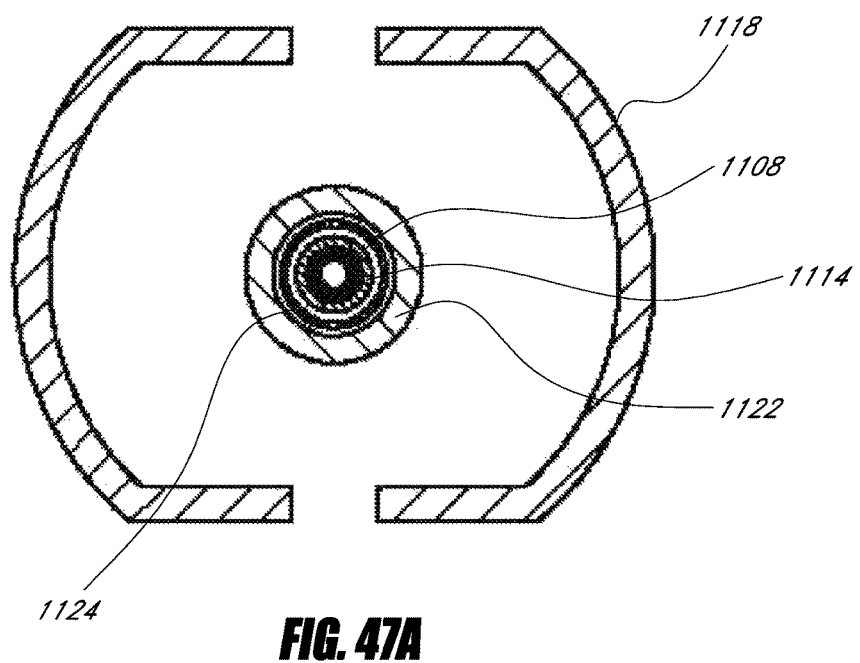
FIGS. 47A-H illustrate cross-sectional portions of an exemplary control handle.
Figure 47B:
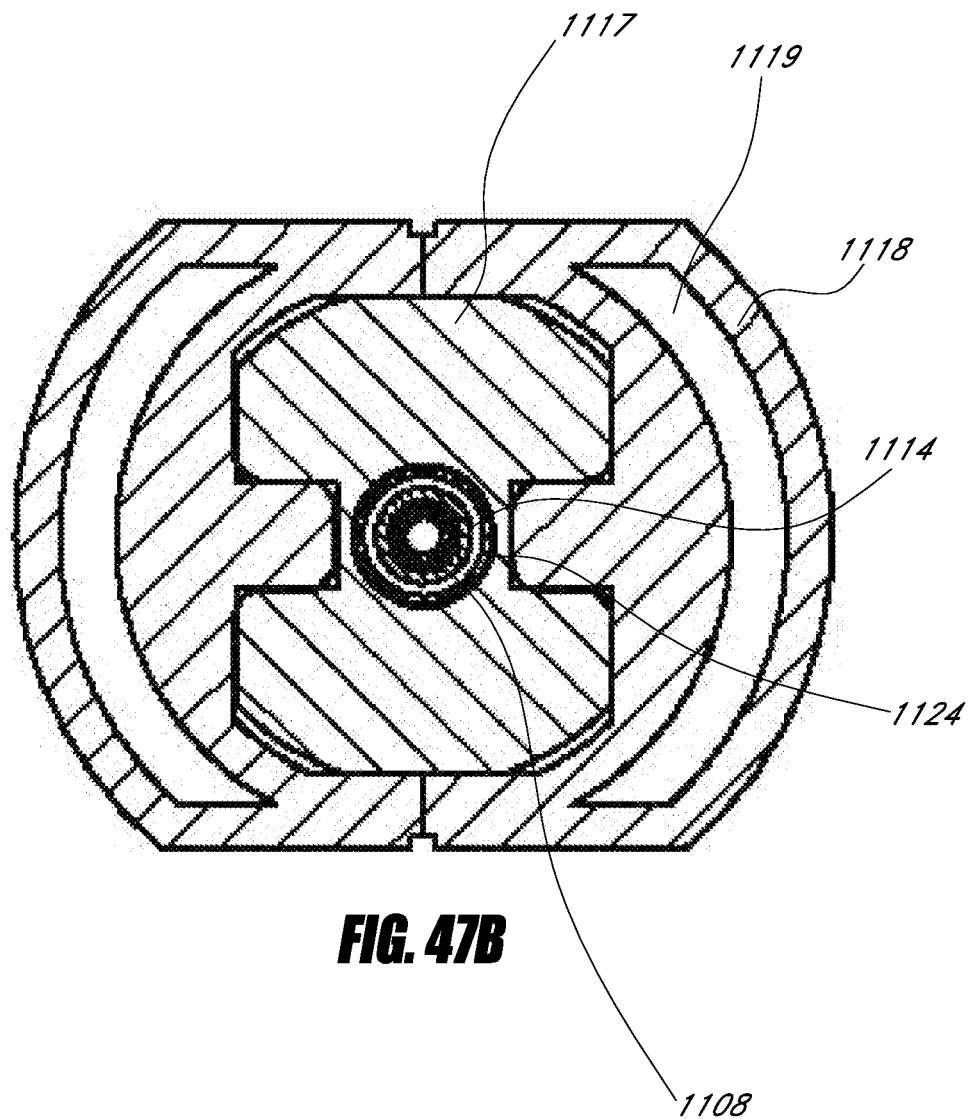

FIGS. 47A-B depict cross-sectional areas of proximal filter control 1100. The distal shaft 1108 is disposed through a lumen defined by the articulating distal sheath 1114. In these figures, the articulating distal sheath 1114 is disposed through a lumen defined by the proximal filter shaft 1124, and the proximal filter shaft is disposed through a lumen defined by the front handle 1118.

Figure 47C:
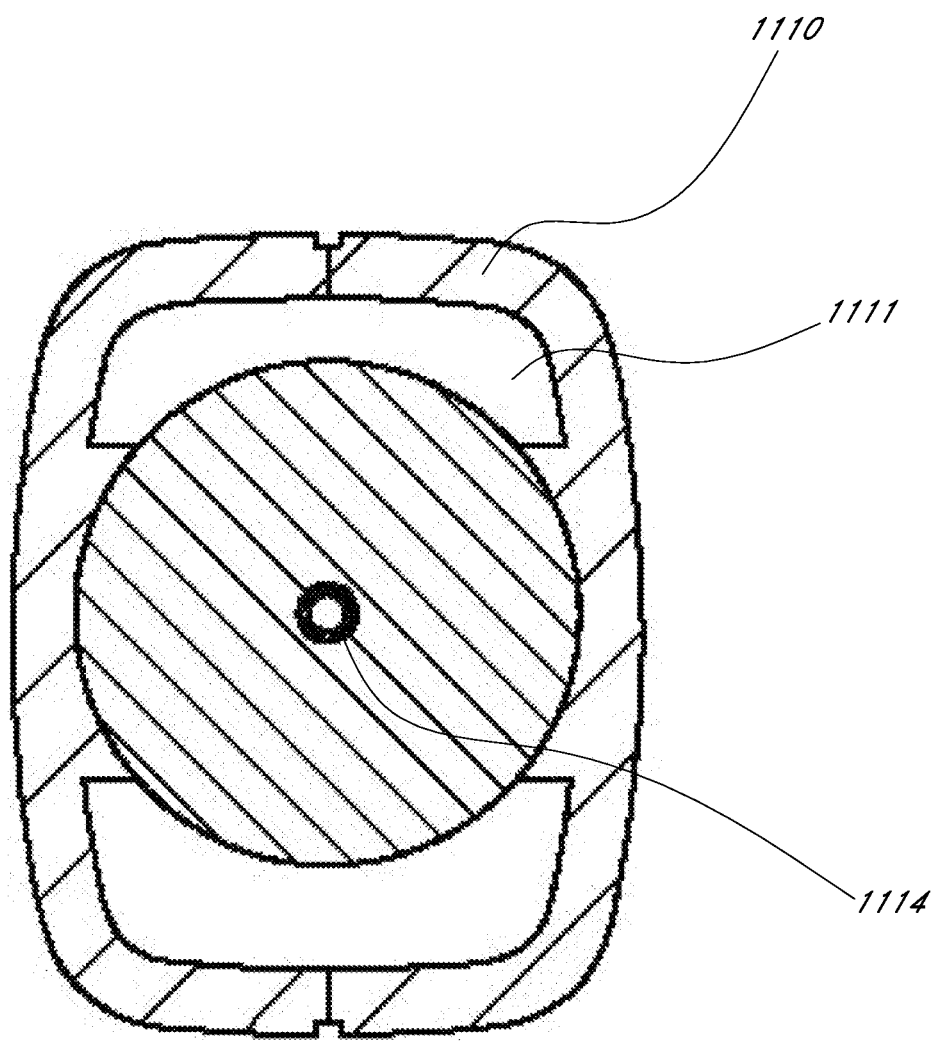
Figure 47D:
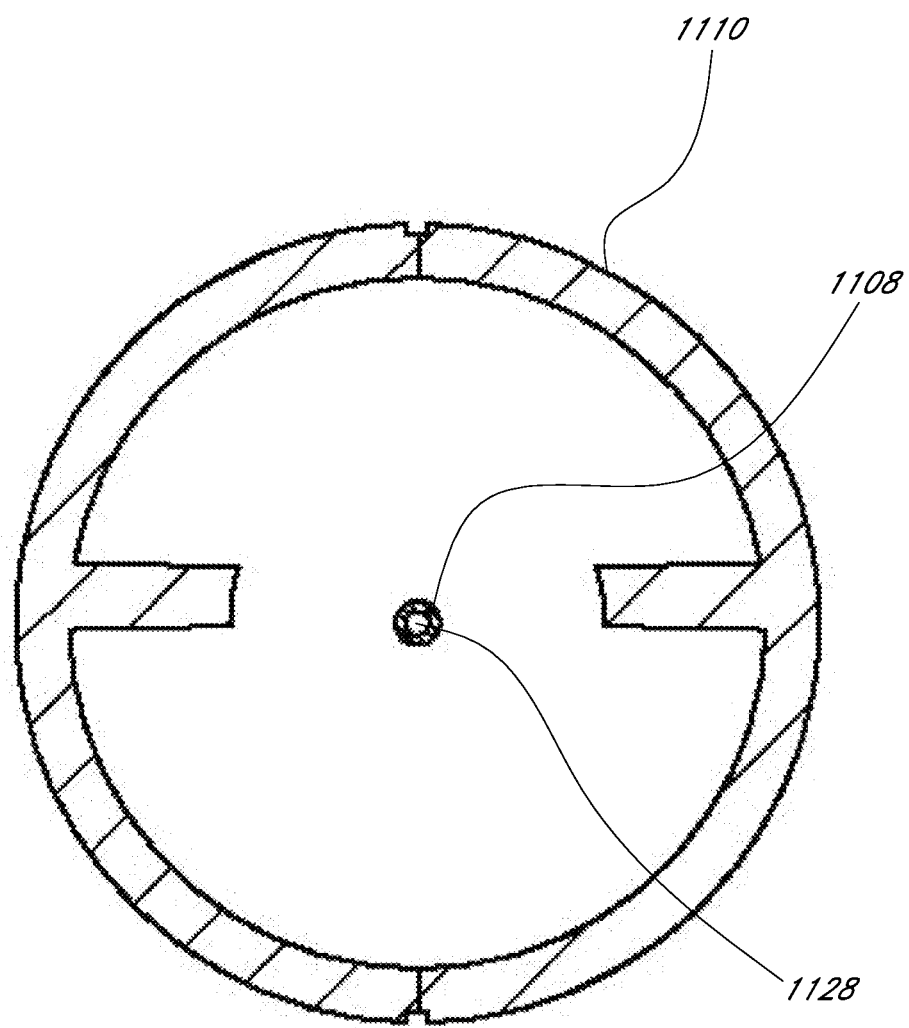
Figure 47E:
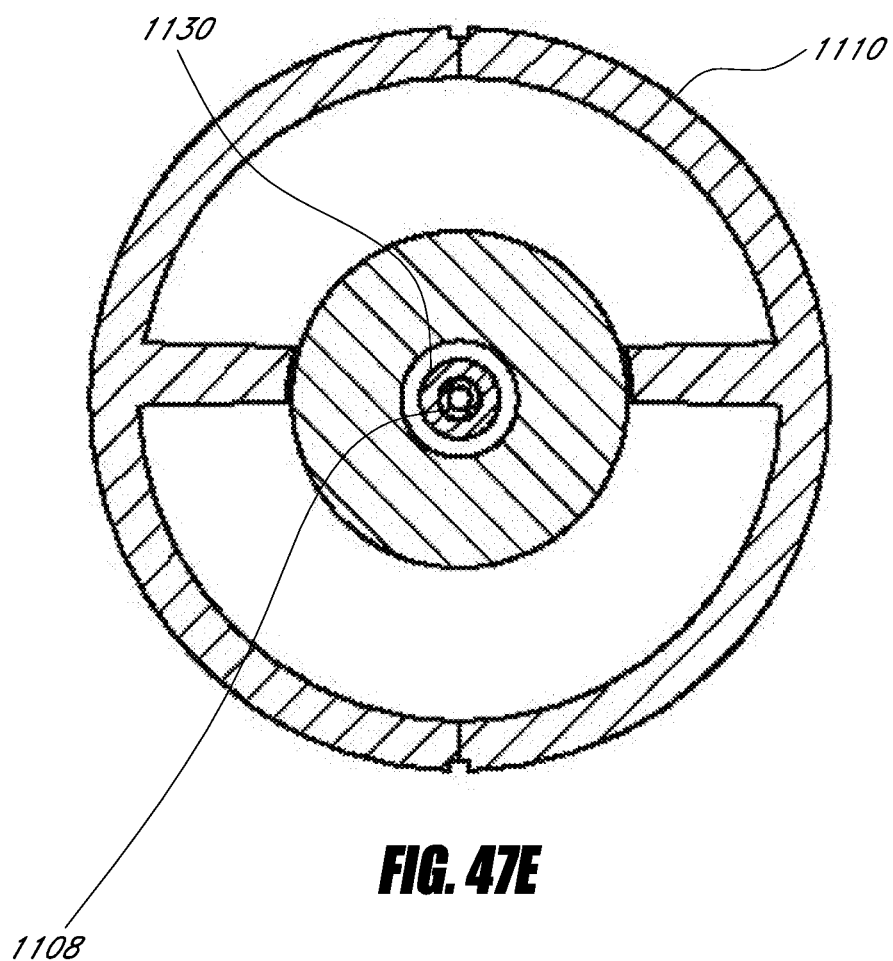

FIG. 47C depicts a cross-sectional area of a distal section of distal filter control 1102. In FIG. 47C, articulating distal sheath 1114 is disposed through a lumen defined by the rear handle 1110 as shown in FIG. 47C. FIG. 47D shows a cross-sectional view proximal to the cross-section shown in FIG. 47C. In FIG. 47D, guiding member 1108 is disposed through a lumen defined by the rear handle 1110. Guiding member 1108 defines a lumen 1128 through which a guidewire may pass. FIG. 47E shows a cross-sectional view proximal to the cross-section shown in FIG. 47D. The guiding member 1108 is coaxial with a stainless steel hypotube 1130. Hypotube 1130 reinforces the guiding member 1108.

Figure 47F:
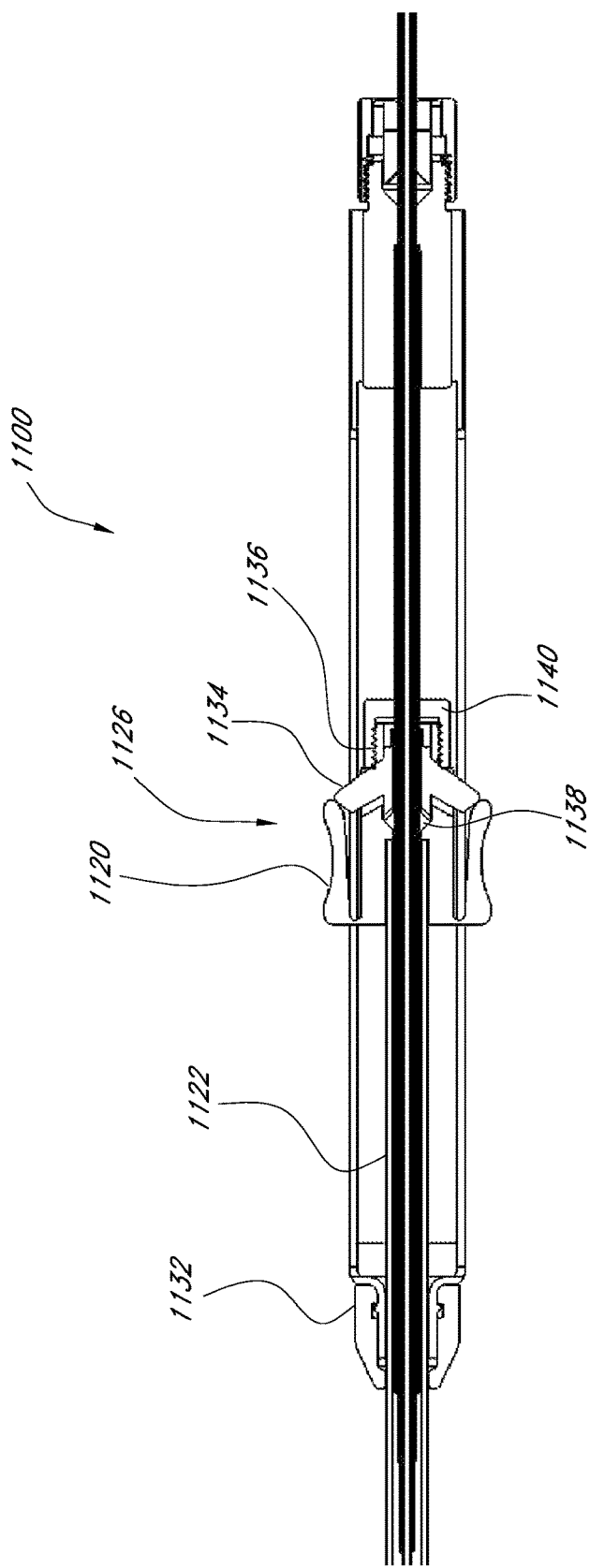

FIG. 47F depicts a longitudinal cross-section of proximal filter control 1100. At the distal end of proximal filter control 1100, there is a nose piece 1132 holding the front handle 1118 together. Proximal to nose piece 1132 there is a proximal filter sheath control 1120 to actuate the proximal filter sheath and deploy the proximal filter. The proximal filter sheath control is associated with a locking mechanism 1126 to prevent unintentional filter deployment and to actuate a sealing mechanism to prevent blood leakage. The locking mechanism 1126 comprises a locking element 1134, an elastomeric seal 1138, a spring 1136, and a nut 1140 for holding locking mechanism 1126 together. In certain embodiments, squeezing the proximal filter sheath control 1120 will release the locking element 1134 between the proximal sheath 1122 and proximal filter shaft 1124.

Figure 47G:
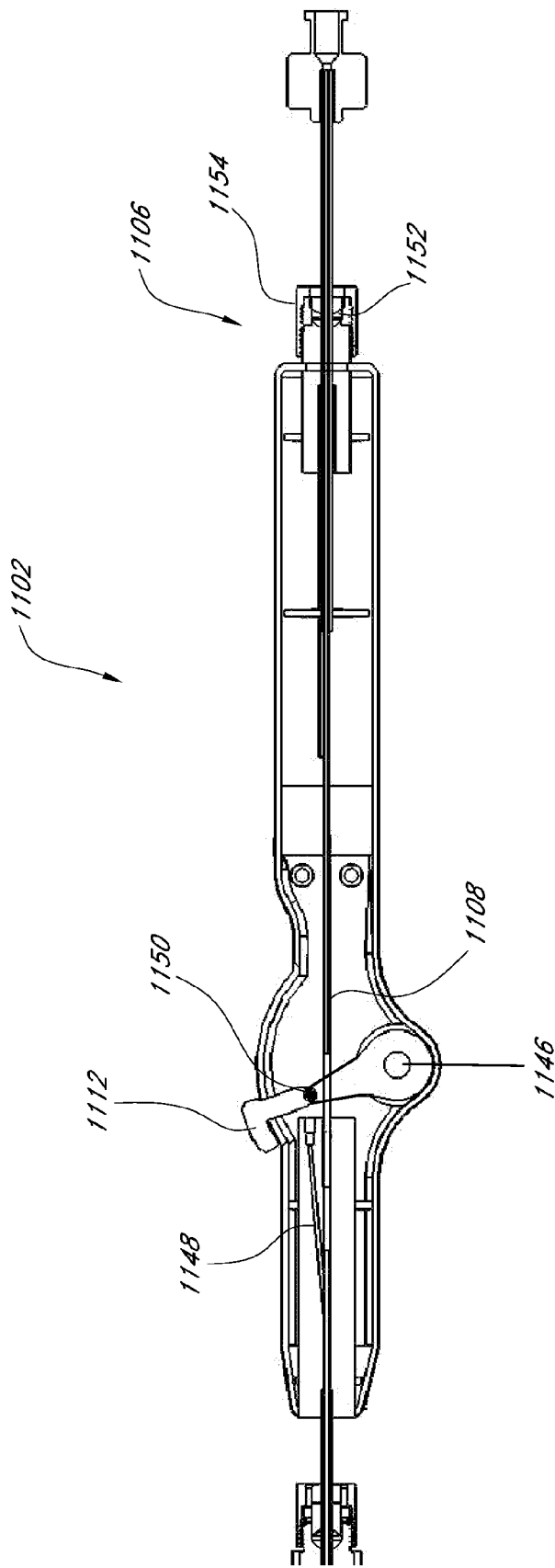
Figure 47H:
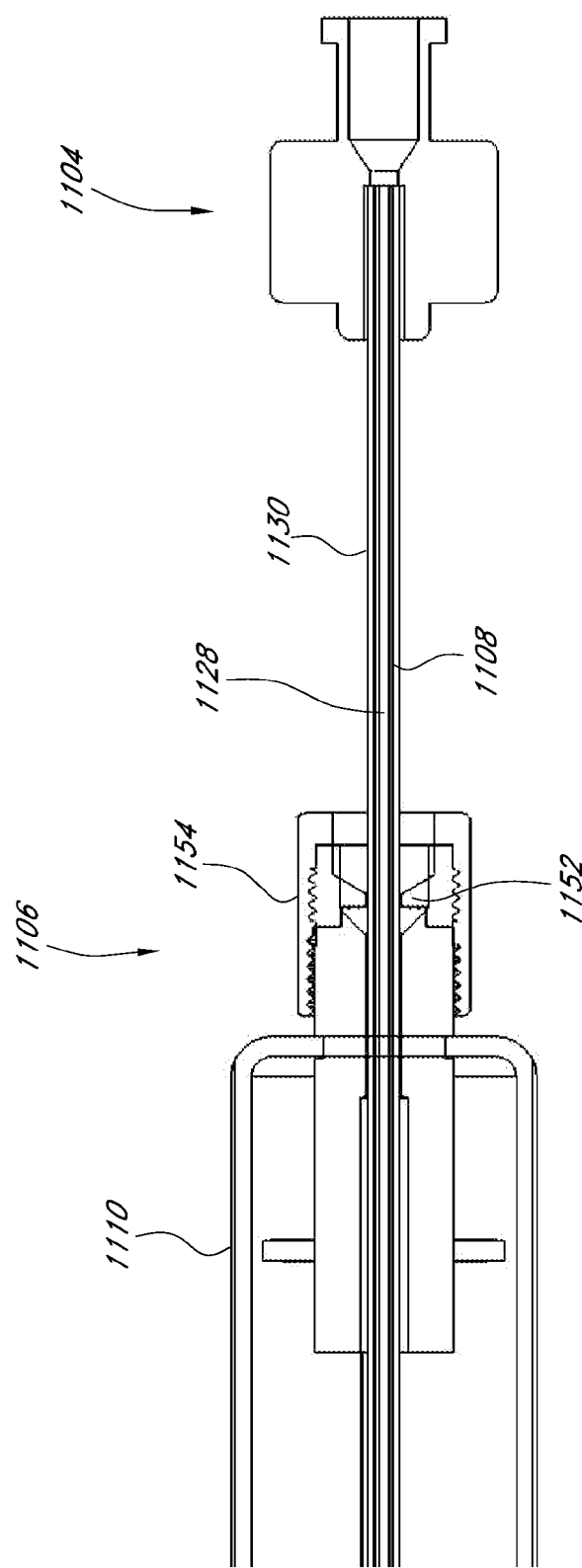

FIGS. 47G-H depicts a longitudinal cross section of distal filter control 1102. At a distal section of the distal filter control 1102, there is a mechanism to actuate articulating distal sheath 1114. The actuation mechanism includes an axially movable deflection lever 1112 pivoting on distal sheath pivot 1146. The distal sheath deflection lever 1112 is connected to the distal sheath pull wire at attachment point 1150. The pull wire is disposed through channel 1148. Proximal to rear handle 1110 there is a distal handle hemostasis valve 1106. Distal handle hemostasis valve 1106 comprises elastomeric seal 1152 and HV nut 1154. Distal filter shaft 1108 and hypotube 1130 extend proximally from distal filter control 1102 and terminate at distal filter luer lock fitting 1104.

Figure 48:
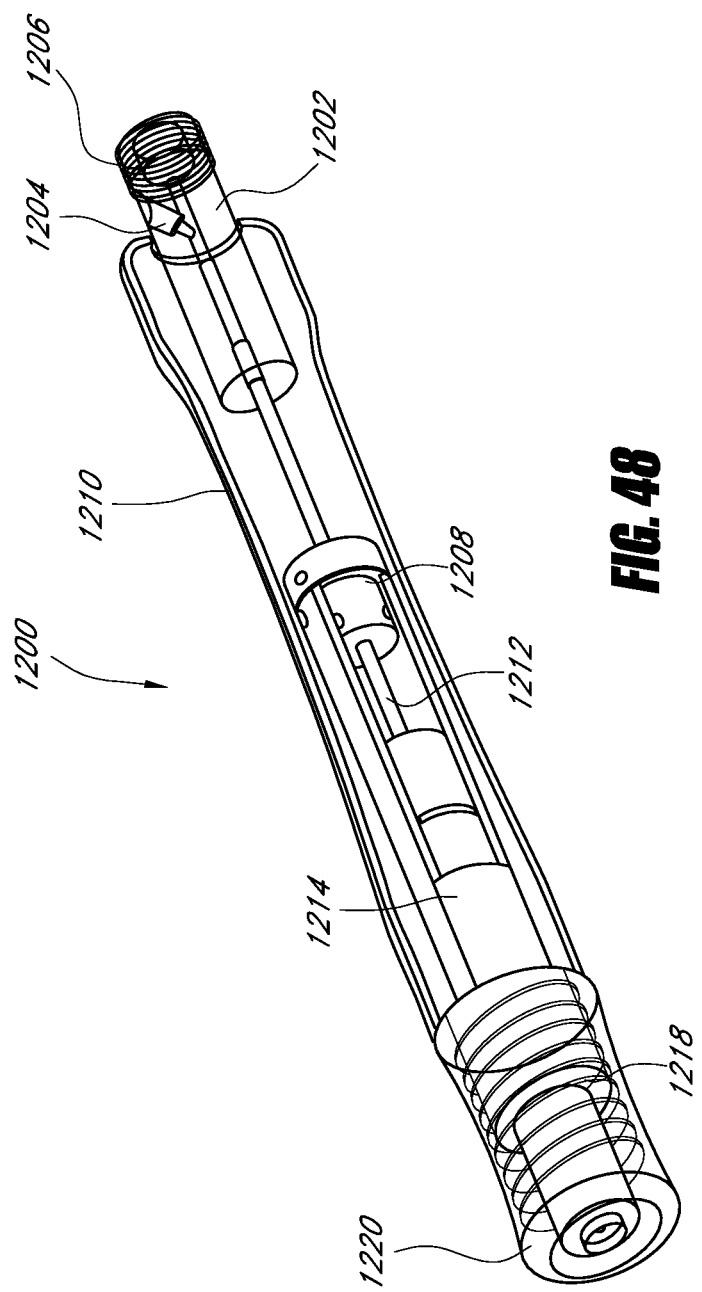
FIG. 48 depicts an alternative control handle with a rotary tip deflection control.

An alternative control handle uses a rotating screw drive mechanism to deflect a distal end of a distal articulating sheath is shown in FIG. 48. In certain clinical scenarios, it may be desirable to include a mechanism that prevents the articulating sheath from unintentionally deflecting when the operator releases the handle. The mechanism incorporates a lead screw 1214 which is inherently self-locking in that tip deflection will be locked wherever the handle control is released by the operator. A rotating screw drive mechanism provides an easy to manufacture design to control the pivot of the articulating sheath. The rate of deflection of the tip is controlled by the pitch of the screw threads 1218, thus rapid deflection of the tip, which can lead to unintentional vessel damage, can be prevented.

While specific embodiments have been described herein, it will be obvious to those skilled in the art that such embodiments are provided by way of example only. Numerous variations, changes, and substitutions will now occur to those skilled in the art without departing from that which is disclosed. It should be understood that various alternatives to the embodiments described herein may be employed in practicing the disclosure.

What is claimed is:

1. A method of isolating the cerebral circulation during a procedure, comprising the steps of:
    advancing a catheter system through the right subclavian artery, through the aorta, and into the left common carotid artery, the catheter system comprising a control handle having a proximal filter control and a distal filter control, the proximal filter control comprising a sliding control, the distal filter control comprising a distal sheath deflection control and a distal filter sheath handle;
    opening a proximal filter within the brachiocephalic artery by withdrawing the sliding control; and
    positioning a distal sheath containing a distal filter by axially moving the distal filter control;
    deflecting the distal sheath by rotating a distal sheath deflection control relative to the distal filter sheath handle;
    opening the distal filter within the left common carotid artery by advancing a distal filter actuator.

2. The method of isolating a cerebral circulation as in claim 1, wherein each filter has an open end and a closed end; and the open end of each of the proximal and distal filters face the aorta in a deployed orientation.

3. The method of isolating the cerebral circulation as in claim 2, wherein the procedure comprises a heart valve procedure.

4. The method of isolating the cerebral circulation as in claim 3, wherein the procedure comprises a transcatheter heart valve replacement procedure.

5. The method of isolating the cerebral circulation as in claim 1, further comprising deflecting the distal filter to draw a portion of the filter toward a vessel wall.

6. The method of claim 1, further comprising resheathing the proximal filter by advancing the sliding control.

7. The method of claim 1, further comprising holding the proximal filter control stationary while advancing the distal filter control.

8. The method of claim 1, further comprising orienting the distal filter by rotating the distal filter actuator.

9. The method of claim 1, further comprising retracting the distal filter by withdrawing the distal filter actuator.

10. The method of claim 1, wherein rotating the distal sheath deflection control comprises rotating a screw drive mechanism deflect the distal sheath.

11. The method of claim 10, wherein the screw drive mechanism comprises a self-locking screw to prevent the distal sheath from unintentionally deflecting.

12. A method of isolating the cerebral circulation during a procedure, comprising the steps of:
    advancing a catheter system through the right subclavian artery, through the aorta, and into the left common carotid artery, the catheter system comprising a control handle having a proximal filter control and a distal filter control, the distal filter control comprising a distal filter sheath handle;
    opening a proximal filter within the brachiocephalic artery using the proximal filter control; and
    positioning a distal sheath containing a distal filter by axially moving the distal filter control;
    after positioning the distal sheath, locking a position of the distal filter control relative to the proximal filter control by locking a proximal filter control lock;
    opening the distal filter within the left common carotid artery by advancing a distal filter actuator; and
    after opening the distal filter, locking a position of the distal filter relative to the distal filter sheath handle by locking a position of a distal filter control lock.

13. The method of claim 12, wherein the distal filter control lock is positioned between the distal filter sheath handle and the distal filter actuator.

14. The method of claim 12, wherein the proximal filter control lock is positioned proximal of the proximal filter control.

15. The method of claim 12, further comprising deflecting the distal sheath by rotating a distal sheath deflection control of the distal filter control relative to the distal filter sheath handle.

16. The method of claim 15, wherein rotating the distal sheath deflection control comprises rotating a screw drive mechanism deflect the distal sheath.

17. The method of claim 16, wherein the screw drive mechanism comprises a self-locking screw to prevent the distal sheath from unintentionally deflecting.

18. The method of claim 12, further comprising holding the proximal filter control stationary while advancing the distal filter control.

19. The method of claim 12, further comprising orienting the distal filter by rotating the distal filter actuator.

20. The method of claim 12, further comprising retracting the distal filter by withdrawing the distal filter actuator.

* * * * *